US009029147B2

(12) United States Patent
Colton et al.

(10) Patent No.: US 9,029,147 B2
(45) Date of Patent: May 12, 2015

(54) METHODS AND COMPOSITIONS FOR ENHANCED DIFFERENTIATION FROM EMBRYONIC STEM CELLS

(75) Inventors: Clark K. Colton, Newton, MA (US);
Daryl E. Powers, Cambridge, MA (US);
Jeffrey R. Millman, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 422 days.

(21) Appl. No.: 12/664,763

(22) PCT Filed: Jun. 13, 2008

(86) PCT No.: PCT/US2008/007459
§ 371 (c)(1),
(2), (4) Date: Apr. 20, 2010

(87) PCT Pub. No.: WO2008/156708
PCT Pub. Date: Dec. 24, 2008

(65) Prior Publication Data
US 2010/0261277 A1    Oct. 14, 2010

Related U.S. Application Data

(60) Provisional application No. 60/934,742, filed on Jun. 15, 2007, provisional application No. 61/125,041, filed on Apr. 22, 2008.

(51) Int. Cl.
*C12N 5/02*    (2006.01)
*C12N 5/00*    (2006.01)
*C12N 5/077*   (2010.01)

(52) U.S. Cl.
CPC .......... *C12N 5/0657* (2013.01); *C12N 2500/25* (2013.01); *C12N 2500/34* (2013.01); *C12N 2500/38* (2013.01); *C12N 2501/235* (2013.01); *C12N 2506/02* (2013.01); *C12N 2533/30* (2013.01)

(58) Field of Classification Search
None
See application file for complete search history.

(56) References Cited

U.S. PATENT DOCUMENTS

| | | | |
|---|---|---|---|
| 5,942,435 A * | 8/1999 | Wheeler | 435/325 |
| 6,534,052 B1 | 3/2003 | Xiao et al. | |
| 6,613,568 B2 | 9/2003 | Kaufman et al. | |
| 6,833,269 B2 | 12/2004 | Carpenter | |
| 7,033,831 B2 | 4/2006 | Fisk et al. | |
| 7,250,294 B2 | 7/2007 | Carpenter et al. | |
| 7,282,366 B2 | 10/2007 | Rambhatla et al. | |
| 7,326,572 B2 | 2/2008 | Fisk et al. | |
| 7,425,448 B2 | 9/2008 | Xu | |
| 7,732,199 B2 | 6/2010 | Xu | |
| 2005/0164382 A1 | 7/2005 | Xu | |
| 2005/0266554 A1 | 12/2005 | D'Amour et al. | |

FOREIGN PATENT DOCUMENTS

| | | | |
|---|---|---|---|
| WO | WO 00/29550 A2 | 5/2000 | |
| WO | WO 2008/156708 A2 | 12/2008 | |
| WO | WO 2009/007852 A2 | 1/2009 | |
| WO | WO 2009/035217 A1 | 3/2009 | |
| WO | WO 2009/079007 A1 | 6/2009 | |

OTHER PUBLICATIONS

Hoffman and Carpenter, 2005, Nature Biotechnology, 23:699-708.*
Ramirez, 2006, Reproduction, fertility and Development, 19(2) 209-210.*
Fehling, Development, 2003, 130:4217-4227.*
Dang Stem Cells, 2004, 22: 275-282.*
Ramirez-Bergeron, Development, 2004, 131:4623-4634.*
Millman, Current Opinion in Organ Transplantation, 2009, 14:694-700.*
Ginis Dev Biol 269 360-380 2004.*
Sato et al. 2004 Nat. Med. 10:55-63.*
Humphrey et al. (2004) Stem Cells 22: 522-530.*
Xu et al. (2005) Nature Methods 2:185-190.*
[No Author Listed]. Innovative cell culture devices to help expand your growth. Wilson Wolf Manufacturing, Inc. Accessed online at http://www.wilsonwolf.com/technology.htm on Jun. 4, 2008. 1 page.
[No Author Listed] FDA Center for Biologics Evaluation and Research: Cellular, Tissue, and Gene Therapeutics Advisory Committee, Summary Minutes. Meeting #45. Apr. 10-11, 2008.
Ai et al., Biocompatibility of layer-by-layer self-assembled nanofilm on silicone rubber for neurons. J Neurosci Methods. Sep. 30, 2003;128(1-2):1-8. Abstract only.
Avgoustiniatos, Oxygen diffusion limitations in pancreatic islet culture and immunoisolation. Thesis; Massachusetts Institute of Technology.2002. Abstract only.
Baharvand et al., Differentiation of human embryonic stem cells into hepatocytes in 2D and 3D culture systems in vitro. Int J Dev Biol. 2006;50(7):645-52. Abstract only.
Bauwens et al., Development of a perfusion fed bioreactor for embryonic stem cell-derived cardiomyocyte generation: oxygen-mediated enhancement of cardiomyocyte output. Biotechnol Bioeng. May 20, 2005;90(4):452-61.
Bjorklund et al., Embryonic stem cells develop into functional dopaminergic neurons after transplantation in a Parkinson rat model. Proc Natl Acad Sci U S A. Feb. 19, 2002;99(4):2344-9. Epub Jan. 8, 2002.
Blum et al., Clonal analysis of human embryonic stem cell differentiation into teratomas. Stem Cells. Aug. 2007;25(8):1924-30. Epub Apr. 26, 2007.
Blum et al., The tumorigenicity of human embryonic stem cells. Adv Cancer Res. 2008;100:133-58.
Bondue et al., Mesp1 acts as a master regulator of multipotent cardiovascular progenitor specification. Cell Stem Cell. Jul. 3, 2008;3(1):69-84.
Bonner-Weir et al., In vitro cultivation of human islets from expanded ductal tissue. Proc Natl Acad Sci U S A. Jul. 5, 2000;97(14):7999-8004.
Brederlau et al., Transplantation of human embryonic stem cell-derived cells to a rat model of Parkinson's disease: effect of in vitro differentiation on graft survival and teratoma formation. Stem Cells. Jun. 2006;24(6):1433-40. Epub Mar. 23, 2006.
Brunelle et al., Oxygen deprivation induced cell death: an update. Apoptosis. Dec. 2002;7(6):475-82. Abstract only.

(Continued)

*Primary Examiner* — Valarie Bertoglio
(74) *Attorney, Agent, or Firm* — Wolf, Greenfield & Sacks, P.C.

(57) ABSTRACT

The invention provides methods for differentiating pluripotent stem cells such as ES cells with improved progenitor and differentiated cell yield using low oxygen conditions and optionally in the absence of exogenously added differentiation factors.

14 Claims, 30 Drawing Sheets

(56) References Cited

OTHER PUBLICATIONS

Brusselmans et al., A novel role for vascular endothelial growth factor as an autocrine survival factor for embryonic stem cells during hypoxia. J Biol Chem. Feb. 4, 2005;280(5):3493-9. Epub Nov. 29, 2004.
Caspi et al., Transplantation of human embryonic stem cell-derived cardiomyocytes improves myocardial performance in infarcted rat hearts. J Am Coll Cardiol. Nov. 6, 2007;50(19):1884-93. Epub Oct. 23, 2007.
Csete, Oxygen in the cultivation of stem cells. Ann N Y Acad Sci. May 2005;1049:1-8. Abstract only.
Cunningham et al., Quantification of fibronectin adsorption to silicone-rubber cell culture substrates. Biotechniques.Apr. 2002;32(4):876, 878, 880 passim. Abstract only.
D'Amour et al., Efficient differentiation of human embryonic stem cells to definitive endoderm. Nat Biotechnol. Dec. 2005;23(12):1534-41. Epub Oct. 28, 2005. Abstract only.
D'Amour et al.,Production of pancreatic hormone-expressing endocrine cells from human embryonic stem cells. Nat Biotechnol. Nov. 2006;24(11):1392-401. Epub Oct. 19, 2006.
Daley et al., Realistic prospects for stem cell therapeutics. Hematology Am Soc Hematol Educ Program. 2003:398-418.
Damjanov et al., The terminology of teratocarcinomas and teratomas. Nat Biotechnol. Nov. 2007;25(11):1212; discussion 1212.
David et al., MesP1 drives vertebrate cardiovascular differentiation through Dkk-1-mediated blockade of Wnt-signalling. Nat Cell Biol. Mar. 2008;10(3):338-45. Epub Feb. 24, 2008. Abstract only.
Drukker et al., Human embryonic stem cells and their differentiated derivatives are less susceptible to immune rejection than adult cells. Stem Cells. Feb. 2006;24(2):221-9. Epub Aug. 18, 2005.
Erdöe et al., Host-dependent tumorigenesis of embryonic stem cell transplantation in experimental stroke. J Cereb Blood Flow Metab. Jul. 2003;23(7):780-5.
Fernandes et al., Different stages of pluripotency determine distinct patterns of proliferation, metabolism, and lineage commitment of embryonic stem cells under hypoxia. Stem Cell Res. Jul. 2010;5(1):76-89. Epub Apr. 22, 2010.
Fraker et al., Enhanced oxygenation promotes beta-cell differentiation in vitro. Stem Cells. Dec. 2007;25(12):3155-64.Epub Aug. 30, 2007.
Fukuda et al., Stem cells as a source of regenerative cardiomyocytes. Circ Res. Apr. 28, 2006;98(8):1002-13.
Gerecht-Nir et al., Human embryonic stem cells as an in vitro model for human vascular development and the induction of vascular differentiation. Lab Invest. Dec. 2003;83(12):1811-20. Abstract only.
Grapin-Botton et al., Endoderm development: from patterning to organogenesis. Trends Genet. Mar. 2000;16(3):124-30. Abstract only.
Gu et al., Direct lineage tracing reveals the ontogeny of pancreatic cell fates during mouse embryogenesis. Mech Dev. Jan. 2003;120(1):35-43. Abstract only.
Hentze et al., Cell therapy and the safety of embryonic stem cell-derived grafts. Trends Biotechnol. Jan. 2007;25(1):24-32. Epub Nov. 3, 2006.
Hoffman et al., Characterization and culture of human embryonic stem cells. Nature Biotechnology Jun. 2005; 23(6):699-708.
Horton et al., Engineering microenvironments for embryonic stem cell differentiation to cardiomyocytes. Regen Med. Sep. 2009;4(5):721-32.
Jaenisch et al., Stem cells, the molecular circuitry of pluripotency and nuclear reprogramming Cell. Feb. 22, 2008;132(4):567-82.
Jensen et al., Diffusion in tissue cultures on gas-permeable and impermeable supports. J Theor Biol. Feb. 1976;56(2):443-58.
Kaufman et al., Hematopoietic colony-forming cells derived from human embryonic stem cells. Proc Natl Acad Sci U S A. Sep. 11, 2001;98(19):10716-21. Epub Sep. 4, 2001.
Kehat et al., Human embryonic stem cells for myocardial regeneration. Heart Fail Rev. Jul. 2003;8(3):229-36. Abstract only.
Keller. Embryonic stem cell differentiation: emergence of a new era in biology and medicine. Genes Dev. May 15, 2005;19(10):1129-55.
Kim et al., Dopamine neurons derived from embryonic stem cells function in an animal model of Parkinson's disease. Nature. Jul. 4, 2002;418(6893):50-6. Epub Jun. 20, 2002. Abstract only.
Kim et al., Increase in dopaminergic neurons from mouse embryonic stem cell-derived neural progenitor/stem cells is mediated by hypoxia inducible factor-1alpha. J Neurosci Res. Aug. 15, 2008;86(11):2353-62.
Klug et al., Genetically selected cardiomyocytes from differentiating embronic stem cells form stable intracardiac grafts. J Clin Invest. Jul. 1, 1996;98(1):216-24.
Koay et al., Hypoxic chondrogenic differentiation of human embryonic stem cells enhances cartilage protein synthesis and biomechanical functionality. Osteoarthritis Cartilage. Dec. 2008;16(12):1450-6. Epub Jun. 9, 2008.
Kroon et al., Pancreatic endoderm derived from human embryonic stem cells generates glucose-responsive insulin-secreting cells in vivo. Nat Biotechnol. Apr. 2008;26(4):443-52. Epub Feb. 20, 2008
Kurosawa et al., Effect of oxygen on in vitro differentiation of mouse embryonic stem cells. J Biosci Bioeng. Jan. 2006;101(1):26-30.
Laflamme et al., Cardiomyocytes derived from human embryonic stem cells in pro-survival factors enhance function of infarcted rat hearts. Nat Biotechnol. Sep. 2007;25(9):1015-24. Epub Aug. 26, 2007. Abstract only.
Lam et al., Multipotent progenitor cells in regenerative cardiovascular medicine. Pediatr Cardiol. Jul. 2009;30(5):690-8. Epub May 5, 2009. Abstract only.
Lavon et al., Differentiation and isolation of hepatic-like cells from human embryonic stem cells. Differentiation. Jun. 2004;72(5):230-8. Abstract only.
Lawrenz et al., Highly sensitive biosafety model for stem-cell-derived grafts. Cytotherapy. 2004;6(3):212-22. Abstract only.
Lee et al., Efficient generation of midbrain and hindbrain neurons from mouse embryonic stem cells. Nat Biotechnol. Jun. 2000;18(6):675-9. Abstract only.
Lensch et al., The terminology of teratocarcinomas and teratomas. Nat Biotechnol. Nov. 2007;25(11):1211; author reply 1211-2.
Leor et al., Human embryonic stem cell transplantation to repair the infarcted myocardium. Heart. Oct. 2007;93(10):1278-84. Epub Jun. 12, 2007.
Lindsley et al., Mesp1 coordinately regulates cardiovascular fate restriction and epithelial-mesenchymal transition in differentiating ESCs. Cell Stem Cell. Jul. 3, 2008;3(1):55-68.
Ma et al., Hypoxia and stem cell-based engineering of mesenchymal tissues. Biotechnol Prog. Jan.-Feb. 2009;25(1):32-42.
McLimans et al., Kinetics of gas diffusion in mammalian cell culture systems. I. Experimental. Biotechnol Bioeng. Nov. 1968;10:725-740.
Millman et al. "Extended Low Oxygen Culture of Mouse Embryonic Stem Cells Reduces the Fraction of Tumor-Forming Residual Pluripotent Cells in Differentiated Populations", NIH Symposium on Cardiovascular Regenerative Medicine, Bethesda, MD, Oct. 14-15, 2009.
Millman et al., "Differentiation of murine embryonic stem cells under low oxygen influences cardiomyocyte yield and timing and magnitude of cardiomyocyte gene expression", NIH Symposium on Cardiovascular Regenerative Medicine, Bethesda, MD, Oct. 14-15, 2009.
Millman et al., Culture under low oxygen conditions markedly enhances differentiation of murine embryonic stem cells into cardiomyocytes, The $5^{th}$ International Society for Stem Cell Research (ISSCR) Annual Meeting, Cairns, Australia, Jun. 17-20, 2007.
Millman et al., Low oxygen influences the self-renewal and differentiation of murine embryonic stem cells, the $6^{th}$ International Society for Stem Cell Research (ISSCR) Annual Meeting, Philadelphia, PA, Jun. 11-14, 2008.
Mondragon-Teran et al., Lowering oxygen tension enhances the differentiation of mouse embryonic stem cells into neuronal cells. Biotechnol Prog. Sep.-Oct. 2009;25(5):1480-8.
Niebruegge et al., Generation of human embryonic stem cell-derived mesoderm and cardiac cells using size-specified aggregates in an oxygen-controlled bioreactor. Biotechnol Bioeng. Feb. 1, 2009;102(2):493-507.

(56) References Cited

OTHER PUBLICATIONS

Nir et al., Human embryonic stem cells for cardiovascular repair. Cardiovasc Res. May 1, 2003;58(2):313-23. Abstract only.

Okazaki et al., Oxygen, epigenetics and stem cell fate. Regen Med. Jan. 2006;1(1):71-83. Abstract only.

Papas et al., High-density culture of human islets on top of silicone rubber membranes. Transplant Proc. Oct. 2005;37(8):3412-4.

Pei, Regulation of pluripotency and reprogramming by transcription factors. J Biol Chem. Feb. 6, 2009;284(6):3365-9. Epub Sep. 26, 2008.

Pera et al., Regulation of human embryonic stem cell differentiation by BMP-2 and its antagonist noggin. J Cell Sci. Mar. 1, 2004;117(Pt 7):1269-80.

Powers et al., Accurate control of oxygen level in cells during culture on silicone rubber membranes with application to stem cell differentiation. Biotechnol Prog. May-Jun. 2010;26(3):805-18.

Powers et al., Effects of oxygen on mouse embryonic stem cell growth, phenotype retention, and cellular energetics. Biotechnol Bioeng. Oct. 1, 2008;101(2):241-54.

Przyborski, Differentiation of human embryonic stem cells after transplantation in immune-deficient mice. Stem Cells. Oct. 2005;23(9):1242-50.

Purpura et al., Soluble Flt-1 regulates Flk-1 activation to control hematopoietic and endothelial development in an oxygen-responsive manner. Stem Cells. Nov. 2008;26(11):2832-42. Epub Sep. 4, 2008.

Rambhatla et al., Generation of hepatocyte-like cells from human embryonic stem cells. Cell Transplant. 2003;12(1):1-11. Abstract only.

Ramírez-Bergeron et al., Hypoxia-inducible factor and the development of stem cells of the cardiovascular system. Stem Cells. 2001;19(4):279-86.

Schwartz et al., Defined conditions for development of functional hepatic cells from human embryonic stem cells. Stem Cells Dev. Dec. 2005;14(6):643-55. Abstract only.

Semenza et al., Regulation of cardiovascular development and physiology by hypoxia-inducible factor 1. Ann N Y Acad Sci. Jun. 30, 1999;874:262-8. Abstract only.

Shih et al., Human embryonic stem cells are prone to generate primitive, undifferentiated tumors in engrafted human fetal tissues in severe combined immunodeficient mice. Stem Cells Dev. Dec. 2007;16(6):893-902. Abstract only.

Shirahashi et al., Differentiation of human and mouse embryonic stem cells along a hepatocyte lineage. Cell Transplant. 2004;13(3):197-211.

Silván et al., Hypoxia and pluripotency in embryonic and embryonal carcinoma stem cell biology. Differentiation. Sep.-Oct. 2009;78(2-3):159-68. Epub Jul. 14, 2009.

Soto-Gutierrez et al., Differentiation of human embryonic stem cells to hepatocytes using deleted variant of HGF and poly-amino-urethane-coated nonwoven polytetrafluoroethylene fabric. Cell Transplant. 2006;15(4):335-41. Abstract only.

Spagnoli et al., Guiding embryonic stem cells towards differentiation: lessons from molecular embryology. Curr Opin Genet Dev. Oct. 2006;16(5):469-75. Epub Aug. 17, 2006. Abstract only.

Tian et al., Hematopoietic engraftment of human embryonic stem cell-derived cells is regulated by recipient innate immunity. Stem Cells. May 2006;24(5):1370-80. Epub Feb. 2, 2006.

West et al., In vitro gametogenesis from embryonic stem cells. Curr Opin Cell Biol. Dec. 2004;16(6):688-92. Abstract only.

Wion et al., $pO_2$ matters in stem cell culture. Cell Stem Cell. Sep. 4, 2009;5(3):242-3.

Wolff et al., Microelectrode measurements of pericellular $pO_2$ in erythropoietin-producing human hepatoma cell cultures. Am J Physiol. Nov. 1993;265(5 Pt 1):C1266-70. Abstract only.

Xu et al., BMP4 initiates human embryonic stem cell differentiation to trophoblast. Nat Biotechnol. Dec. 2002;20(12):1261-4. Epub Nov. 11, 2002. Abstract only.

Yoon et al., Enhanced differentiation of human embryonic stem cells into cardiomyocytes by combining hanging drop culture and 5-azacytidine treatment. Differentiation. Apr. 2006;74(4):149-59. Erratum in: Differentiation. Jul. 2006;74(6):322.

Yoshida et al., Hypoxia enhances the generation of induced pluripotent stem cells. Cell Stem Cell. Sep. 4, 2009;5(3):237-41.

Zandstra et al., Scalable production of embryonic stem cell-derived cardiomyocytes. Tissue Eng. Aug. 2003;9(4):767-78.

Zhou et al., A gene regulatory network in mouse embryonic stem cells. Proc Natl Acad Sci U S A. Oct. 16, 2007;104(42):16438-43. Epub Oct. 10, 2007.

Ai et al., Biocompatibility of layer-by-layer self-assembled nanofilm on silicone rubber for neurons. J Neurosci Methods. Sep. 30, 2003;128(1-2):1-8.

Avgoustiniatos, Oxygen diffusion limitations in pancreatic islet culture and immunoisolation. Thesis; Massachusetts Institute of Technology.2002.

Baharvand et al., Differentiation of human embryonic stem cells into hepatocytes in 2D and 3D culture systems in vitro. Int J Dev Biol. 2006;50(7):645-52.

Brunelle et al., Oxygen deprivation induced cell death: an update. Apoptosis. Dec. 2002;7(6):475-82.

Csete, Oxygen in the cultivation of stem cells. Ann N Y Acad Sci. May 2005;1049:1-8.

Cunningham et al., Quantification of fibronectin adsorption to silicone-rubber cell culture substrates. Biotechniques.Apr. 2002;32(4):876, 878, 880 passim.

D'Amour et al., Efficient differentiation of human embryonic stem cells to definitive endoderm. Nat Biotechnol. Dec. 2005;23(12):1534-41. Epub Oct. 28, 2005.

David et al., MesP1 drives vertebrate cardiovascular differentiation through Dkk-1-mediated blockade of Wnt-signalling. Nat Cell Biol. Mar. 2008;10(3):338-45. Epub Feb. 24, 2008.

Gerecht Nir et al., Human embryonic stem cells as an in vitro model for human vascular development and the induction of vascular differentiation. Lab Invest. Dec. 2008;83(12):1811-20.

Grapin-Botton et al., Endoderm development: from patterning to organogenesis. Trends Genet. Mar. 2000;16(3):124-30.

Gu et al., Direct lineage tracing reveals the ontogeny of pancreatic cell fates during mouse embryogenesis. Mech Dev. Jan. 2003;120(1):35-43.

Kehat et al., Human embryonic stem cells for myocardial regeneration. Heart Fail Rev. Jul. 2003;8(3):229-36.

Kim et al., Dopamine neurons derived from embryonic stem cells function in an animal model of Parkinson's disease. Nature. Jul. 4, 2002;418(6893):50-6. Epub Jun. 20, 2002.

Laflamme et al., Cardiomyocytes derived from human embryonic stem cells in pro-survival factors enhance function of infarcted rat hearts. Nat Biotechnol. Sep. 2007;25(9):1015-24. Epub Aug. 26, 2007.

Lam et al., Multipotent progenitor cells in regenerative cardiovascular medicine. Pediatr Cardiol. Jul. 2009;30(5):690-8. Epub May 5, 2009.

Lavon et al., Differentiation and isolation of hepatic-like cells from human embryonic stem cells. Differentiation. Jun. 2004;72(5):230-8.

Lawrenz et al., Highly sensitive biosafety model for stem-cell-derived grafts. Cytotherapy. 2004;6(3):212-22.

Lee et al., Efficient generation of midbrain and hindbrain neurons from mouse embryonic stem cells. Nat Biotechnol. Jun. 2000;18(6):675-9.

Nir et al., Human embryonic stem cells for cardiovascular repair. Cardiovasc Res. May 1, 2003;58(2):313-23.

Okazaki et al., Oxygen, epigenetics and stem cell fate. Regen Med. Jan. 2006;1(1):71-83.

Rambhatla et al., Generation of hepatocyte-like cells from human embryonic stem cells. Cell Transplant. 2003;12(1):1-11.

Schwartz et al., Defined conditions for development of functional hepatic cells from human embryonic stem cells. Stem Cells Dev. Dec. 2005;14(6):643-55.

Semenza et al., Regulation of cardiovascular development and physiology by hypoxia-inducible factor 1. Ann N Y Acad Sci. Jun. 30, 1999;874:262-8.

(56) References Cited

OTHER PUBLICATIONS

Shih et al., Human embryonic stem cells are prone to generate primitive, undifferentiated tumors in engrafted human fetal tissues in severe combined immunodeficient mice. Stem Cells Dev. Dec. 2007;16(6):893-902.

Soto-Gutierrez et al., Differentiation of human embryonic stem cells to hepatocytes using deleted variant of HGF and poly-amino-urethane-coated nonwoven polytetrafluoroethylene fabric. Cell Transplant. 2006;15(4):335-41.

Spagnoli et al., Guiding embryonic stem cells towards differentiation: lessons from molecular embryology. Curr Opin Genet Dev. Oct. 2006;16(5):469-75. Epub Aug. 17, 2006.

West et al., In vitro gametogenesis from embryonic stem cells. Curr Opin Cell Biol. Dec. 2004;16(6):688-92.

Wolff et al., Microelectrode measurements of pericellular $pO_2$ in erythropoietin-producing human hepatoma cell cultures. Am J Physiol. Nov. 1993;265(5 Pt 1):C1266-70.

Xu et al., BMP4 initiates human embryonic stem cell differentiation to trophoblast. Nat Biotechnol. Dec. 2002;20(12):1261-4. Epub Nov. 11, 2002.

\* cited by examiner

METHODS AND COMPOSITIONS FOR ENHANCED DIFFERENTIATION FROM EMBRYONIC STEM CELLS

RELATED APPLICATIONS

This application is a national stage filing under 35 U.S.C. §371 of International application PCT/US2008/007459, filed Jun. 13, 2008, which was published under PCT Article 21(2) in English, and claims the benefit under 35 U.S.C. §119(e) of U.S. provisional application Ser. No. 60/934,742 filed Jun. 15, 2007 and Ser. No. 61/125,041 filed Apr. 22, 2008, the entire contents of each of which are incorporated by reference herein.

GOVERNMENT SUPPORT

This invention was made in part with government support under grant number RO1-DK063108-01A1, DK063108-03, and NCRR ICR U4Z 16606 from the National Institutes of Health (NIH). The government has certain rights in this invention.

BACKGROUND OF THE INVENTION

The discovery and ability to isolate pluripotent stem cells that can give rise to mesoderm, endoderm and ectoderm lineages provides one foundation for emerging field of regenerative medicine. One of the first pluripotent stem cells of this type to be discovered and isolated is the embryonic stem (ES) cell. ES cells are cells derived from embryos, including human embryos, that are able to differentiate into the mesoderm, endoderm and ectoderm lineages under the proper conditions. The pluripotent nature of these cells makes them attractive candidates for cellular and/or tissue based regenerative medicine therapies. However there is much ongoing work relating to how best to differentiate these cells, reproducibly and efficiently into one or more desired lineages. Cell lineages and/or tissues generated and/or engineered from ES cells have utility both in vivo, for example in a transplant setting to replace a defective or non-existent cell lineage or tissue, and in vitro, for example as a research tool for screening candidate therapeutic agents.

As an example, differentiation of ES cells into cardiomyocytes would have great clinical significance. Transplantation of cardiomyocytes could be used in the treatment of cardiovascular disease. The major obstacle to cardiomyocyte transplant however is the need for donor cells and/or tissue which can only be gotten by organ donation. Thus, there is always a shortage of such cells.

Cardiomyocytes have been generated from ES cells. Analysis of gene expression profiles during ES cell differentiation in vitro suggests that the this process recapitulates cardiomyocyte development in vivo. ES cell derived cardiomyocytes when introduced into infracted hearts in animal models were able to survive, fuse with surrounding tissue, and be retained in the host. ES cell derived cardiomyocytes would therefore be ideal candidates for clinical transplantation therapy, provided sufficient numbers of these cells could be produced.

SUMMARY OF THE INVENTION

The invention relates broadly to a novel and surprising methodology for differentiating pluripotent stem cells including but not limited to ES cells. This methodology relates to modulating oxygen levels during pluripotent stem cell culture and differentiation, and this is exemplified herein in a non-limiting manner by the culture and differentiation of ES cells. The methods provided herein involve the culture of pluripotent stem cells such as ES cells at low oxygen at least for an initial period. In some embodiments this is followed by an increase in oxygen. In other embodiments, the cells remain at low oxygen throughout the entire culture period. In still other embodiments, the oxygen level may be increased and/or decreased during the culture period.

It has been found according to the invention that these low oxygen cultures are able to drive differentiation of pluripotent stem cells such as ES cells toward mesoderm and endoderm lineages. These differentiation protocols may be performed in the absence of exogenously added, usually costly, growth factors and/or other differentiation factors that have been reported in the art to be useful for driving differentiation from the pluripotent stem cell such as the ES cell stage towards mesoderm and endoderm lineages. The invention however contemplates the differentiation of pluripotent stem cells such as ES cells in the combined presence of low oxygen conditions and growth factors and/or other differentiation factors that induce differentiation towards the mesoderm and/or endoderm lineages. Such combined protocols would in some instances result in synergistic effects.

It has also been found that, in the presence of low oxygen, the timing and magnitude of gene expression during differentiation towards mesoderm, endoderm and ectoderm lineages may change, thereby providing in some instances a larger window of time during which differentiating cells, including multilineage or unilineage progenitors (or precursors, as the terms are used interchangeably herein), may be harvested and/or isolated and differentiation as a whole may be manipulated and/or influenced. The invention therefore provides, inter alia, methods for differentiating pluripotent stem cells such as ES cells through oxygen modulation, cell populations derived by such methods, and articles of manufacture that are useful in this regard.

In exemplary non-limiting embodiments, the invention demonstrates the ability to differentiate ES cells into cardiomyocytes through the modulation of oxygen during culture. As described in greater detail in the Examples, increased numbers of cardiomyocyte progenitors and cardiomyocytes are generated from ES cells in response to low oxygen culture conditions. In some embodiments, these cells are produced in the absence of exogenously added growth factors or other agents that are known to stimulate ES cells to commit to the cardiac lineage and/or to differentiate into cardiomyocytes. The invention is however not so limited as it contemplates the combined use of low oxygen and such factors, resulting in some instances in synergistic effects.

To this end, the invention provides various culture conditions under which the oxygen partial pressure at the surface of cells in culture approximates the oxygen partial pressure of the gas phase within which the cells are cultured.

The invention further provides in various aspects methods for generating increased numbers of mesodermal and endodermal progenitors and more differentiated cells such as end stage cells of mesoderm and endoderm lineages, methods for generating cell populations enriched in such cells, and the cell populations themselves. The invention further provides in various aspects methods for generating increased numbers of cardiomyocyte progenitors and cardiomyocytes from pluripotent stem cells such as ES cells, methods for generating cultured cell populations enriched in cardiomyocyte progenitors and/or cardiomyocytes, and the cell populations themselves.

More specifically, the invention provides a method for enhancing differentiation of pluripotent stem cells such as ES cells into mesoderm and/or endoderm lineages, thereby producing and/or enriching mesoderm and/or endoderm progenitors or end stage cells. This is accomplished by culturing pluripotent stem cells such as ES cells at a first oxygen partial pressure that is less than the oxygen partial pressure in a normoxic culture condition. As used herein, a normoxic culture condition is the oxygen partial pressure of the gas phase in a typical humidified incubator. Typically, this gas phase includes $CO_2$ and the oxygen partial pressure is 142 mmHg. The method therefore comprises culturing pluripotent stem cells such as ES cells at an oxygen partial pressure that is less than 142 mmHg. In one embodiment, the culture period is at least 1 or 2 days. In one embodiment, the pluripotent stem cells such as ES cells are cultured for at least 3 days or at least 6 days.

In another aspect, the invention provides a method for enhancing endoderm differentiation from pluripotent stem cells such as ES cells comprising culturing pluripotent stem cells such as ES cells at an oxygen partial pressure that is less than 142 mmHg. In one embodiment, the culture period is at least 1 or 2 days. In one embodiment, the pluripotent stem cells such as ES cells are cultured for at least 3 days or at least 6 days.

In another aspect, the invention provides a method for enhancing hematopoietic differentiation of pluripotent stem cells comprising culturing pluripotent stem cells in low oxygen partial pressure for a time period sufficient to generate hematopoietic cells. In one embodiment, the pluripotent stem cells are ES cells. In one embodiment, the hematopoietic cells are red blood cells. In one embodiment, the low oxygen partial pressure is between 0-80 mmHg.

In a related aspect the invention provides a method for producing or enriching cardiomyocyte progenitors and/or cardiomyocytes comprising performing a first culture step comprising culturing pluripotent stem cells such as ES cells at a first oxygen partial pressure that is less than 142 mmHg.

It has been shown according to the invention that culture of pluripotent stem cells such as ES cells at a constant low oxygen partial pressure (e.g., at 7 mmHg or 36 mmHg) results in for example greater cardiomyocyte output as compared to culture at 142 mmHg. Thus in some embodiments the oxygen partial pressure remains low (e.g., lower than 142 mmHg, and in some instances at a constant oxygen partial pressure) throughout the culture period. The first oxygen partial pressure may be less than 50 mmHg, less than 40 mmHg, less than 30 mmHg, less than 20 mmHg, less than 10 mmHg, or 0 mmHg. The first oxygen partial pressure may be about 1, 2, 3, 4, 5, 6, 7, 8, 9, 10, 11, 12, 13, 14, 15, 16, 17, 18, 19, 20, 22, 22, 23, 24, 25, 26, 27, 28, 29, 30, 31, 32, 33, 34, 35, 36, 37, 38, 39, 40, 41, 42, 43, 44, 45, 46, 47, 48, 49, 50 mmHg or higher. In one embodiment the first oxygen partial pressure is about 7 mmHg, while in another it is about 36 mmHg.

It has been further found according to the invention that culture of pluripotent stem cells such as ES cells under variable oxygen partial pressure (e.g., starting at 36 mmHg and increasing to 142 mmHg or starting at 7 mmHg and increasing to 142 mmHg) results in for example greater cardiomyocyte output as compared to culture at 142 mmHg. Thus in some embodiments the first culture step is followed by a second culture step at a second oxygen partial pressure that is greater than the first oxygen partial pressure. The second oxygen partial pressure may be at least 80 mmHg, at least 100 mmHg, at least 120 mmHg, or at least 135 mmHg, at least 150 mmHg, at least 170 mmHg, or at least 200 mmHg. The second oxygen partial pressure may be 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120 mmHg or lower. In one embodiment the second oxygen partial pressure is about 142 mmHg.

The low oxygen culture step is generally referred to herein as the first culture step regardless of whether oxygen level is later increased, and the higher oxygen culture step is generally referred to herein as the second culture step.

In some embodiments, there may be additional modulation of oxygen levels between the initial low oxygen partial pressure condition and the ultimate higher oxygen partial pressure condition. For instance, the oxygen partial pressure may initially be low, then increased, then decreased, and then finally increased again to a level that is greater than the initial oxygen partial pressure. Alternatively, it may be low, and then increased incrementally or continuously until it reaches a desired oxygen partial pressure that is greater than the initial oxygen partial pressure.

In some embodiments the first culture step occurs for a first period of time of about 1-8 days. The first time period may be 2-8 days, 4-6 days, or 5-7 days. The first time period may be 1, 2, 3, 4, 5, 6, 7, 8, or more days. In one embodiment, the first time period is 6 days. In this and other embodiments, the second culture step occurs for a second period of time of about 1-20 days, 2-20 days, 5-20 days, 10-20 days, or 12 to 18 days. The second time period may be 1, 2, 3, 4, 5, 6, 7, 8, 9, 10, 11, 12, 13, 14, 15, 16, 17, 18, 19, 20 or more days. The second time period may be 15 days. In another embodiment, the first time period and the second time period total to at least 10 days, at least 15 days, or at least 20 days. In one embodiment, the first time period and the second time period total to 21 days.

In another embodiment, the first and second culturing steps are performed in one culture vessel. In still another embodiment, the second culturing step is performed in the absence of serum (e.g., in defined serum-free medium). In other embodiments, the first and second culturing steps are performed in the presence of serum, although the invention is not to be limited in this regard. In some embodiments, the serum level increases from the first to the second culturing steps.

In another aspect, the invention provides a method for enhancing cardiomyocyte production comprising culturing pluripotent stem cells such as ES cells at an oxygen partial pressure that is less than 142 mmHg for at least 10 days.

In certain embodiments, the oxygen partial pressure is less than 50 mmHg, less than 40 mmHg, less than 30 mmHg, less than 20 mmHg, less than 10 mmHg, or 0 mmHg. The oxygen partial pressure may be about 1, 2, 3, 4, 5, 6, 7, 8, 9, 10, 11, 12, 13, 14, 15, 16, 17, 18, 19, 20, 22, 22, 23, 24, 25, 26, 27, 28, 29, 30, 31, 32, 33, 34, 35, 36, 37, 38, 39, 40, 41, 42, 43, 44, 45, 46, 47, 48, 49, 50 mmHg or higher, provided that it is less than 142 mmHg. In one embodiment, the oxygen partial pressure is about 7 mmHg or about 36 mmHg.

In one embodiment, the cells are cultured for 11 days. In one embodiment, the cells are cultured in the absence of serum starting at day 5 or 6.

In yet another method, the invention provides a method for enhancing cardiomyocyte enrichment comprising culturing pluripotent stem cells such as ES cells at an oxygen partial pressure that is less than 50 mmHg for at least 10 days.

In certain embodiments, the oxygen partial pressure is less than 40 mmHg, less than 10 mmHg, or 0 mmHg.

In one embodiment, the cells are cultured for 11 days.

In various embodiments of these particular aspects of the invention, the oxygen partial pressure may be less than 50 mmHg, less than 40 mmHg, less than 10 mmHg, or 0 mmHg. In some embodiment, the oxygen partial pressure is about 7 mmHg or about 36 mmHg.

Various other embodiments apply equally to the aforementioned aspects of the invention, and these are recited below.

In various embodiments, the cultures are performed under conditions that control oxygen partial pressure, including conditions that control pO2cell to within 0-15 mmHg of pO2gas. These conditions include use of oxygen-permeable membranes such as but not limited to silicone rubber membranes.

In one embodiment, the pluripotent stem cells are ES cells. In one embodiment, the pluripotent stem cells such as ES cells are cultured on an oxygen-permeable membrane. The oxygen-permeable membrane may be an oxygen-permeable rubber membrane, such as a silicone rubber membrane. The oxygen-permeable membrane may be coated with an agent that promotes cell adhesion. The agent may be fibronectin, gelatin or laminin, or combinations thereof, although it is not so limited.

In one embodiment, the pluripotent stem cells such as ES cells are untransfected or transfected cells.

In one embodiment, the pluripotent stem cells such as ES cells are cultured in the presence or absence of exogenous factors including exogenous differentiating factors. Such factors include but are not limited to ascorbic acid and retinoic acid.

In various embodiments, the method may further comprise harvesting the progenitor and/or other differentiated cells such as terminally differentiated end stage cells produced in the cultures such as for example in some embodiments cardiomyocytes. The methods provided herein may be supplemented with any selection process or method such as a flow-based cell sorting (e.g., FACS) fractionation based on for example particular cell surface markers. Cells may be harvested from any stage of culture.

In some embodiments, the method produces about 110 cardiomyocytes per input pluripotent stem cell (e.g., ES cell). In other embodiments, the method produces about 300 cardiomyocytes per input pluripotent stem cell (e.g., ES cell). In some embodiments, the method produces a population of cells of which at least about 45% are cardiomyocytes. In some embodiments the population of cells harvested from the culture is about 50% cardiomyocytes and in other embodiments it is about 55% cardiomyocytes.

In still another aspect, the invention provides a composition comprising pluripotent stem cells such as ES cells in a culture medium within a culture vessel having an oxygen-permeable membrane. In one embodiment, the oxygen-permeable membrane is a silicone rubber membrane. The culture vessel in some embodiments has a recognizable bottom (i.e., the surface to which the cells generally rest and/or adhere while in culture) and that bottom comprises an oxygen-permeable membrane. In other embodiments, the oxygen-permeable membrane is physically separate from the culture vessel.

In still another aspect, the invention provides a method for controlling oxygen partial pressure of pluripotent stem cells such as ES cells in culture comprising culturing such cells in a liquid medium in contact with a gas phase, wherein oxygen partial pressure at the surface of the cells (if in a monolayer) or at the surface of a cell multilayer or an aggregate (if in a monolayer or an aggregate) is within 15 mmHg of $pO_{2gas}$. In one embodiment, $pO_{2cell}$ is within 15 mmHg, within 14 mmHg, within 13 mmHg, within 12 mmHg, within 11 mmHg, within 10 mmHg, within 9 mmHg, within 8 mmHg, within 7 mmHg, within 6 mmHg, within 5 mmHg, within 4 mmHg, within 3 mmHg, within 2 mmHg, or within 1 mmHg of $pO_{2gas}$, or it is equal to $pO_{2gas}$. In one embodiment, $pO_{2cell}$ is within 5 mmHg of $pO_{2gas}$. In one embodiment, the cells are cultured in a culture vessel having an oxygen-permeable membrane. In one embodiment, the oxygen-permeable membrane is a silicone rubber membrane.

In still another aspect, the invention provides methods for determining therapeutic efficacy or toxicity of a compound comprising exposing a differentiated cell population to the compound (e.g., contacting in vitro the differentiated cell population with the compound), and determining an effect of the compound on the differentiated cell population. The differentiated cell population is generated according to the foregoing methods in accordance with the invention. In one embodiment, the compound is an experimental compound. In related embodiments, the effect of the compound on a differentiated cell population is inhibition of proliferation, stimulation of proliferation, or toxicity.

These and other embodiments of the invention will be described in greater detail herein.

Each of the limitations of the invention can encompass various embodiments of the invention. It is therefore anticipated that each of the limitations of the invention involving any one element or combinations of elements can be included in each aspect of the invention. This invention is not limited in its application to the details of construction and/or the arrangement of components set forth in the following description or illustrated in the Figures. The invention is capable of other embodiments and of being practiced or of being carried out in various ways.

The phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

(A) Fraction of cells that were cardiomyocytes (top), total number of cells (middle), and total number of cardiomyocytes (bottom) for cells cultured at constant $pO_{2gas}$ conditions of 7, 36, or 142 mmHg for 11 days. The number fraction of cardiomyocytes was determined by flow cytometry of trypsin-dispersed cell samples immunostained with MF-20. Data shown as mean±s.d. for 7 independent experiments (at least 3 replicates per experiment), each started with 30 embryoid bodies (EBs)/well (0.15×10⁵ cells/well). P values were found using a two-tailed t-test for paired samples. MF-20 is a anti-sarcomeric myosin heavy chain antibody.

(B) Representative images of 5-μm tissue sections stained for MF-20 (brown) and counter stained with hematoxylin (scale bar=200 μm). Tissue was obtained after 11 days of differentiation from one of the experiments at each constant $pO_{2gas}$ condition that contributed to the data shown in (A).

The cells were removed and centrifuged into a pellet prior to sectioning, resulting in a random tissue orientation.

(C) Comparison of the number fraction of MF-20+ cells counted from immunostained 5-µm sections to that measured with flow cytometry of trypsin-dispersed cells (mean±s.d., n=3). Open, grey filled, and black filled symbols represent samples taken from $pO_{2gas}$ of 142, 36, and 7 mmHg, respectively, and each shape (circle, triangle, upside-down triangle) represents an independent experiment.

Figure 2:
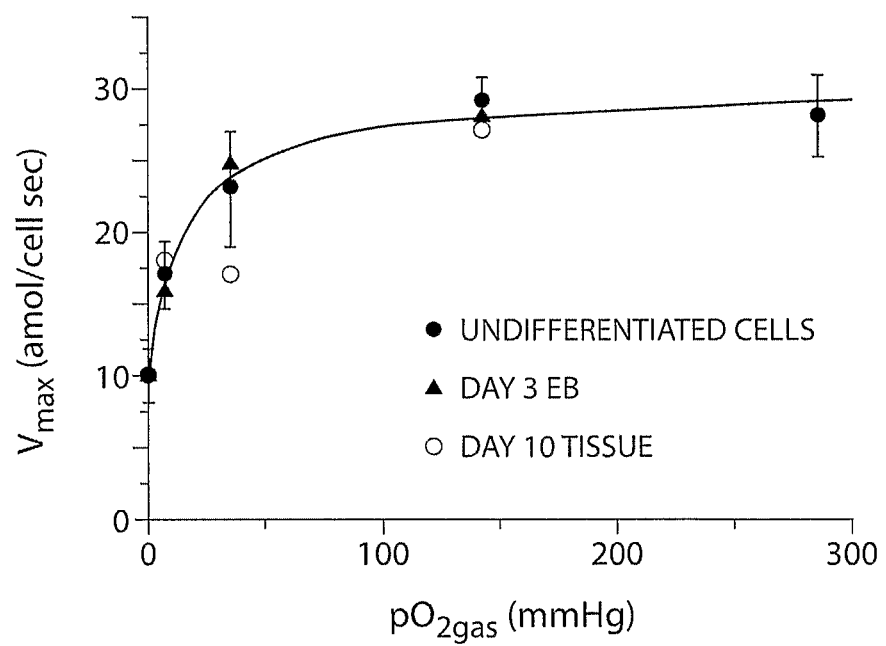

FIG. 2. Dependence of Vmax on $pO_{2gas}$ at which cells were cultured. The maximal normoxic OCR (Vmax) of undifferentiated mES cells (closed circles), day 3 EBs (triangles), and day 10 tissue (open circles) is shown as a function of the culture $pO_{2gas}$. The fit of these data using Eqn. (3) is also shown. Data for Vmax with undifferentiated ES cells are reported as mean±s.d. for at least 4 independent experiments, and data for differentiating cells are from single experiments.

Figure 3:
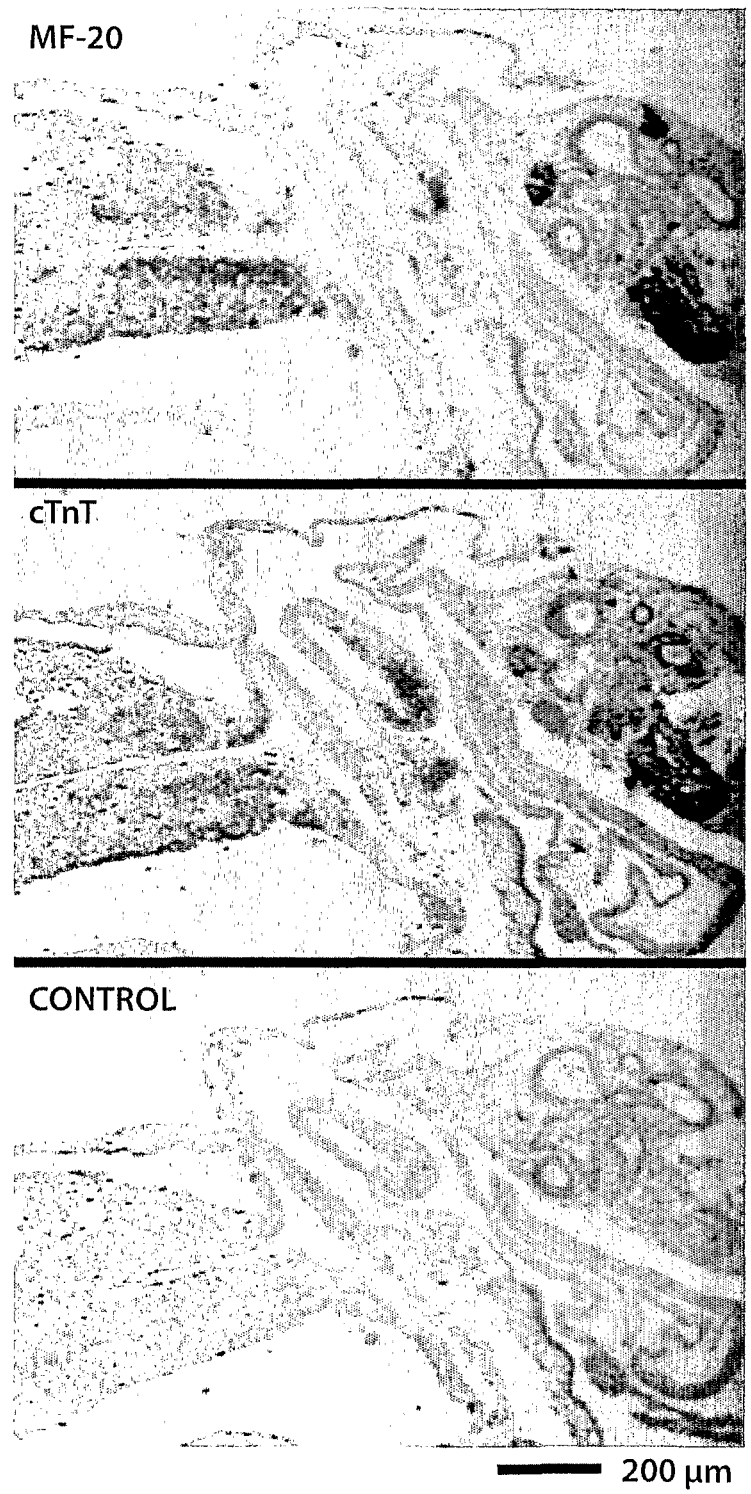

FIG. 3. Co-localization of MF-20 and cTnT immunostaining. Consecutive 5-im tissue sections immunostained with MF-20 (top) or cardiac troponin T (cTnT—middle), or no primary antibody (control—bottom). Images shown are from a sample cultured at 36 mmHg, but are representative of the co-localization of MF-20 and cTnT observed in day 11 tissue sections from all $pO_{2gas}$ conditions.

Figure 4:
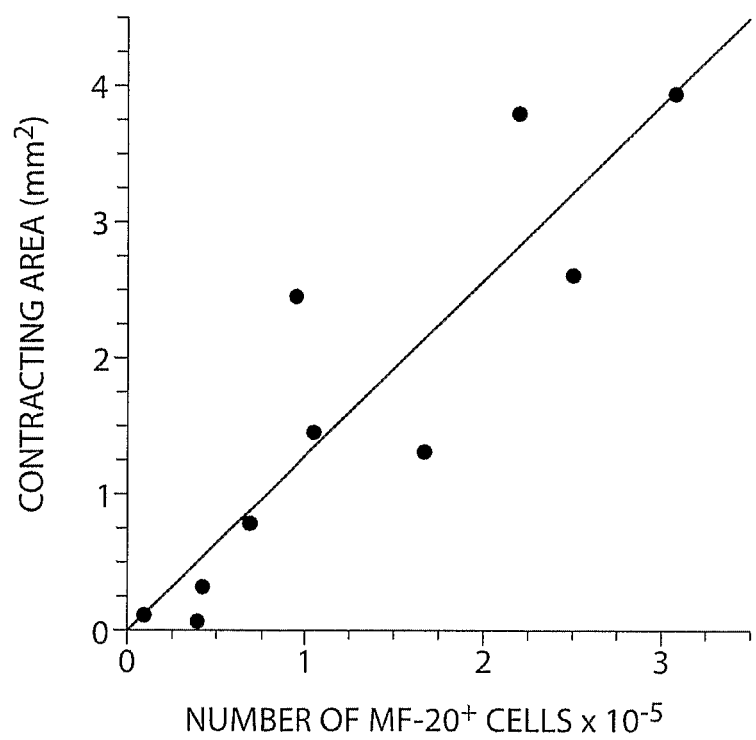

FIG. 4. Immunostaining with MF-20 correlates with spontaneous contraction. Comparison between the total number of cells that bind to a primary antibody to sarcomeric myosin heavy chain (MF-20-positive cells) counted using flow cytometry and the total surface area of the culture dish covered with spontaneously contracting cells estimated visually. The fraction of MF-20 positive cells ranged from 3 to 36% in these samples. The best-fit line was determined using linear regression; R2=0.80.

Figure 5:
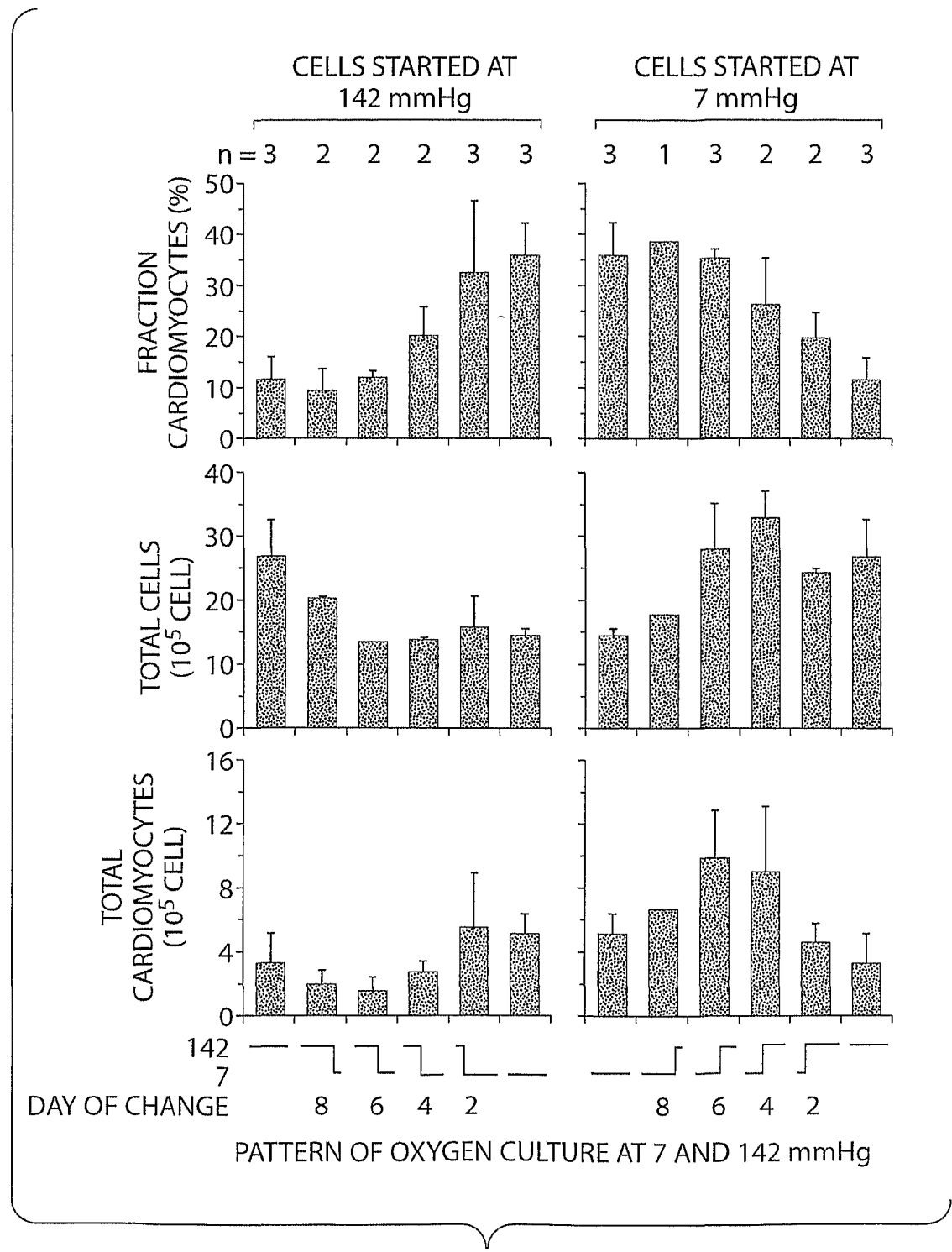

FIG. 5. Temporal modulation of $pO_{2gas}$ affects differentiation. Fraction of cells that were cardiomyocytes, total number of cells, and total number of cardiomyocytes as determined by flow cytometry of trypsin-dispersed cell samples immunostained with MF-20 after 10 days of differentiation. Cells were started at either 142 or 7 mmHg and then switched to the other condition on day 2, 4, 6, 8, or not at all. The 10 different experimental $pO_{2gas}$ histories are shown at the bottom of the Figure, and the day of change of the $pO_{2gas}$ is noted. The number of independent experiments (n), each with three replicates, is given at the top of each column. Data are mean of the results of the independent experiments±s.d. where n=3, or ±range where n=2.

Figure 6:
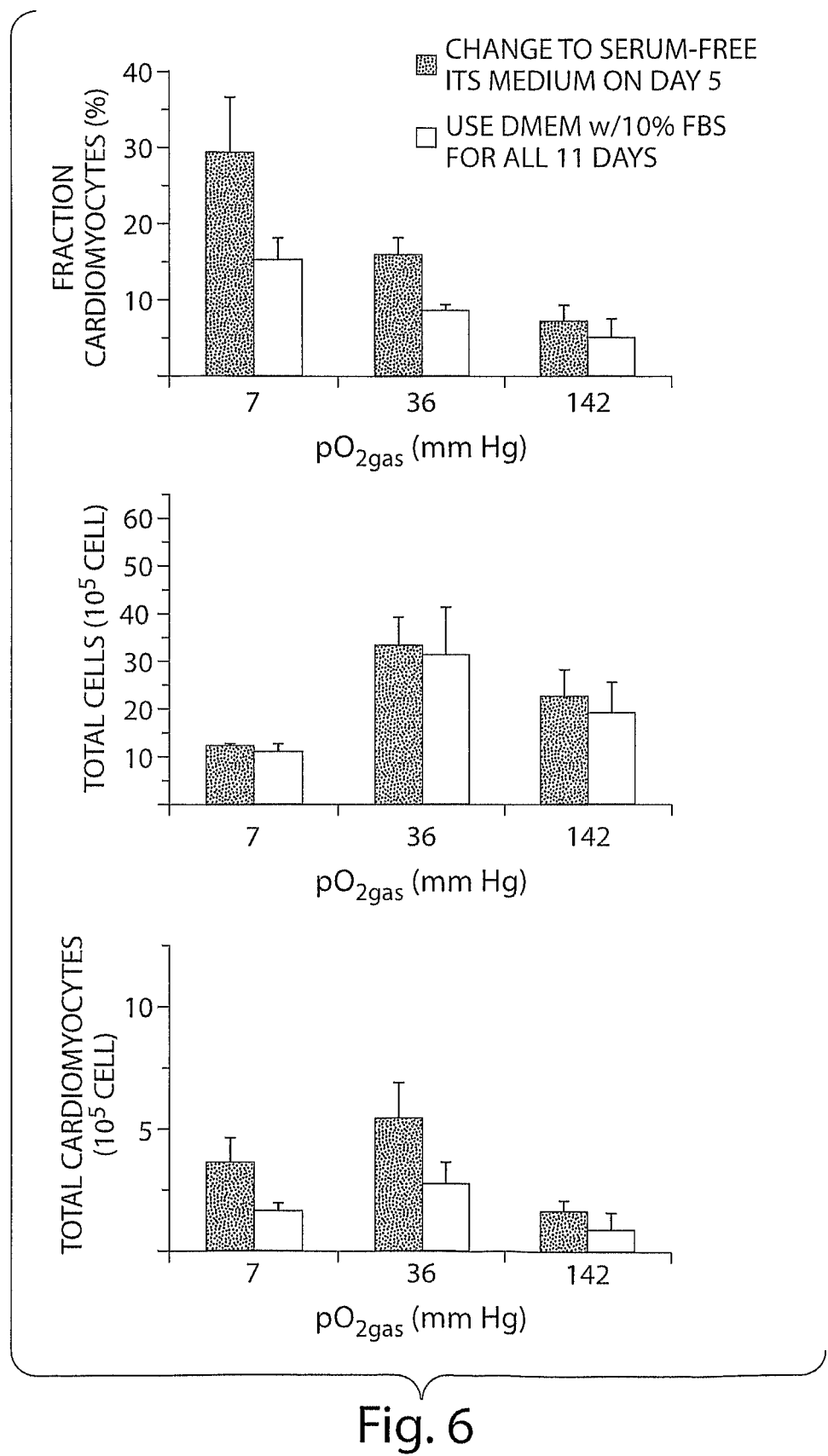

FIG. 6. Enhanced cardiomyogenesis in serum-free medium. Fraction of cells that were cardiomyocytes (top), total number of cells (middle), and total number of cardiomyocytes (bottom) for cells cultured at constant $pO_{2gas}$ conditions of 7, 36, or 142 mmHg for 11 days. Cells were maintained in serum containing DMEM for all 11 days (open bars) or were changed to a serum-free ITS medium after 5 days (solid bars). The number fraction of cardiomyocytes was determined by flow cytometry of trypsin-dispersed cell samples immunostained with MF-20. Data shown as mean±s.d. for 3 replicate wells in a single experiment.

Figure 7:
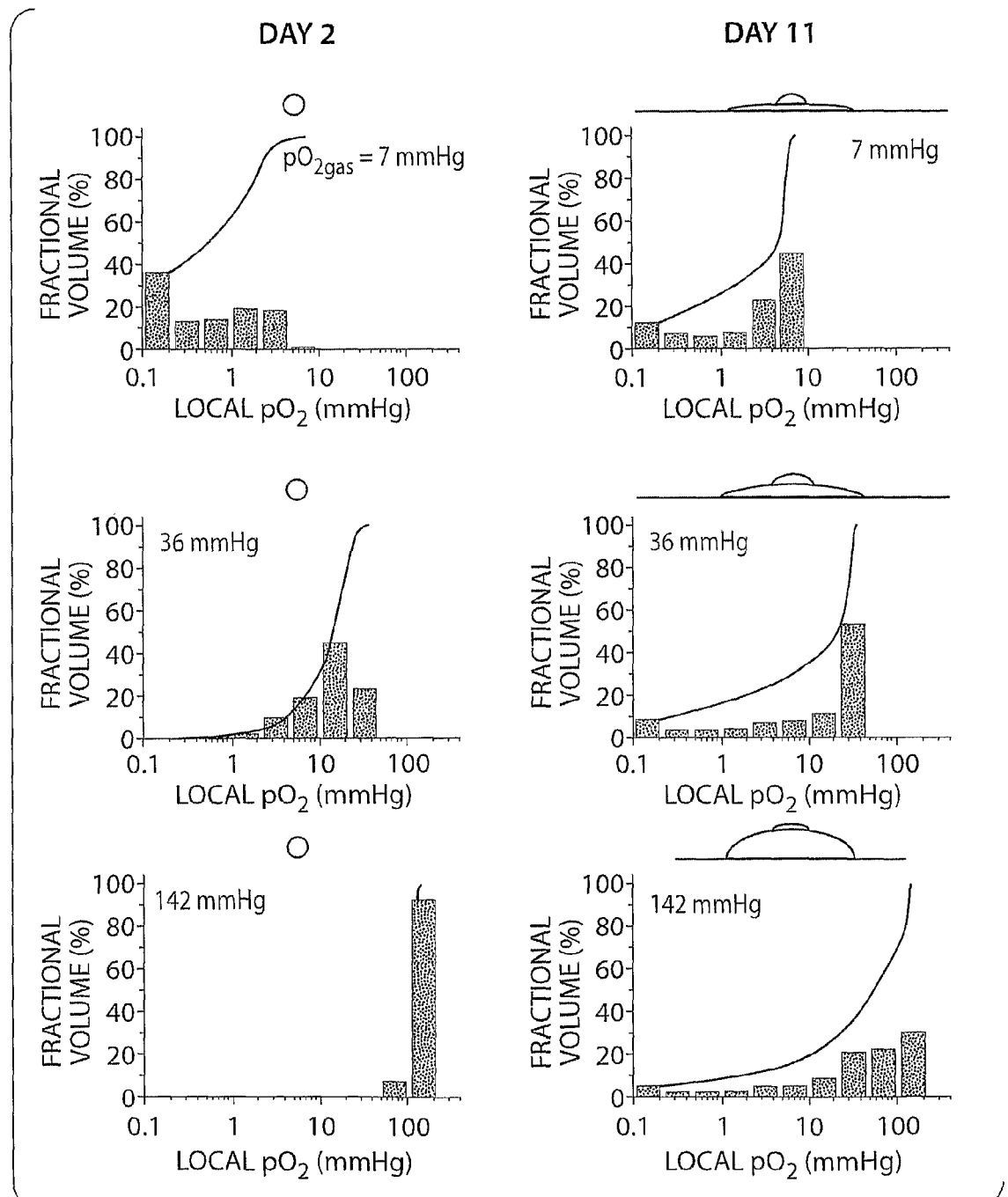

FIG. 7. Volumetric distribution of $pO_2$ values within differentiating cellular aggregates. A theoretical mathematical model for oxygen consumption and diffusion in the cellular aggregates was solved numerically to yield profiles of $pO_{2cell}$ within the tissue. Tissues were assumed to have uniform cell distributions and material properties. After 2 days of culture using the hanging drop method, EBs were nearly perfect spheres and were transferred to fibronectin-coated silicone rubber surfaces, to which they attached and spread. The dimensions of the aggregates after 11 days in culture were measured, and an aggregate with the median length and height at each condition is drawn to scale above each panel. The line represents the cumulative volume fraction of tissue exposed to a $pO_2$ less than or equal to the indicated value. Each solid bar represents the fraction of the total volume of tissue within the aggregate that is exposed to a specific range of $pO_{2cell}$. These $pO_{2cell}$ ranges span values of 1-2, 2-5, or 5-10 within each decade on a logarithmic scale.

Figure 8:
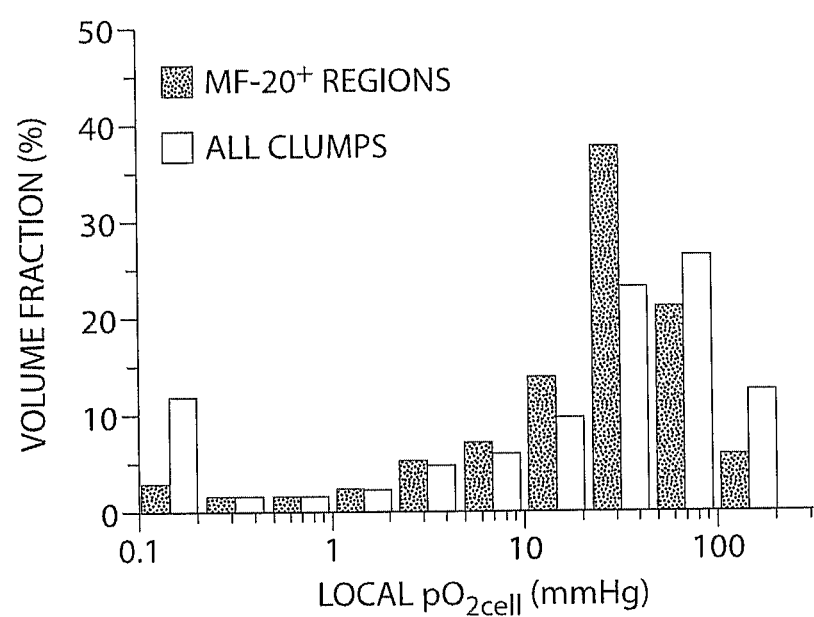

FIG. 8. Volumetric distribution of $pO_2$ values in MF-20+ regions of cellular aggregates. The filled bars represent the distribution of $pO_2$ within regions positively immunostained with MF-20, which accounted for approximately 10% of the total tissue volume, and the open bars represent the distribution of $pO_2$ in the entire aggregate volume in the culture dish (including MF-20+ regions) for tissue cultured at a $pO_{2gas}$ of 142 mmHg. The cell sheet morphology was excluded from this analysis because it contained no MF-20+ cells at any $pO_{2gas}$.

Figure 9:
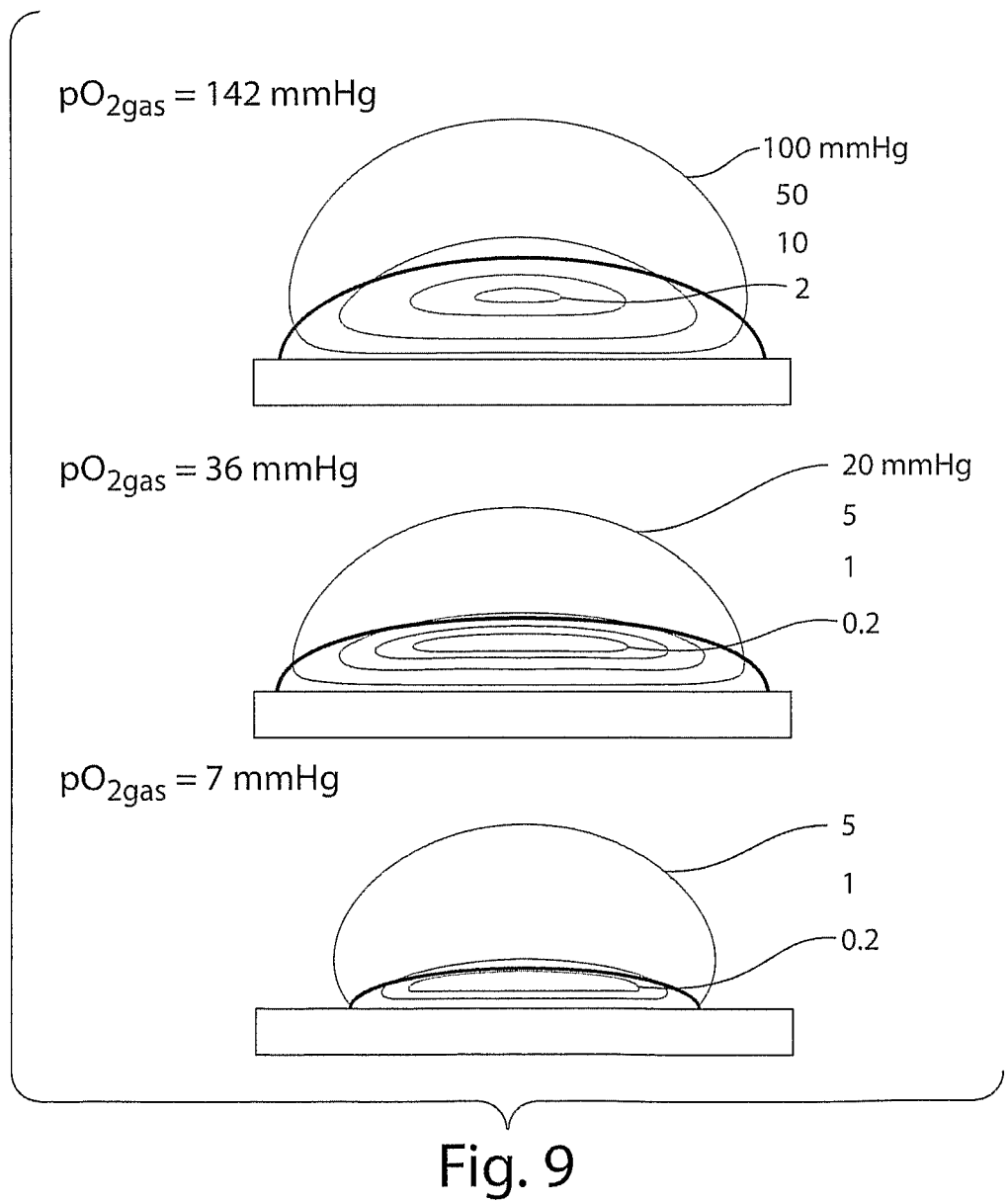

FIG. 9. $pO_2$ profiles in day 11 aggregates. Lines of constant $pO_2$ are plotted for day 11 aggregates at $pO_{2gas}$ of 142, 36, and 7 mmHg. The number to the right of each shape correspond to the $pO_2$ values for which contour lines are plotted. The aggregate shown has the mean dimensions from Table 3 and is representative of the profiles observed in aggregates with different sizes.

Figure 10:
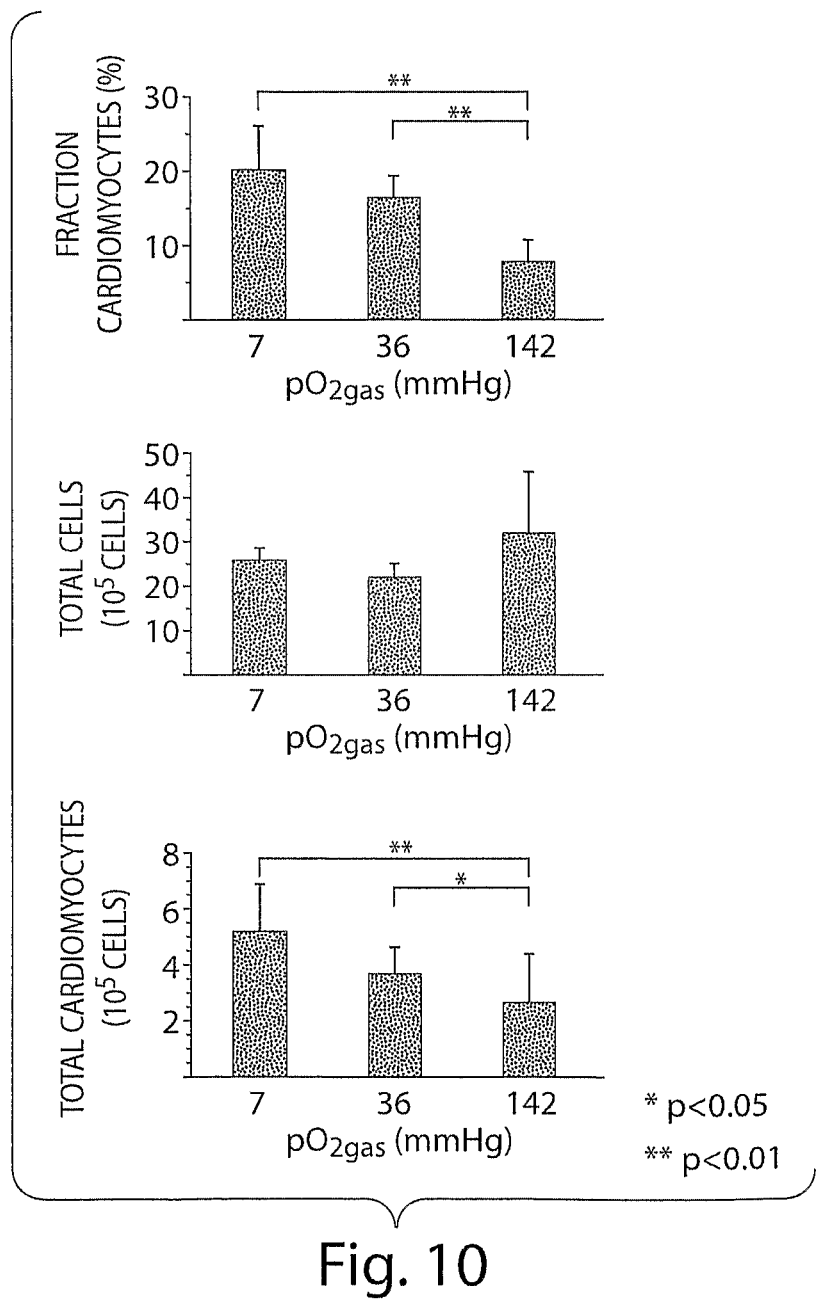

FIG. 10. Differentiation into cardiomyocytes in the absence of ascorbic acid. Fraction of cells that were cardiomyocytes, total number of cells, and total number of cardiomyocytes as determined by flow cytometry of trypsin-dispersed cell samples immunostained with MF-20 after 10 days of differentiation.

Figure 11:
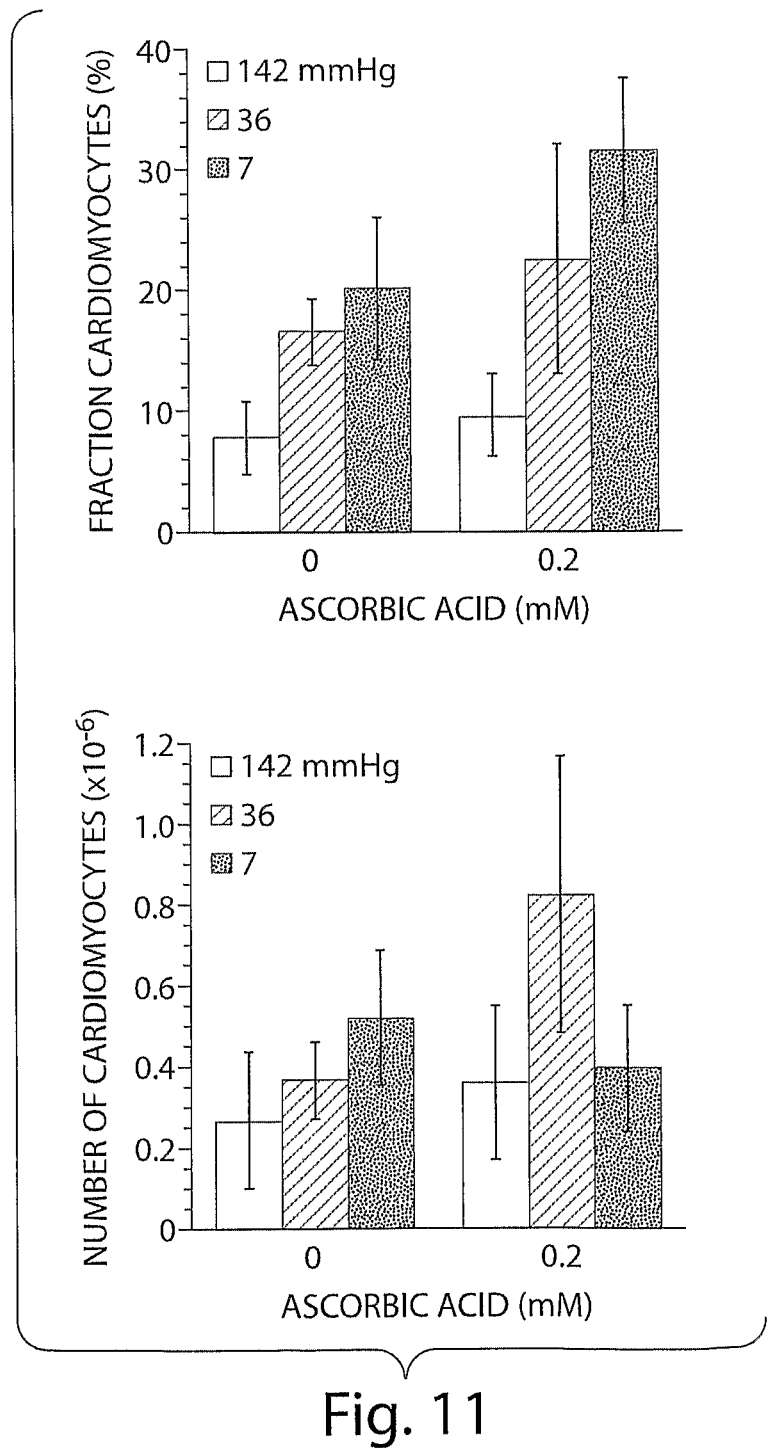

FIG. 11. Low oxygen and ascorbic acid synergistically increased cardiomyocyte yield. The Figure shows flow cytometric data from mES cells differentiated for 11 days at 142, 36 and 7 mmHg $pO_2$ in the presence and absence of ascorbic acid, and then stained with MF-20 antibody.

Figure 12:
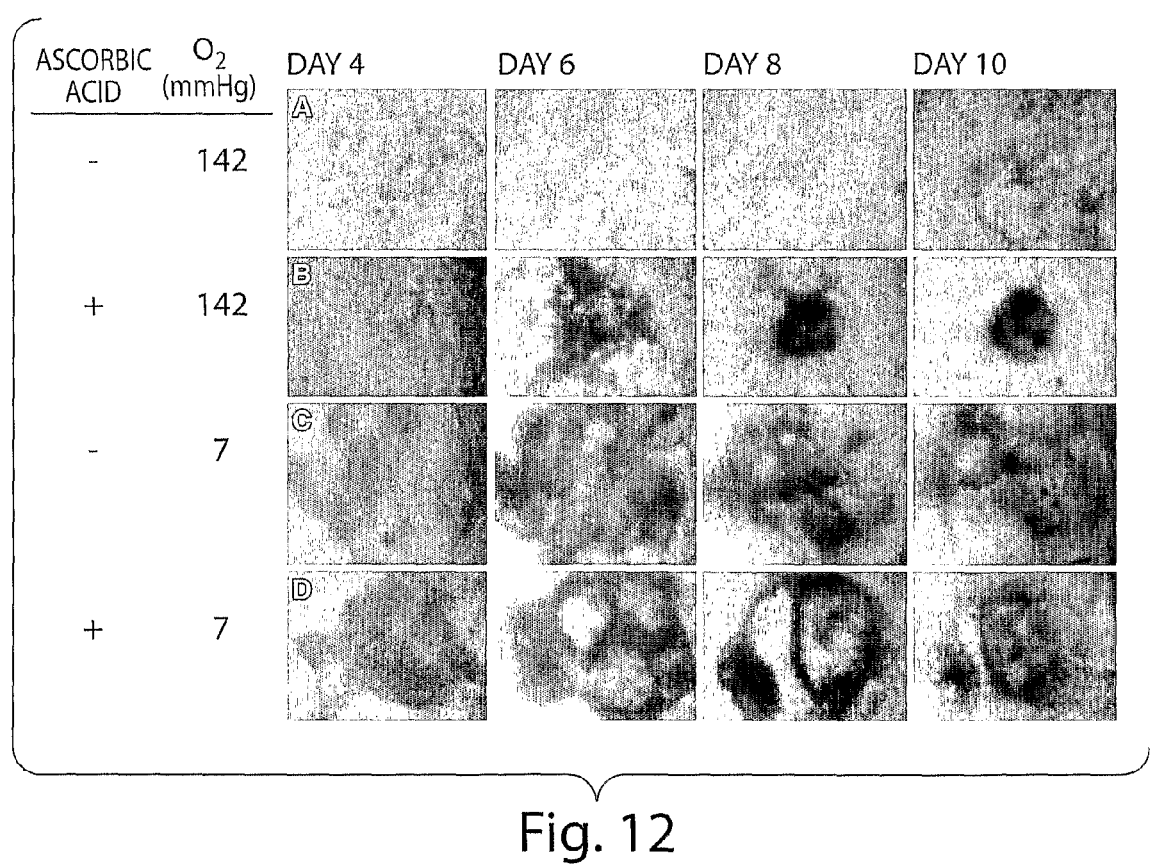

FIG. 12. EB morphology in the presence or absence of ascorbic acid. Micrographs of EBs attached to a silicone rubber surface showing morphological differences during differentiation on days 4, 6, 8, and 10. One EB was placed per well in a 48-well plate with the bottom replaced with silicone rubber and differentiated for 10 days at $pO_{2gas}$ of 142 or 7 mmHg with or without 0.2 mM ascorbic acid.

Figure 13:
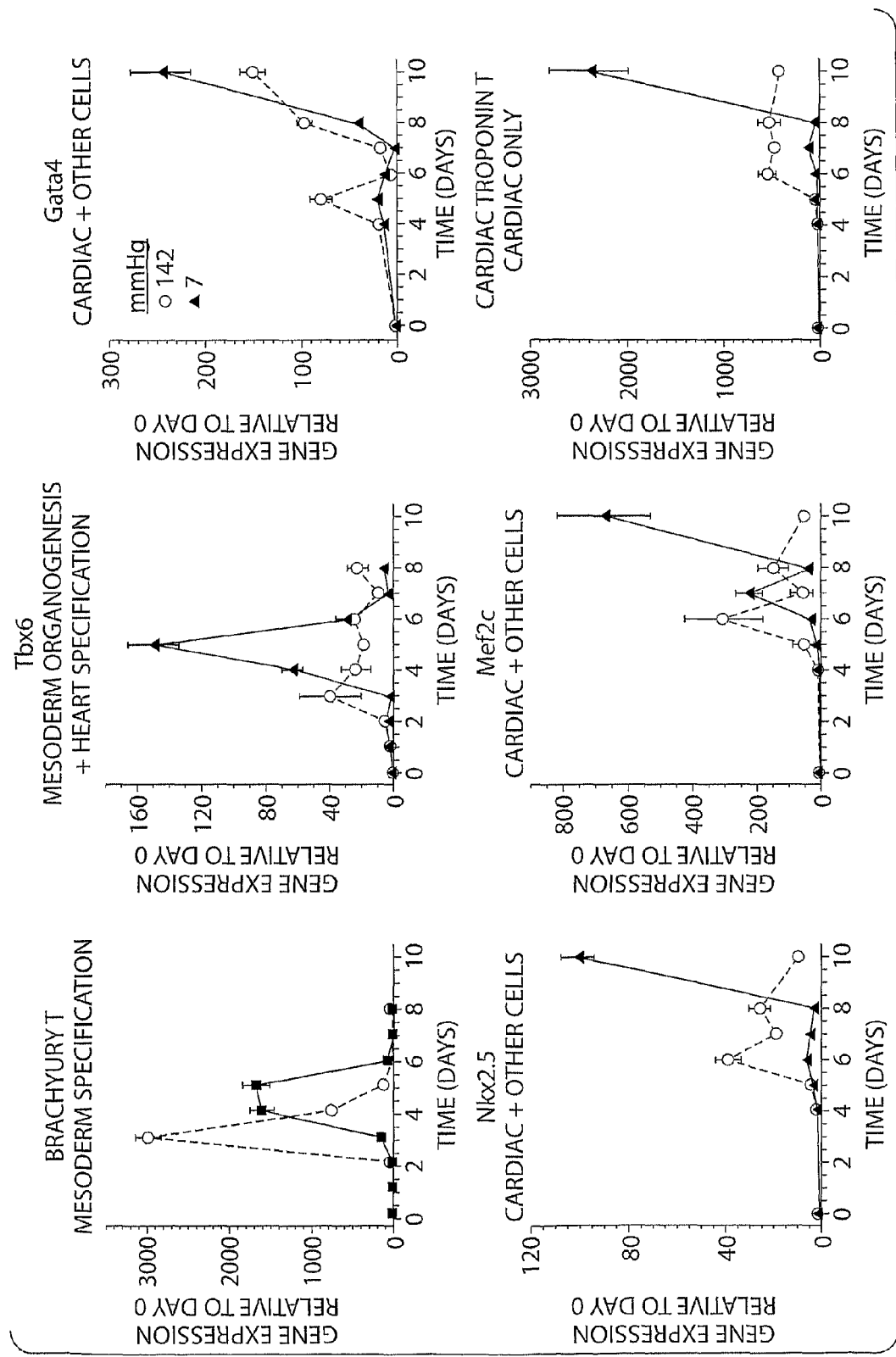

FIG. 13. Low oxygen differentiation of mES cells delay and magnify expression of mesodermal cardiac markers. Temporal gene expression levels of mesodermal cardiac markers Tbx6, Gata4, Nkx2.5, Mef2c, and cTnT obtained by qPCR on days 0 to 10 for mES cells differentiated at 142 and 7 mmHg $pO_2$. Differentiation at 7 mmHg $pO_{2gas}$ resulted in delayed expression of Tbx6 at day 3 relative to 142 mmHg, but very high levels of expression were observed after 4 and 5 days of differentiation. The expression of cardiac genes Gata4, Nkx2.5, Mef2c, and Cardiac Troponin T (cTnT) was also delayed at early time points at 7 mmHg $pO_{2gas}$, but was much higher at 7 mmHg than 142 mmHg by day 10, in parallel to the fraction and number of cardiomyocyte observed.

Figure 14:
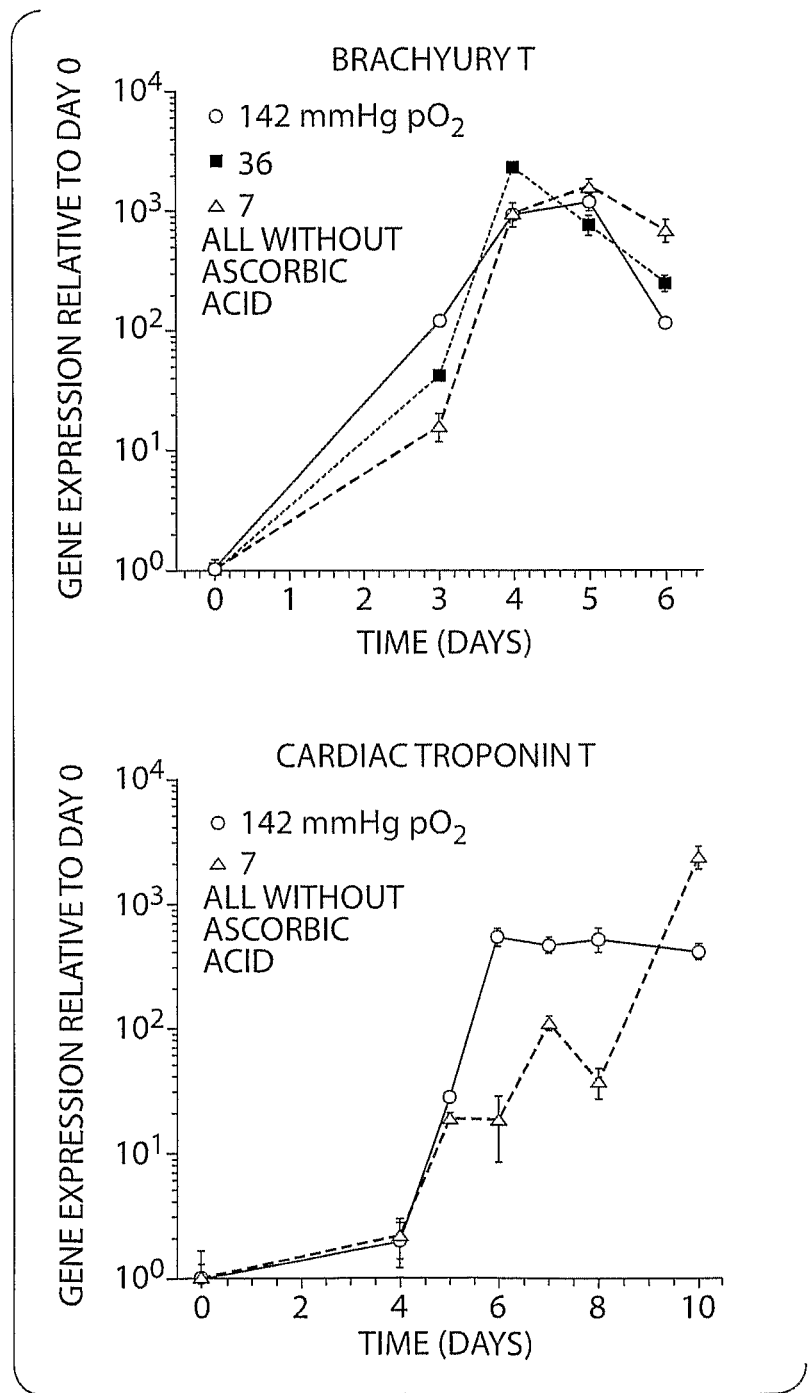

FIG. 14. Low oxygen differentiation of mES cells delay and magnify Brachyury T and cardiac Troponin T expression. Data for Brachyury T and cardiac Troponin T generated and shown in FIG. 13 are replotted on this Figure on a semi log scale.

Figure 15:
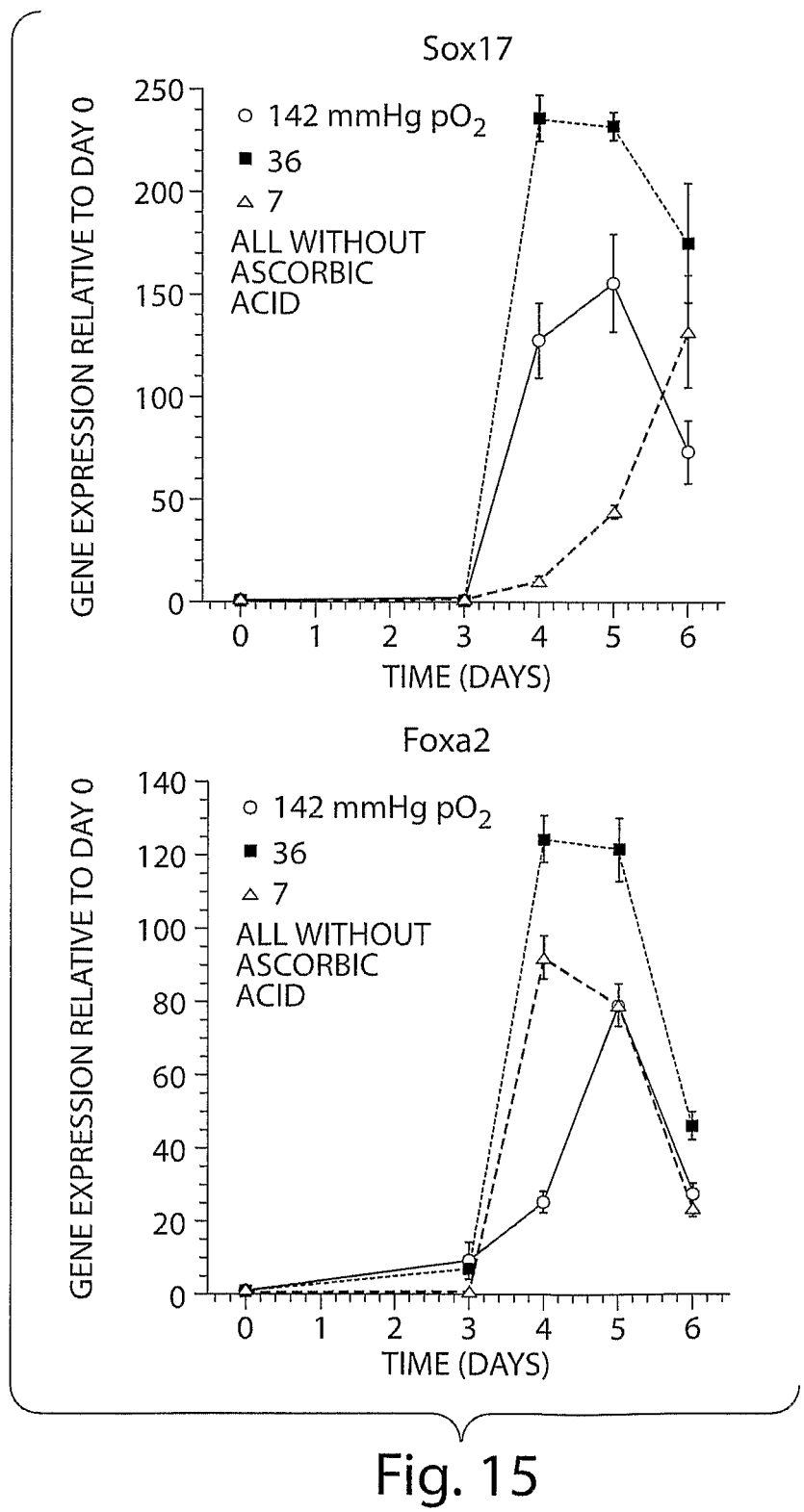

FIG. 15. Control of oxygen influences definitive endoderm gene expression. The Figure shows real-time PCR results of Sox17 and Foxa2 expression for mES cells differentiated for 6 days at 142, 36 and 7 mmHg $pO_2$. Sox17 and Foxa2 are transcription factors involved in definitive endoderm development.

Figure 16:
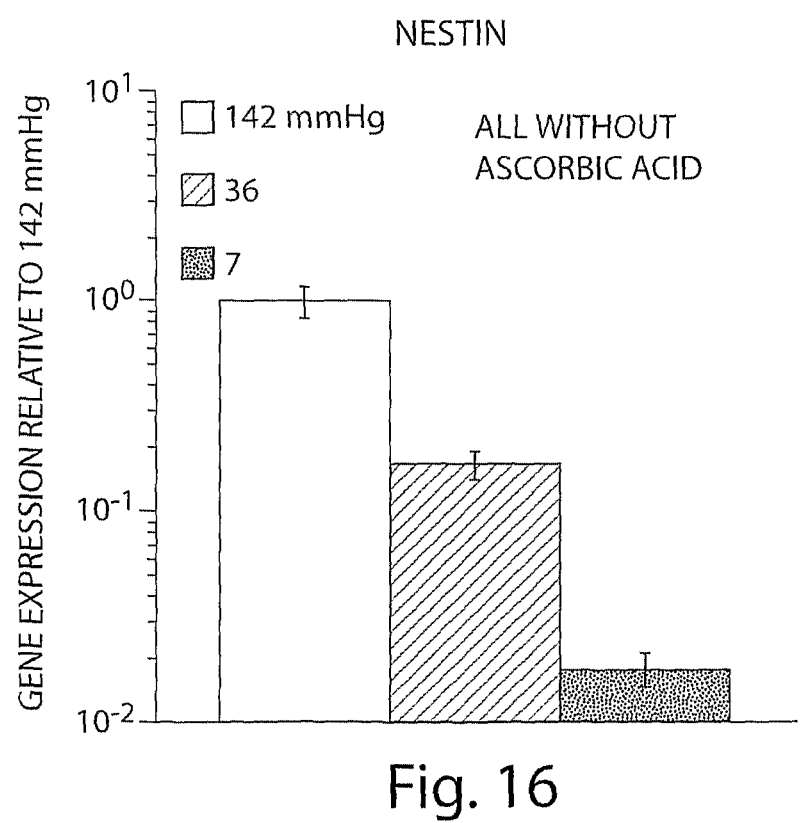

FIG. 16. Low oxygen decreases ectoderm expression. The Figure shows real-time PCR results of Nestin expression for mES cells differentiated for 10 days at 142, 36 and 7 mmHg $pO_2$. Nestin is a neural filament protein and an ectoderm marker. Reduced oxygen for 10 days appears to decrease ectoderm gene expression.

Figure 17:
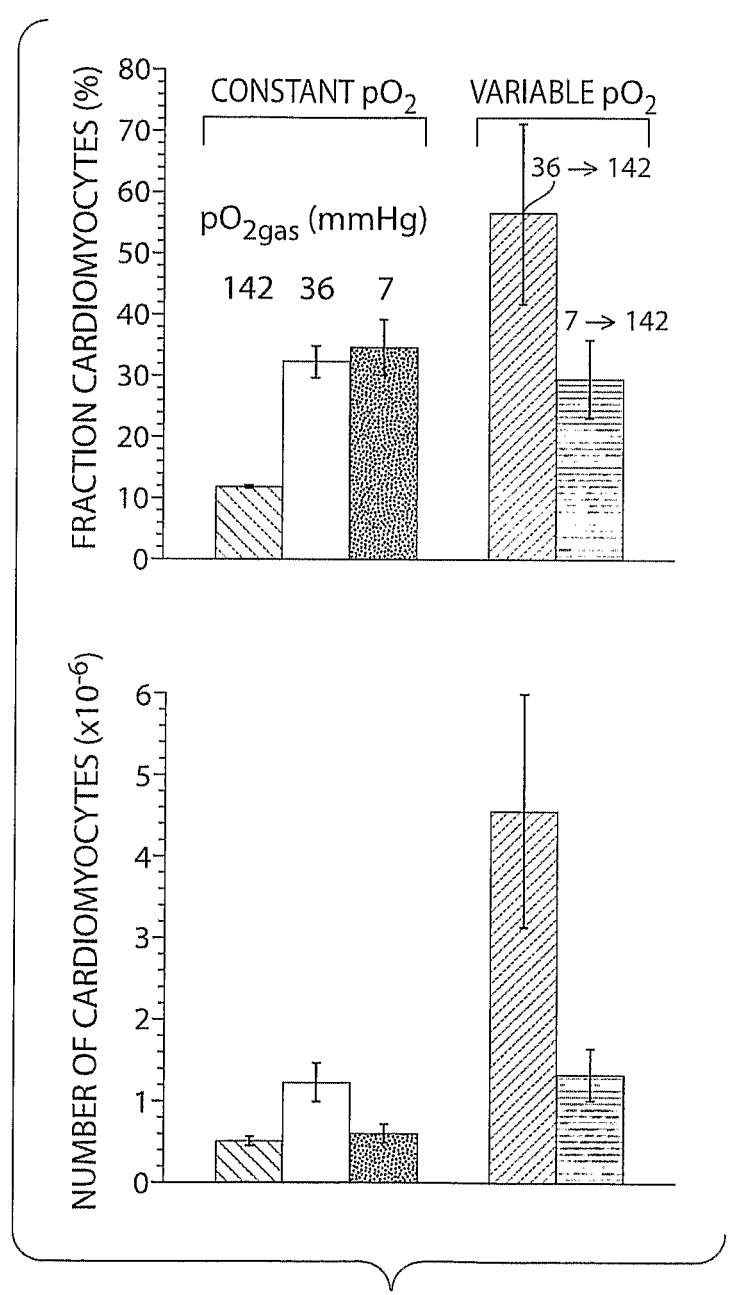

FIG. 17. Temporal modulation of $pO_{2gas}$ from 36 to 142 mmHg maximized yield of cardiomyocytes. Fraction and total number of cardiomyocytes were determined by flow cytometry of MF-20-stained, trypsin-dispersed cell samples after 21 days of differentiation. Cells were cultured with 0.2 mM ascorbic acid at constant 142, 36, or 7 mmHg or first cultured for 36 or 7 mmHg for 7 days, then switched to 142 mmHg for 15 days. All data are mean±SD from n=3.

Figure 18:
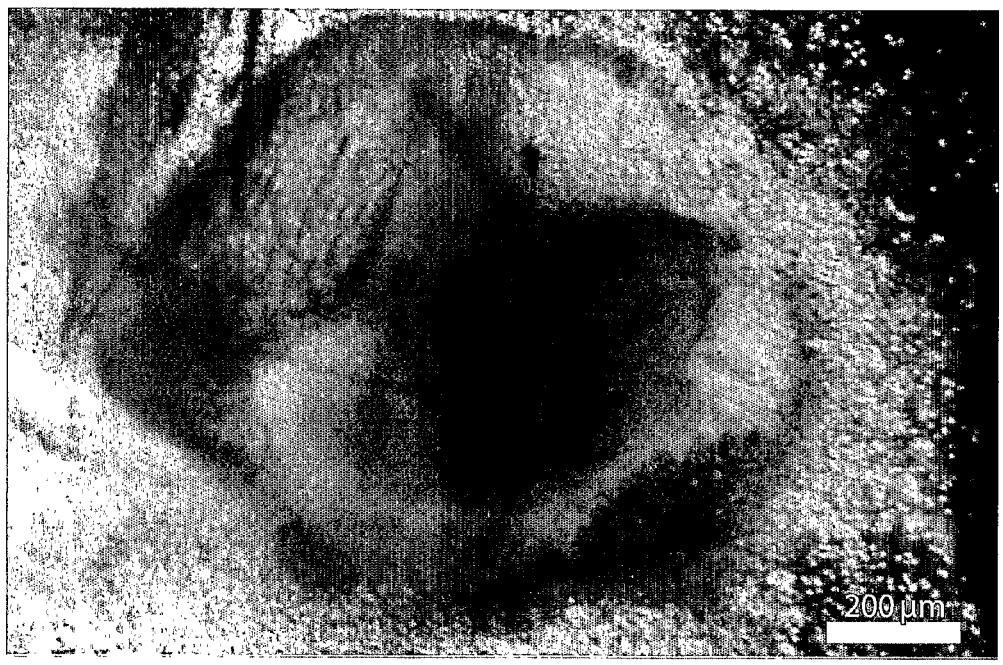

FIG. 18. Red blood cells generated from mES cells at 36 mmHg $pO_{2gas}$ after 10 days of differentiation. Following the same protocol used to generate cardiomyocytes (see Examples 1 and 2), red blood cells are observed to be generated at 36 and 7 mmHg $pO_{2gas}$ but not 142 mmHg.

Figure 19:
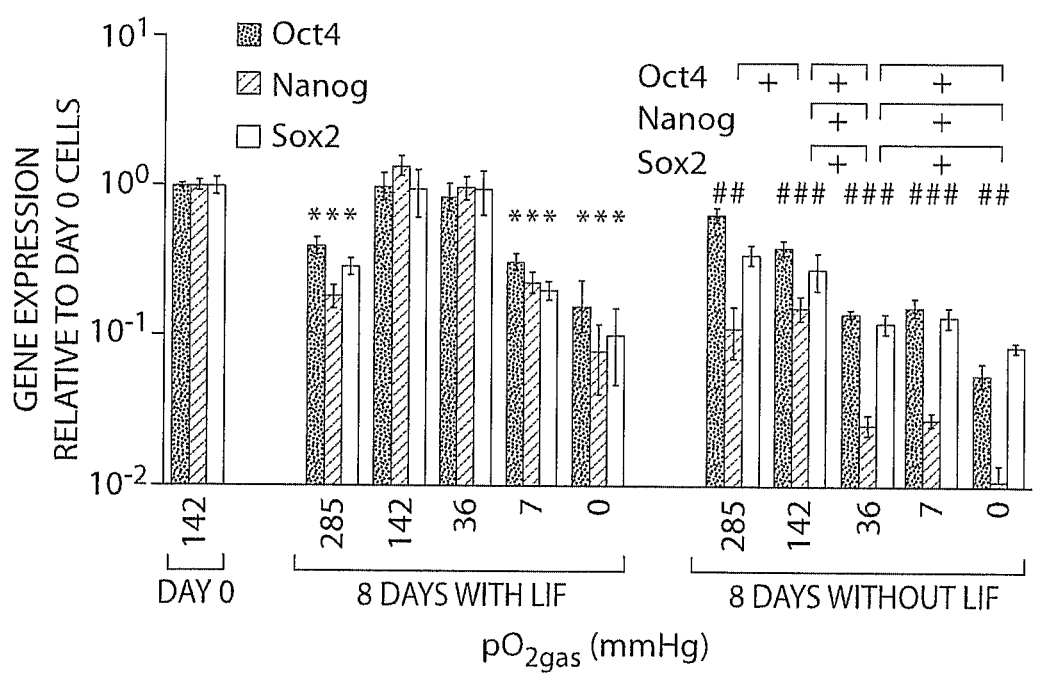
Figure 20A:
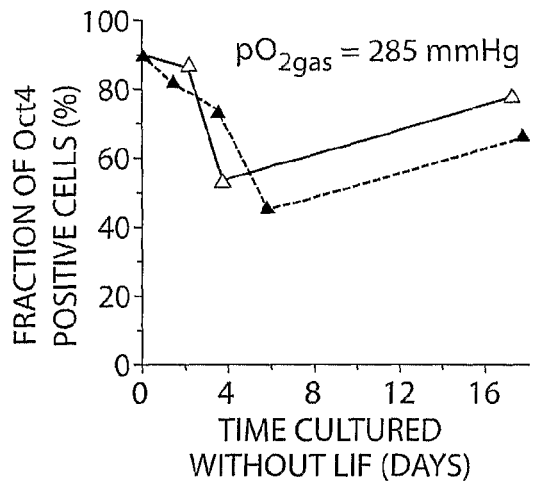
Figure 20B:
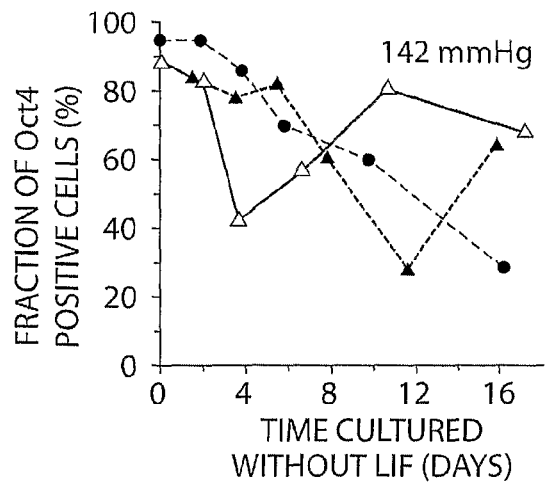
Figure 20C:
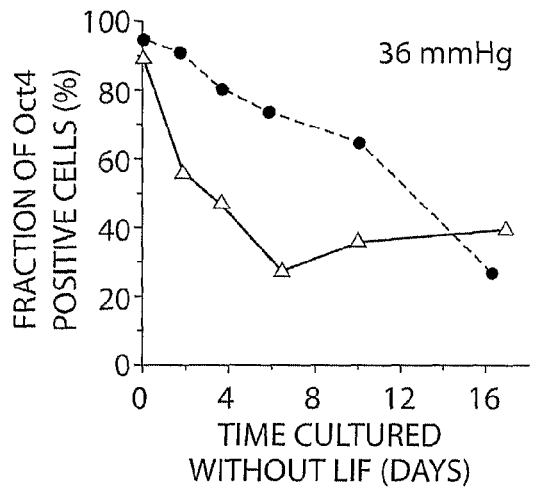
Figure 20D:
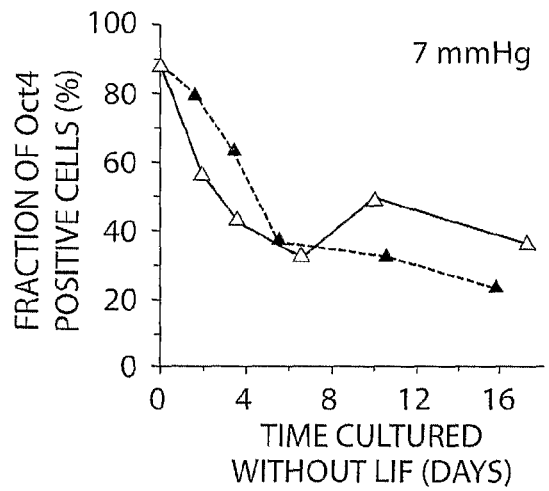
Figure 20E:
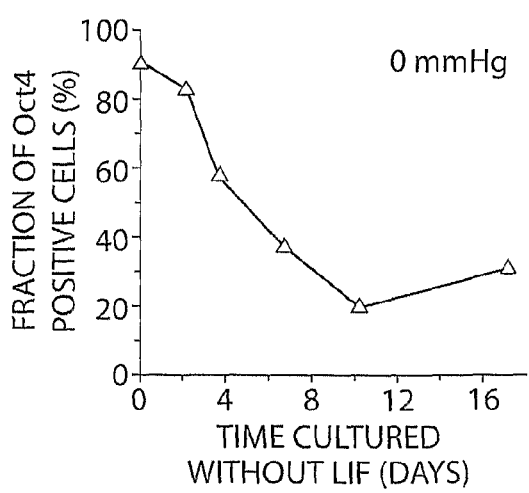
Figure 20F:
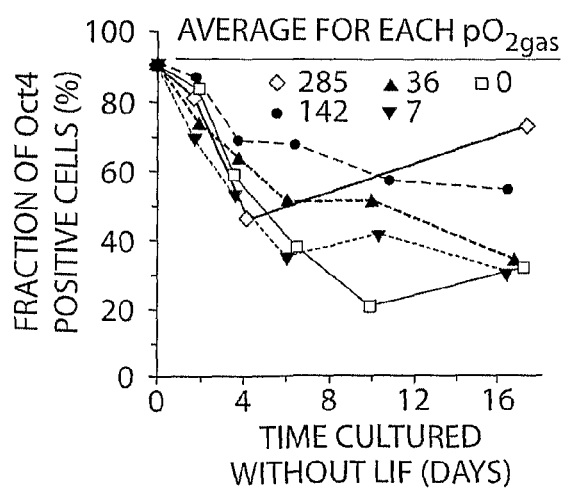

FIG. 19. Real-time PCR analysis of ES cell markers Oct4, Sox2, and Nanog in CCE cells cultured for 8 days with and without LIF in the culture medium. Results reported are mean±SD of data obtained with four different cultures carried out with the same undifferentiated stem cells starting at day 0. All data is normalized to that for the cells at day 0. Gene expression for conditions with LIF that are significantly different from the day 0 undifferentiated cells are indicated with an asterisk (*). For conditions without LIF, the pound sign (#) denotes a significant difference in gene expression between cultures with LIF and without LIF at identical $pO_{2gas}$ conditions, and the plus sign (+) denotes significant difference between $pO_{2gas}$ conditions indicated by the brackets, all without LIF.

FIG. 20. Fraction of Oct4 positive CCE cells during culture in medium without LIF beginning on day 0. Results from up to three independent experiments at different $pO_{2gas}$ conditions are shown in panels A-E. Data obtained from comparable times for each $pO_{2gas}$ were averaged, and the result is plotted in panel F.

Figure 21A:
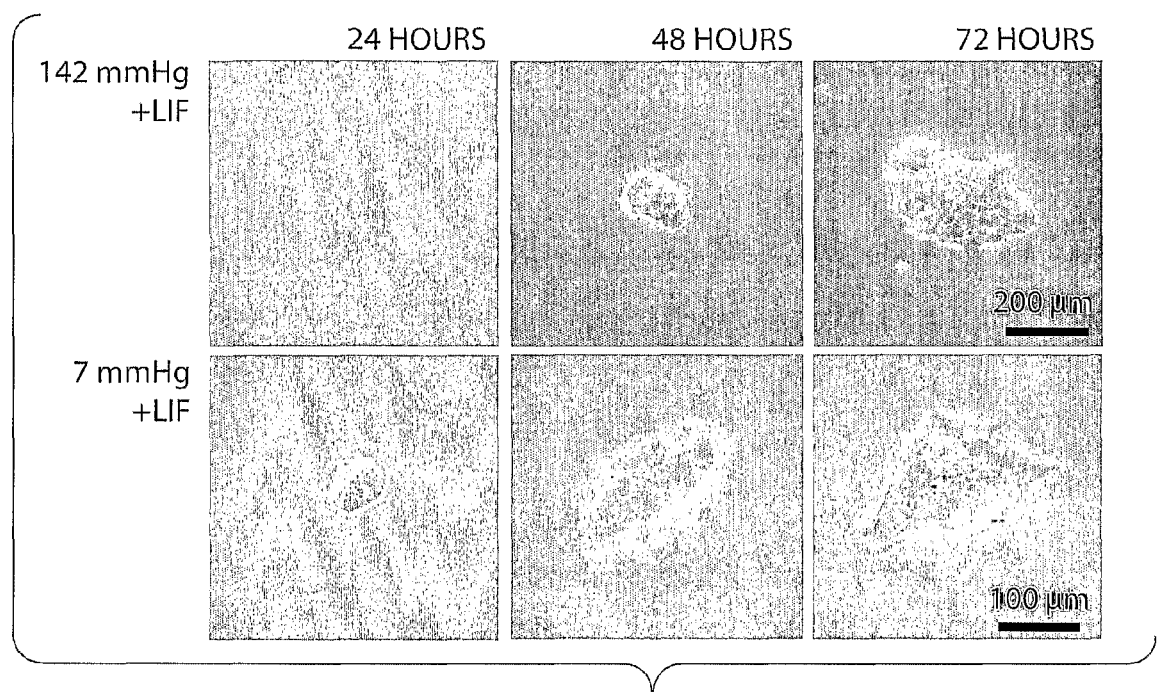
Figure 21B:
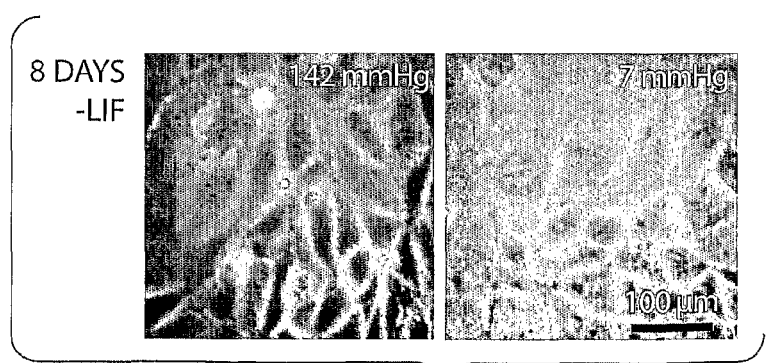

FIG. 21. Phase contrast photomicrographs of CCE cells. CCE cells cultured (A) for up to 72 hours with 1000 U/mL LIF at $pO_{2gas}$ of 142 mmHg (top panels) or 7 mmHg (middle panels) or (B) 8 days without LIF (bottom 2 panels) at a $pO_{2gas}$ of 142 or 7 mmHg.

Figure 22:
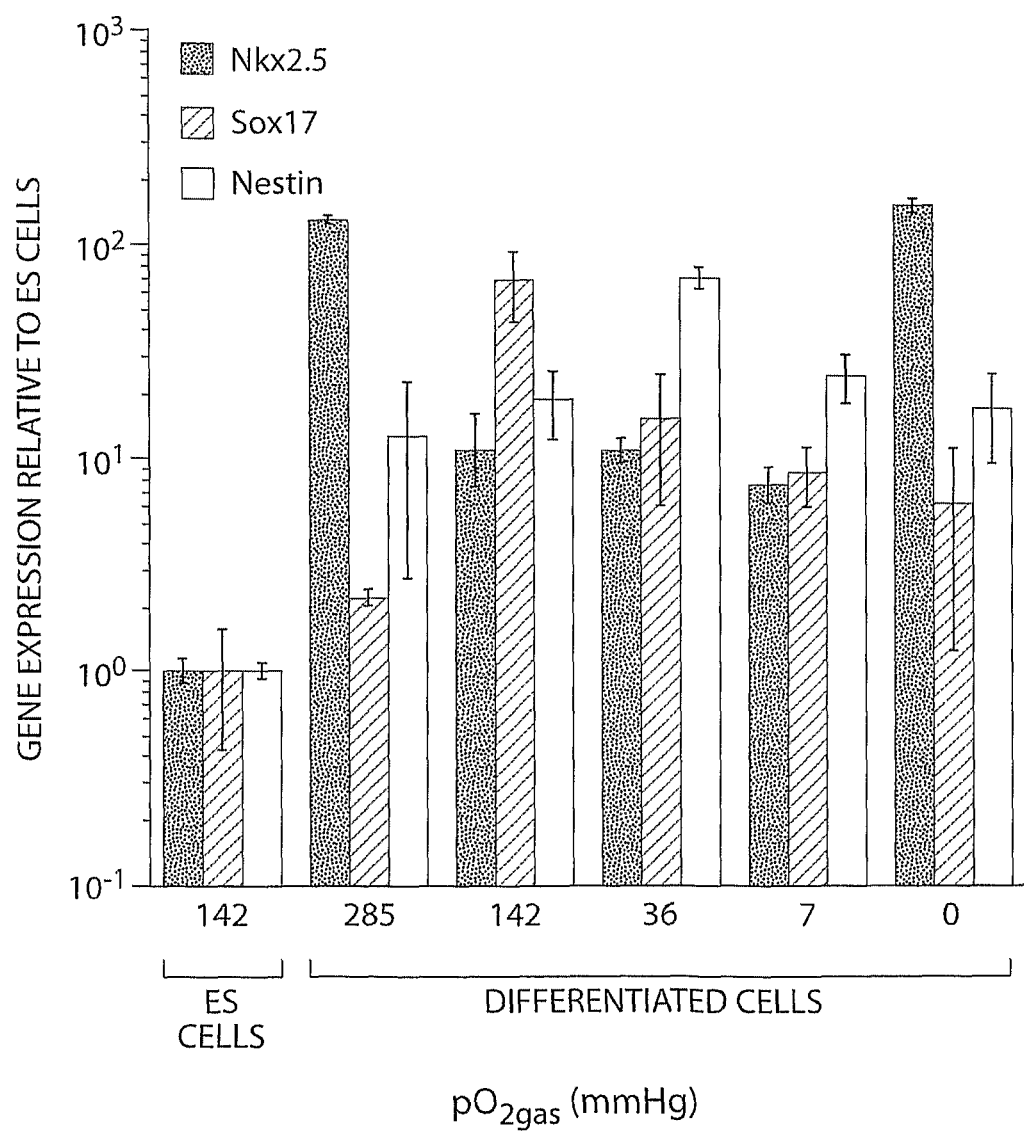

FIG. 22. Change in gene expression levels as a result of oxygen partial pressure changes. Real-time PCR analysis of the differentiation markers Nkx2.5, Sox17, and Nestin of CCE cells cultured at the indicated $pO_2$ for 8 days with 1000 U/mL LIF and then differentiated without LIF in hanging drop EBs for 2 days and in attached culture for an additional 3 days at the same $pO_2$. Nkx2.5, Sox17, and Nestin are markers for mesoderm, endoderm, and ectoderm, respectively. Results reported are mean±SD of data obtained with four different cultures carried out with the same undifferentiated stem cells starting at day 0, and all of the results were significantly different from the control (undifferentiated ES cells at 142 mmHg).

Figure 23:
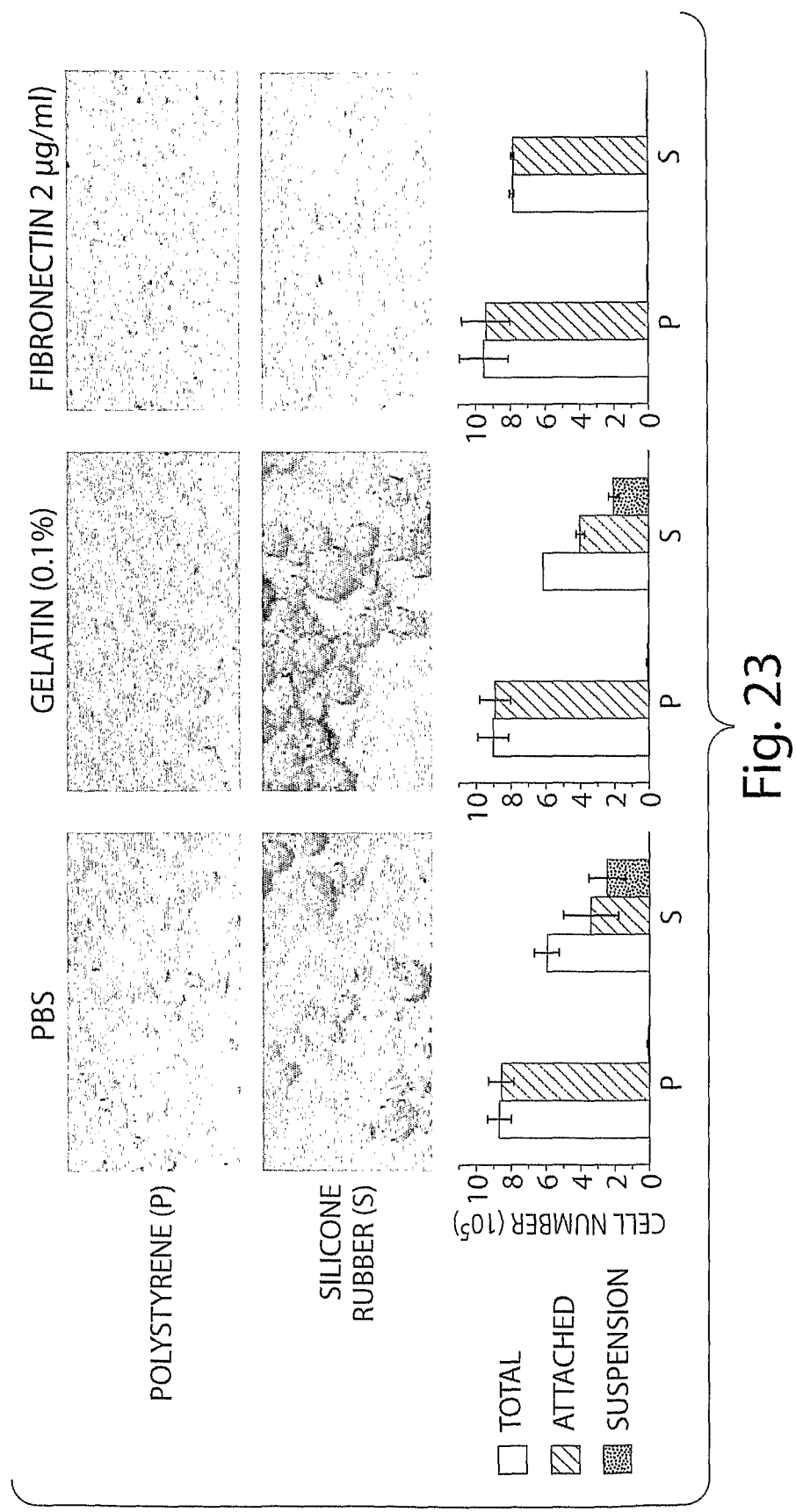

FIG. 23. Adhesion of ES cells to polystyrene and silicone rubber. Adhesion of mES cells to polystyrene and silicone rubber in their native states or with 0.1% gelatin in water or 2 mg/ml fibronectin in PBS adsorbed onto the surface for 24 hr prior to cell addition. Below each pair of micrographs is quantitative data for the total, attached, and suspension cell numbers. Results shown are mean±SD for three wells in a 24 well plate seeded with 2×105 cell 26 hr prior to performing the cell counts.

Figure 24:
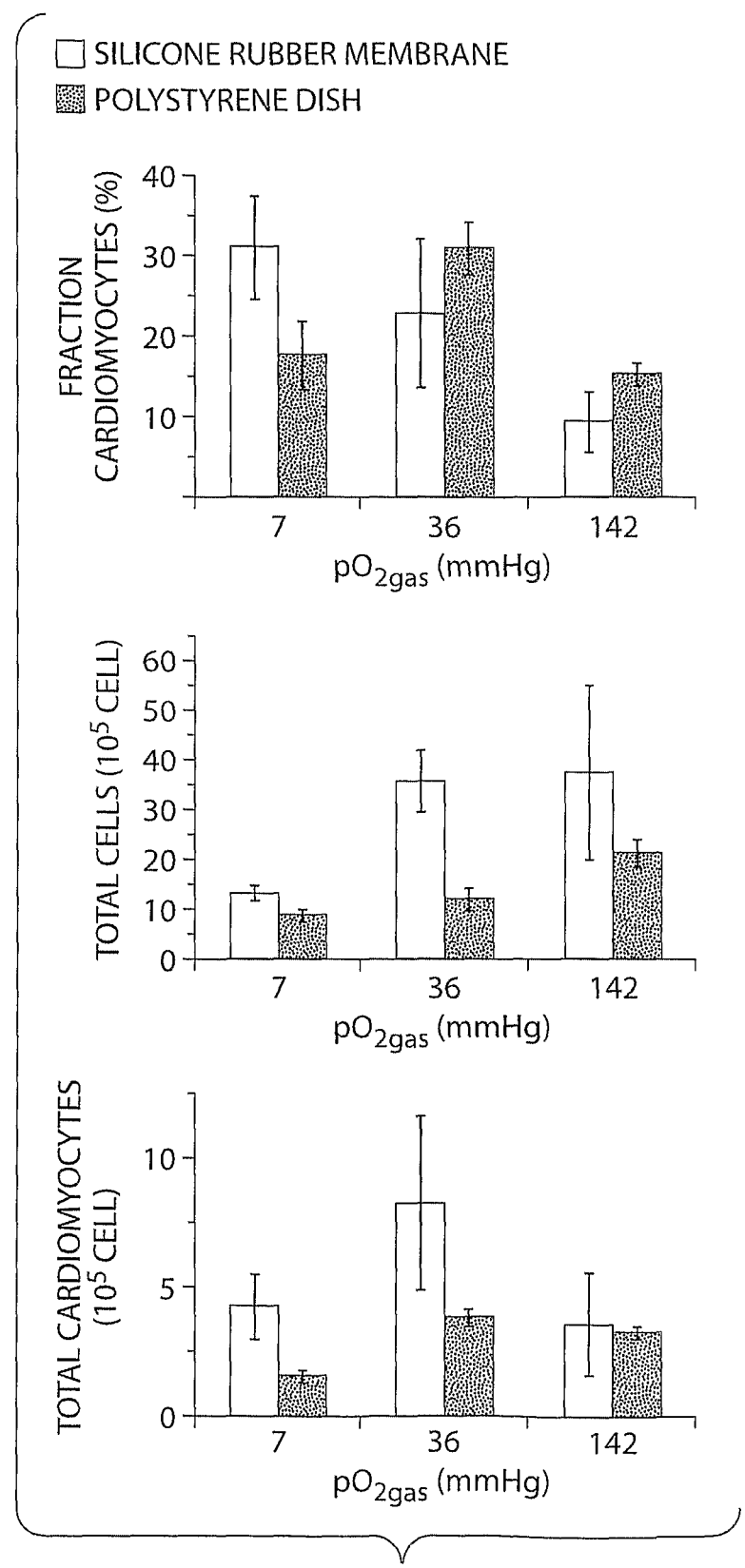

FIG. 24. Differentiation on silicone rubber membranes and polystyrene dishes. Fraction of cells that were cardiomyocytes (top), total number of cells (middle), and total number of cardiomyocytes (bottom) for cells cultured at constant $pO_{2gas}$ conditions of 7, 36, or 142 mmHg for 11 days in silicone rubber membrane based dishes (white bars) and polystyrene dishes (black bars). The number fraction of cardiomyocytes was determined by flow cytometry of MF-20-immunostained, trypsin-dispersed cell samples. Data for silicone rubber membrane-based dishes are shown as mean±SD for 7 independent experiments, while data for polystyrene dishes are shown as mean±SD for 3 replicate wells in a single experiment. All experiments were started with 30 EBs/well (0.15×105 cells/well).

FIG. 25. Theoretical predictions for $pO_{2cell}$ during monolayer culture. The predicted $pO_{2cell}$ for ES cell monolayers as a function of cell density and medium height on polystyrene, FEP-teflon membrane, and silicone rubber membrane surfaces. The OCR/cell used was 29 amol/cell sec, and the $pO_{2cell}$ was determined using Eqn.1. (B) The fractional approach of the $pO_{2cell}$ to steady state after a step change in $pO_{2gas}$ as estimated using numerical simulations in a cell-free system.

Figure 26:
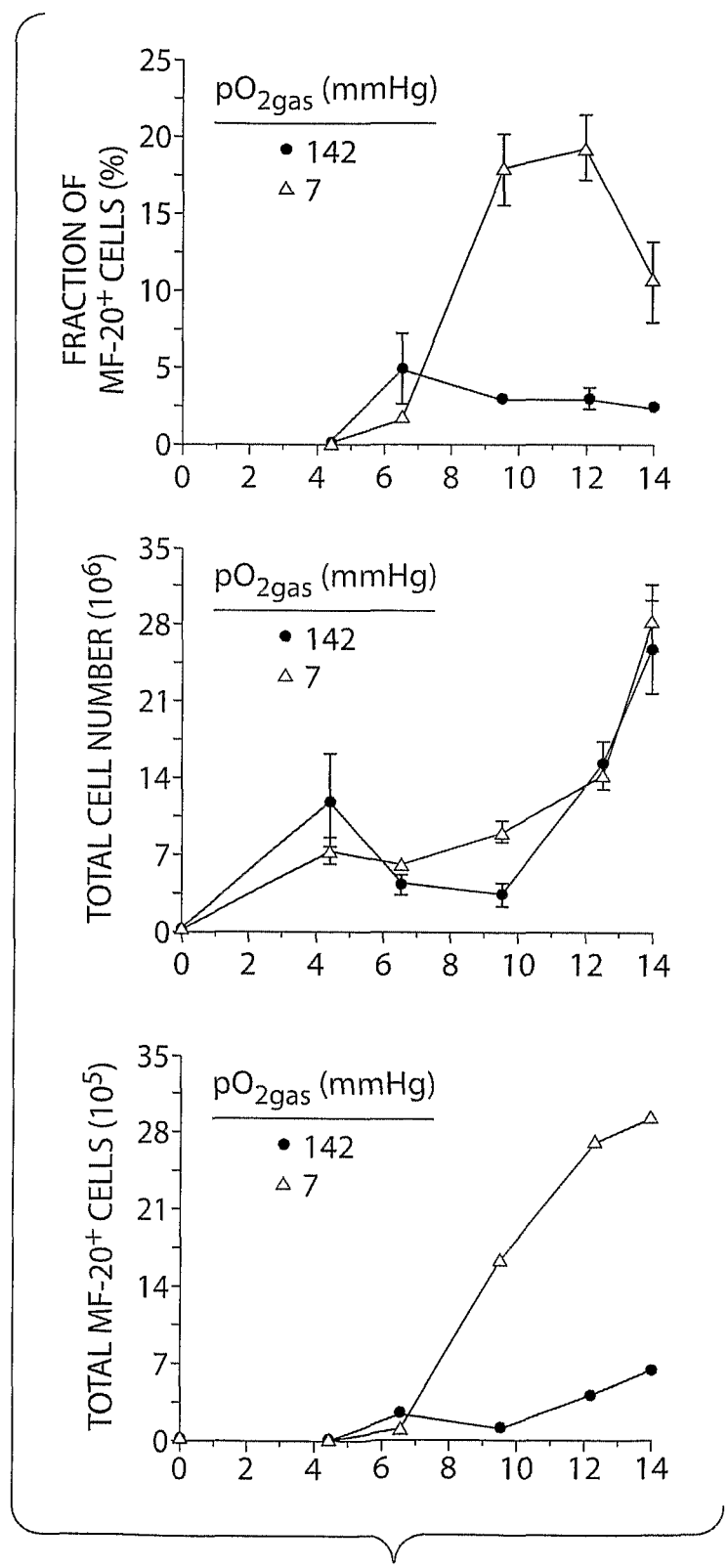
Figure 27A:
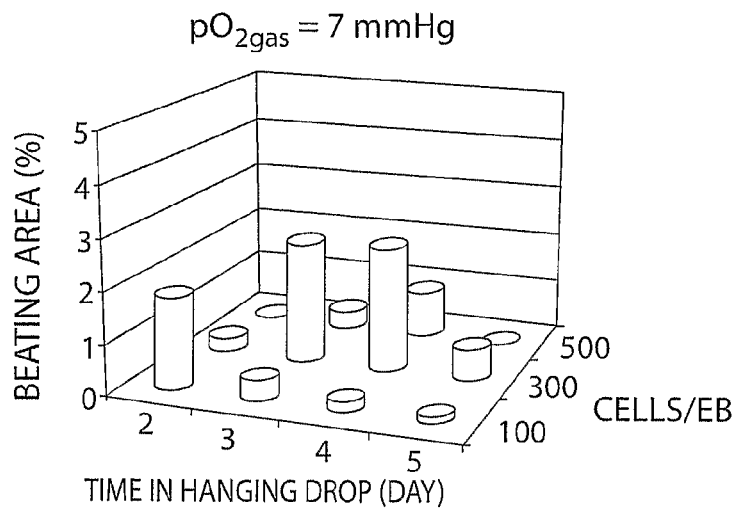
Figure 27B:
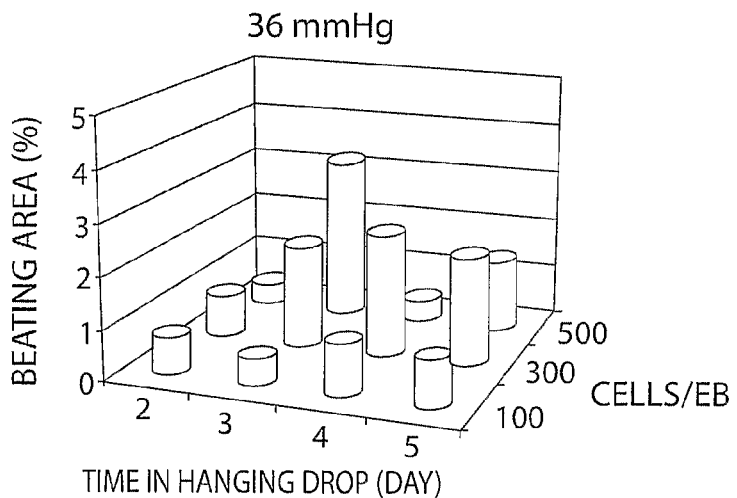
Figure 27C:
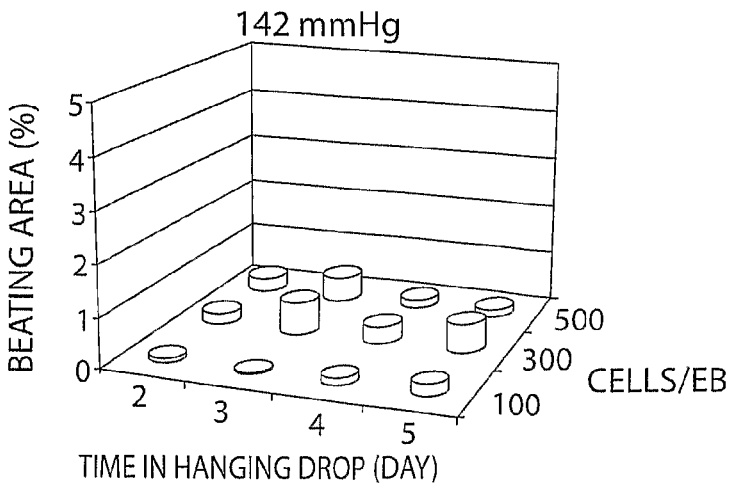
Figure 27D:
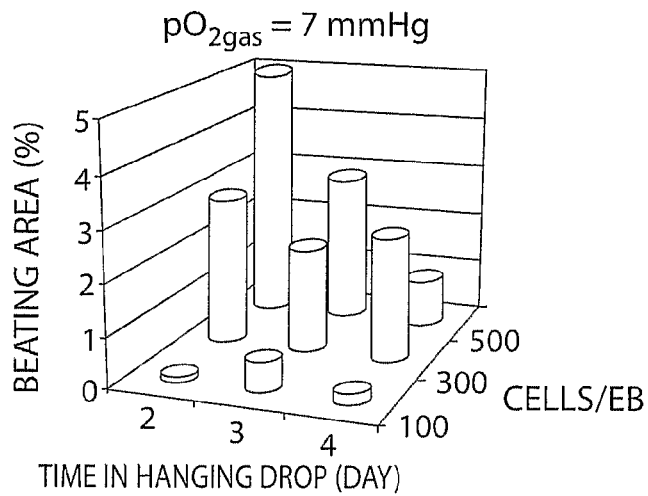
Figure 27E:
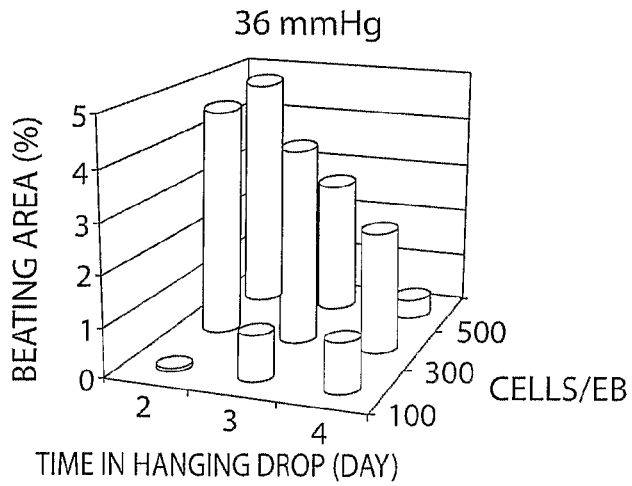
Figure 27F:
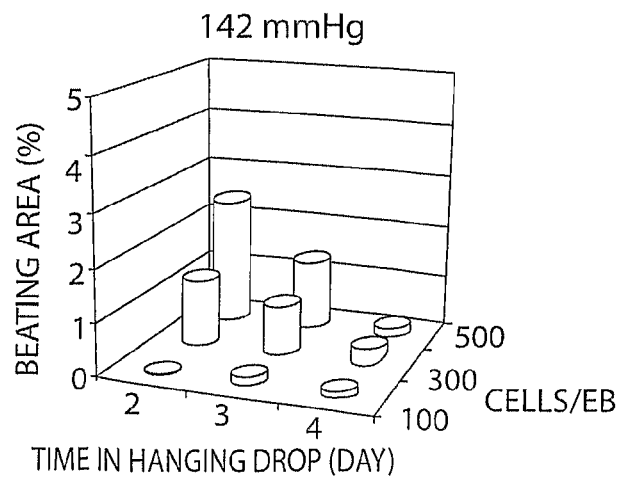

FIG. 26. Temporal appearance of cardiomyocytes during ES cell differentiation. Temporal changes in fraction of cells that were cardiomyocytes, total cell number, and total cardiomyocyte number during J1 ES cell differentiation. EBs were formed in suspension culture in DMEM with 10% FBS for 4 days, before being transferred to an adherent dish containing serum-free ITS medium with fibronectin for an additional 10 days of attached culture. Results are mean±SD for 3 independent wells at each time point in a single experiment.

FIG. 27. Effect of EB size and time in hanging drops on cardiomyocyte differentiation. The fraction of a 24-well plate that was covered with spontaneously contracting cells at different $pO_{2gas}$ conditions after 11 days of differentiation is shown as a function of the number of cells present in the initial hanging drop and the time in hanging drop culture before transfer to a fibronectin-coated silicone rubber membrane-based 48 well plate (10 EB/well). The hanging drops were formed using DMEM with 10% FBS and were transferred to a serum free ITS medium 1 day after plating the EBs (A-C), or on day 5 (D-F). Results shown are the mean of two independent experiments performed with J1 ES cells.

It is to be understood that the Figures are not required for enablement of the invention.

DETAILED DESCRIPTION OF THE INVENTION

The invention provides unexpectedly improved methods for differentiating pluripotent stem cells such as ES cells in vitro. These methods involve the culture of pluripotent stem cells such as ES cells in a low oxygen partial pressure condition. Importantly, culture of pluripotent stem cells such as ES cells at low oxygen partial pressure conditions changes the timing and magnitude of mesoderm, endoderm and ectoderm gene expression profiles during the differentiation of these cells, and thereby favors mesoderm and endoderm differentiation at least during short term cultures. Over shorter time periods, ectoderm differentiation is not favored. The methods provided herein enhance differentiation of pluripotent stem cells such as ES cells towards the mesoderm and endoderm lineages in short term cultures in the absence of exogenous factors thought important for such differentiation and lineage commitment. The invention however also contemplates the use of low oxygen partial pressure together with such exogenous factors, and in some embodiments such combination results in synergistic effects.

For the sake of brevity, aspects, embodiments and exemplifications of the invention are discussed in the context of pluripotent stem cells that are ES cells. As used herein, a pluripotent stem cell is a cell that can differentiate into mesoderm, endoderm and ectoderm lineages. It is to be understood that the invention contemplates and can be carried out using pluripotent stem cells derived from the dedifferentiation of adult cells (such as induced pluripotent stem cells), as well as pluripotent stem cells derived from embryonic tissue (such as ES cells). ES cells may be produced from cells that have undergone by somatic cell nuclear transfer, parthenogenesis, androgenesis or other asexual techniques. Embryos derived from sexual reproduction may be referred to herein as "fertilized embryos" in order to distinguish them from asexually derived embryos. Accordingly, the invention contemplates the use of ES cells from these various sources.

Some aspects of the invention employ a single culture condition characterized by a low oxygen partial pressure while other aspects employ at least a first and a second culture wherein the first culture condition is characterized by low oxygen partial pressure and the second culture condition is characterized by a higher oxygen partial pressure. It has been found according to the invention that low oxygen partial pressure culture yields an increased number of mesodermal and endodermal progenitor and/or more differentiated cell such as a terminally differentiated end stage cell as compared to culture at an oxygen partial pressure of 142 mmHg. It has also been found that increasing the oxygen partial pressure during the culture period (e.g., from 36 mmHg to 142 mmHg) yields even further increases in the number of precursors and/or end stage cells from such cultures. As an example, increasing the oxygen partial pressure from 36 mmHg to 142 mmHg during ES cell differentiation yielded 304 cardiomyocytes per initial ES cell. Moreover, the population of cells harvested from such a culture was also enriched in cardiomyocytes as compared to populations harvested from culture at 142 mmHg only.

Thus, the invention provides methods for enhancing induction of ES cell differentiation towards the mesodermal and endodermal lineages, as well as cell populations enriched in mesoderm and/or endoderm progenitors and/or more differentiated cells such as terminally differentiated end stage cells. It will be understood by one of ordinary skill in the art that such cell populations can then be a further fractionated in order to achieve greater enrichment and in some instances purity of the desired population, including for example cardiomyocytes.

It has also been found, surprisingly, according to the invention that the timing and magnitude of gene expression during the differentiation process for ES cells is changed in the presence of low oxygen partial pressure in some instances, as shown in the Examples. That is, as described in greater detail in the Examples, in some instances mesoderm and endoderm differentiation from ES cells is delayed and also extended in time compared to differentiation at an oxygen partial pressure of 142 mmHg. For example, when ES cells are differentiated in 142 mmHg oxygen the mesodermal differentiation marker brachyury T is expressed at day 3 and then only slightly at day 4. However when ES cells are differentiated in 7 mmHg oxygen this maker is expressed at day 4 and day 5 of culture. Accordingly, the expression of brachyury is delayed by about a day and then also extended by about a day. A similar observation was made with Tbx6, another mesodermal marker. When ES cells are differentiated in 142 mmHg oxygen this marker is expressed at about day 3. However when ES cells are differentiated in 7 mmHg this marker is expressed at days 4 and 5. In addition, these markers appear to be expressed at higher levels when cultured at the lower oxygen partial pressure. Thus, in some instances, a delayed and extended differentiation process occurs which more closely approximates physiological development and differentiation than does culture at 142 mmHg. This provides a larger temporal window during which the events underlying this differentiation may be influenced and/or manipulated and/or cells at various stages of development may be harvested.

The enhanced differentiation is exemplified in some aspects by the production of cardiomyocytes from ES cells. Thus, many aspects and embodiments of the invention are described in the context of cardiomyocyte production. It is to be understood however that the invention is not so limited and that other mesodermal and endodermal cell types, including progenitors and more differentiated cells such as terminally differentiated end stage cells, may be similarly be generated according to the methods provided herein.

Thus the methods described herein generally require exposure of ES cells to low oxygen partial pressure ($pO_2$). According to some but not all aspects of the invention, the period of exposure to low $pO_2$ exposure is followed by a period of exposure to higher $pO_2$. The invention is based in part on the unexpected findings that extended culture of ES cells (e.g., at least 4 days, at least 6 days, at least 8 days, or at least 10 days) in low $pO_2$ or culture of ES cells at low $pO_2$, optionally followed by culture at higher $pO_2$, results in significantly increased production of mesodermal cells (such as cardiomyocytes) or endodermal cells than has been heretofore reported. These culture conditions also yield cell populations enriched in mesodermal cells (such as cardiomyocytes) or endodermal cells, and also progenitors of such cell types.

The invention therefore contemplates the use of low oxygen partial pressure conditions in the context of any ES cell mesodermal or endodermal differentiation process known in the art including but not limited to those described by D'Amour et al. Nat Biotechnol published online Oct. 19, 2006, Kroon et al. Nat. Biotechnol. 2008 26(4):443-452, and Fehling et al. 2003 Development 130:4217-4227. The use of low oxygen partial pressure will enhance the differentiation efficacy of such methods. Mesodermal cells and progenitors (or tissues) to be generated according to the methods of the invention include bone, muscle such as cardiac muscle, skeletal muscle and smooth muscle (e.g., of the gut), connective tissue such as the dermis and cartilage, kidneys, the urinoogenital system, blood (or hematopoietic), heart and vasculature. Endodermal cells and progenitors (or tissues) to be generated according to the methods of the invention include epithelial cells such as those lining the digestive tube, liver, pancreas including the beta cells in islets of Langerhans, trachea, bronchi, alveoli, urinary bladder, urethra, thyroid and thymus.

The invention is further premised in part on the observation that ascorbic acid when used in culture in a reduced $pO_2$ environment further enhances differentiation of ES cells, including particularly into cardiomyocytes. In some embodiments, this enhancement is synergistic. The invention therefore contemplates the combined use of low oxygen partial pressure with differentiative factors including but not limited to mesoderm differentiative factors (including but not limited to hematopoietic differentiative factors or cardiac differentiative factors) and endoderm differentiative factors.

Various methods of the invention therefore are directed towards producing or generating from ES cells progenitors and differentiated cells of mesoderm and endoderm lineages. As used herein, the terms "producing" and "generating" are used interchangeably. In some particular embodiments, the methods are directed to producing or generating cardiomyocyte progenitors and cardiomyocytes from ES cells. It has been unexpectedly found according to the invention that substantially more cardiomyocytes can be generated per initial (or input) ES cell using the methods of the invention as compared to previously reported methods. See Bauwens et al, Biotechnol Bioengin., 90(4):452-461, 2005). The methods provided herein can yield on average at least 100, preferably at least 200, and even more preferably at least 300 mesoderm lineage cells, including but not limited to cardiomyocytes, per initial ES cell. Similarly, the methods may be used to generate at least 20, at least 30, at least 40, at least 50, at least 60, at least 70, at least 80, at least 90, at least 100, at least 200, at least 300, or more endoderm lineage cells such as definitive endoderm precursors and precursors at other stages of endoderm differentiation leading to beta cells of islets of Langerhans.

The methods of the invention are also directed towards enrichment of mesoderm and/or endoderm progenitors and/or differentiated cells such as but not limited to cardiomyocytes derived from ES cells. In exemplary embodiments of the invention, cell populations from ES cell cultures generated at low oxygen partial pressure have a higher proportion of cardiomyocytes compared to a control cell population (e.g., one generated at an oxygen partial pressure of 142 mmHg). As used herein, a cell population that is enriched for a particular progenitor or a more differentiated cell is a population having a greater proportion or percentage of such progenitors or differentiated cells (e.g., number of particular cells per a given number of total cells in the population) than a control population. The control population may be the population generated in an oxygen partial pressure of 142 mmHg but with otherwise identical culture conditions. The invention provides methods for producing cell populations that are at least 20%, at least 30%, at least 40%, at least 50%, at least 60%, at least 70%, at least 80%, at least 90%, at least 95%, or 100% of a particular desired cell type.

In exemplary embodiments, the invention provides methods for producing cell populations that are at least 25%, at least 35%, at least 40%, at least 50%, at least 55%, or a higher percentage of cardiomyocytes in the absence of post-differentiation selection. These populations contain a higher proportion of cardiomyocytes than previously reported populations of ES cell derived cardiomyocyte. See Klug et al., J. Clin. Invest., 98:216-224, 1996. Importantly, the methods of the invention achieve these enriched populations of cardiomyocytes in the absence of cardiomyocyte selection following differentiation. Thus, the instant invention provides methods for achieving enriched cardiomyocyte populations simply based on particular ES cell culture conditions. The invention therefore provides simplified methods for enriching cardiomyocytes over the prior art methods.

It will, however, be understood that the methods of the invention may be combined with selection methods based on, for example, cell surface phenotype, cell size and/or granularity, cell cycle status, reporter gene expression (e.g., a detectable marker, such as GFP, tagged to a protein under the control of mesoderm or endoderm-associated transcription factor(s)), and the like. These selection methods may be applied to cells harvested at any stage of culture. These methods are known in the art and the invention is not to be limited in this regard.

The methods of the invention in various aspects are directed towards exposing cells in culture to low oxygen partial pressure (i.e., an oxygen partial pressure that is less than 142 mmHg if cultured in the presence of $CO_2$ and a bicarbonate-based buffer, or less than 160 mmHg if cultured in the absence of $CO_2$ and with another buffer such as HEPES). Cells however are cultured in liquid phase and oxygen content (or level) is typically (and more conveniently) set for the gas phase of such cultures. The oxygen partial pressure at the surface of a cell is referred to herein as $pO_{2cell}$. $pO_{2cell}$ depends on several factors including medium depth, cell density, cellular oxygen consumption rate, diffusion characteristics of the medium, and $pO_{2gas}$. The Examples provide an algorithm for determining $pO_{2cell}$ based on $pO_{2gas}$. Means for measuring $pO_{2cell}$ include but are not limited to the use of fluorescent based oxygen sensors (e.g., ruthenium based compounds or complexes) that can be placed in contact with cells in culture (e.g., they may be impregnated in an oxygen permeable membrane in contact with the cells).

The oxygen partial pressure in the gas phase of a culture system is referred to herein as $pO_{2gas}$. As used herein, oxygen partial pressure will refer to $pO_{2gas}$ unless otherwise indicated and for convenience may be referred to as $pO_2$.

Cells grown in monolayers are more likely to be exposed to an oxygen partial pressure that approximates the gas phase oxygen partial pressure than are cells grown in a non-monolayer manner (e.g., in layers, spheres or aggregates). The difference between $pO_{2cell}$ and $pO_{2gas}$ for cells in a monolayer is typically due to diffusion gradients in the culture medium. Cells grown in a non-monolayer manner, particularly those buried within a sphere or aggregate, will have a $pO_{2cell}$ that is less than the $pO_{2gas}$ because of the internal oxygen gradients within for example multiple layers of cells and/or aggregates. The invention contemplates reducing or eliminating the difference between $pO_{2cell}$ and $pO_{2gas}$ by enhancing oxygen transport to the cells. In a preferred embodiment, cells are cultured under conditions where $pO_{2cell}$ of a cell layer or at the surface of a 3-dimensional aggregate is approximately equal to $pO_{2gas}$. This can be accomplished in number of ways, as will be discussed in greater detail below.

Various modifications to the culture system may be performed in order to reduce the difference between $pO_{2gas}$ and $pO_{2cell}$. For example, convective oxygen transport in mechanically mixed or perfused vessels may be used, including stirring of and/or bubbling of oxygen through a culture medium. The cultures may be subject to in situ generation of oxygen using electrochemical hydrolysis of water. Alternatively or additionally, culture vessels having one or more sides, walls and/or bottom to which cells attach and grow that comprise an oxygen permeable membrane can also be used. As used herein, an oxygen-permeable membrane is a membrane that has an oxygen permeability greater than that of a standard (e.g., polystyrene) culture dish. One example of an oxygen-permeable membrane is a fluoroethylene-propylene copolymer (FEP-Teflon) membrane. Culture vessels comprising this membrane are commercially available as Lumox dishes (Greiner Bio-One, Munich). Another example of an oxygen-permeable membrane is a silicone rubber membrane, which is used in the Examples. The oxygen permeabilities of FEP Teflon and silicone rubber are $0.2$-$0.4 \times 10^{-14}$ and $26 \times 10^{-14}$ mol cm$^{-1}$ mmHg$^{-1}$ sec$^{-1}$, respectively.

Silicone rubber culture vessels, as used herein, are culture vessels that comprise a silicone rubber membrane bottom. In other words, the internal face of the vessel to which the ES cells attach is made of silicone rubber. The advantage of silicone rubber is its high permeability to gases such as oxygen. An example of a silicone rubber culture vessel is a silicone rubber dish, described in the Examples. In still other embodiments, an insert of such oxygen permeable membranes is placed in a culture vessel. Inserts of silicone rubber membranes are available from for example Wilson Wolf.

Additionally or alternatively, the ES cells may be cultured in hanging drops, as described in greater detail herein. Oxygen control may also be accomplished by the use of a perfluorocarbon layer for growing cells, or by any other method known in the art.

Oxygen partial pressure is generally referred to herein in units of mmHg. However many oxygen control devices associated with culture incubators express oxygen levels as a percentage. Generally $pO_{2gas}$ in mmHg can be determined based on knowledge of a percent oxygen measurement using the following formula:

$$pO_2 = (\% \text{ oxygen}) \times (760 \text{ mmHg})$$

In this equation, 760 mmHg is the atmospheric pressure.

For a humidified environment at 37° C. (which is generally the case with culture incubators), $pO_{2gas}$ can be determined based on the composition of the oxygen at the incubator inlet measured as percent oxygen (usually specified by the content of a compressed gas mixture in a tank) using the following formula:

$$pO_2 = (\% \text{ oxygen}) \times (760 - 47 \text{ mmHg})$$

In this equation, 760 mmHg is the atmospheric pressure and 47 mmHg is the vapor pressure of water at 37° C. If the inlet gas generally consists of about 5% $CO_2$, then oxygen levels of 1%, 5%, 20%, and 40% correspond to $pO_{2gas}$ of 7 mmHg, 36 mmHg, 142 mmHg, and 285 mmHg in the humidified incubator. Inlet gas for a standard culture incubator is 20% oxygen (95% air and about 5% $CO_2$), and $pO_{2gas}$ is therefore about 142 mmHg.

In many cases, during cell culture in bioreactors, the % oxygen is actually given as % of air saturation. The equation to convert between the two is $$\% \text{ absolute} = \% \text{ air saturation} \times 0.21$$

In this equation, 0.21 is the volume fraction or mole fraction of oxygen under atmospheric conditions.

As used herein, low oxygen partial pressure (or low $pO_2$) refers to a $pO_2$ that is less than 142 mmHg for cultures in the presence of 5% $CO_2$ (inlet gas). This level of $CO_2$ represents typical culture conditions in the art. In some embodiments, low $pO_2$ refers to a $pO_2$ that is less than 80 mmHg, less than 70 mmHg, less than 60 mmHg, or lower. In some embodiments, low $pO_2$ refers to a $pO_2$ that is less than 50 mmHg. Low $pO_2$ therefore may be a $pO_2$ that is less than 40 mmHg, less than 30 mmHg, less than 20 mmHg, less than 10 mmHg, less than 5 mmHg, or even zero mmHg. Low $pO_2$ may be a $pO_2$ in the range of 0-80 mmHg, 0-70 mmHg, 0-60 mmHg, 5-80 mmHg, 5-70 mmHg, or 5-60 mmHg. Low $pO_2$ may also be a $pO_2$ in the range of 5-50 mmHg, 10-50 mmHg, 20-50 mmHg, and 20-40 mmHg, including every integer therebetween (i.e., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50 mmHg). In some embodiments, the $pO_2$ is about 7 mmHg or about 36 mmHg. As used in the context of $pO_2$ measurements, the term "about" indicates a difference with the indicated value in the range of 0-15 mmHg.

In some embodiments of the invention, ES cells are differentiated in low oxygen partial pressure, as described above, for the entirety of the culture period. It has been found according to the invention that this low oxygen culture yields higher numbers or proportions of particular progenitor or differentiated cells as compared to culture at 142 mmHg in a $CO_2$ based culture system. The culture period may be 1-20 days, or longer. In some embodiments it is at least 3 days, at least 4 days, at least 5 days, at least 6 days, at least 7 days, at least 8 days, at least 9 days, at least 10 days, or more.

In other aspects, the invention contemplates the use of a two step culture method for the differentiation of ES cells. This method would comprise a first culture step in which the $pO_2$ is less than 142 mmHg (assuming a $CO_2$ based culture system). The $pO_2$ in this culture step may be less than 80 mmHg, less than 70 mmHg, less than 60 mmHg, or lower. The $pO_2$ in the first step may be less than 50 mmHg, less than 40 mmHg, less than 30 mmHg, less than 20 mmHg, less than 10 mmHg, less than 5 mmHg, or zero mmHg. The first culture step is carried out for a period of time that may range from 1-20 days, 2-20 days, 2-15 days, 2-10 days, 4-8 days, or 5-7 days, depending on the embodiment. Thus, this time period may be 1, 2, 3, 4, 5, 6, 7, 8, 9, 10, 11, 12, 13, 14, 15, 16, 17, 18, 19, 20 days or more, depending on the embodiment. In some important embodiments, the time period is 5 or 6 days.

In some embodiments, the culture method further comprises a second culture step in which the $pO_2$ is increased to a level that is greater than the $pO_2$ of the first culture step. The $pO_2$ in this second culture step may be a $pO_2$ that is greater than 50 mmHg, greater than 60 mmHg, greater than 70 mmHg, greater than 80 mmHg or more. The $pO_2$ in this second culture step may be a $pO_2$ that is at least 75 mmHg, at least 100 mmHg, at least 120 mmHg, at least 135 mmHg, at least 150 mmHg, at least 160 mmHg, at least 175 mmHg, at least 200 mmHg, at least 250 mmHg, at least 300 mmHg, at least 350 mmHg, or about 400 mmHg. In some embodiments, the $pO_2$ is $pO_{2gas}$. The second culture step is carried out for a period of time that is at least 2 days. The upper limit of this culture period will depend on the rate of the differentiation and viability of the cells in the culture. In some embodiments, this second culture period will be 1-20 days, 5-20 days, 10-20 days, 12-18 days, 13-17 days, or about 15 days. Thus, this time period may be 1, 2, 3, 4, 5, 6, 7, 8, 9, 10, 11, 12, 13, 14, 15, 16, 17, 18, 19, 20 days or longer.

In one particular embodiment, the first culture period is carried out at a $pO_2$ of less than 10 mmHg (e.g., about 7 mmHg) for 5 days, and the second culture period is carried out at a $pO_2$ of greater than 135 mmHg (e.g., about 142 mmHg) for at least an additional 5 days. In another particular embodiment, the first culture period is carried out at a $pO_2$ of less than 10 mmHg (e.g., about 7 mmHg) for 6 days, and the second culture period is carried out at a $pO_2$ of greater than 135 mmHg (e.g., about 142 mmHg) for at least an additional 4 days. In another particular embodiment, the first culture period is carried out at a $pO_2$ of about 36 mmHg for 6 days, and the second culture period is carried out at a $pO_2$ of about 142 mmHg for 15 days.

It is to be understood that although the method recites two culture steps it can still readily be performed in a single culture vessel, and it does not require the transfer of cells at the end of the first culture step into another culture vessel, although if hanging drops are used it may require transfer of EBs from hanging drops to culture vessels as described in detail herein. The method may also require observation and maintenance of the cells including regular media changes, etc.

It is to be further understood that any modification of oxygen partial pressure is contemplated between the first and the second culture step. That is, there may be intervening steps between the first and second culture step and these intervening steps may comprise increases and/or decreases of oxygen partial pressure.

$pO_{2gas}$ can be regulated during culture using manual and automated devices. Examples of commercially available automated devices include but are not limited to Oxycycler C42 from BioSpherix (Redfield, N.Y.), OWJ2720A from Queue Systems (Parkersburg, Va.), and Oxygen Monitoring System (FO/SYS2-T250, Instech Labs, Plymouth Meeting, Pa.).

While not intending to be bound by any particular theory, it is postulated that low oxygen partial pressure results in changes in the timing and magnitude of gene expression that results in or is associated with an increased production of mesoderm and endoderm progenitors and more differentiated cells (such as cardiac progenitor cells or cardiomyocytes). Beginning as soon as day 4 of differentiation culture, mesoderm and endoderm differentiation are favored. Ectoderm is not favored during the first 10 days of differentiation at oxygen partial pressures of about 7 mmHg. The low oxygen partial pressure may increase differentiation towards mesoderm and endoderm lineages and/or increase self-renewal of the progenitors of these lineages. Low oxygen may also stimulate further differentiation from these progenitors to terminally differentiated cells or it may cause the differentiated cells themselves to proliferate.

As used herein, ES cells are pluripotent cells isolated from the inner cell mass of blastocysts and propagated in vitro. These cells have the capacity to differentiate into any cell type in the body. ES cells of the invention therefore have been isolated from their natural environment (i.e., the blastocyst). That is, they have been physically separated from the blastocyst.

In some embodiments, the ES cells are untransfected (i.e., they have not been genetically manipulated after their establishment to comprise or express an exogenous nucleic acid). In some embodiments, the ES cells do not express an antibiotic resistance gene such as the neomycin gene. In some embodiments, however, the ES cells may be genetically engineered to express one or more cardiac lineage differentiation factors such as but not limited to VEGF. The ES cells may be murine or human ES cells.

A number of ES cell lines currently exist. These include murine ES cell lines such as J1, R1, D3, CCE, SCC10, B6/Blu, EDJ22, and B6/GFP, and human ES cell lines such as BG01, BG02, BG03, SA01, SA02, ES01, ES02, ES03, ES04, ES05, ES06, H1, H9, TE03, TE04, TE06, UC01, UC06, WA01, WA07, WA09 WA13 and WA14. Reference may be made to the NIH Human ES Cell Registry which lists various human ES cell lines made and whether and from whom such lines are available.

In addition, protocols for generating ES cells and lines are known in the art. The generation of murine ES cells and lines has been described. See for example Teratocarcinomas and ES cells: a practical approach (1987). E. J. Robertson, editor. IRL Press. and Wernig et al. Nature. 2007 Jun. 6 (online publication). U.S. Pat. Nos. 5,843,780 and 6,200,806 assigned to WARF describe the generation of human ES cells.

ES cell maintenance and differentiation culture conditions are also known in the art. See for example Keller, ES Cell Differentiation: Emergence of a New Era in Biology and Medicine, Gene Dev., 19:1129-1155, 2005. These culture conditions either maintain ES cells in an undifferentiated state or cause differentiation of ES cells into one or more lineages. Culture of ES cells in an undifferentiated state usually requires the presence of feeder cells, although it can also be performed on gelatin-coated tissue culture plates. (Zandstra et al., Tissue Eng., 9(4):767-778, 2003). Such feeder cells are typically mitotically inactivated for example via irradiation or treatment with mitomycin C. Suitable feeder cells for murine ES cells include embryonic fibroblasts. In certain culture conditions, leukemia inhibitory factor (LIF) can replace the requirement for feeder cells. A suitable medium for these cultures is high glucose DMEM supplemented with 10% ES cell qualified FBS.

Human ES cells can be grown and maintained in an undifferentiated state in serum-free defined media (e.g., DMEM/F12 medium containing 20% KnockOut serum replacement (Invitrogen), 1 mM L-glutamine (Sigma), 2-mercaptoethanol, and 1× non-essential amino acids (Sigma)) in the presence of feeder cells and bFGF (4 ng/ml, Invitrogen). Feeder cells in these cultures may be substituted with matrigel- or laminin-coated plates using conditioned medium from mouse embryonic fibroblasts. In important embodiments, the culture conditions exclude the use of animal products such as animal serum and/or mouse feeder cells. In some instances, the serum is human rather than animal serum.

Differentiation of ES cells is typically achieved via induction of EB formation. The Examples describe the differentiation of ES cells into the cardiac lineage through EB formation. Briefly, this method involves dispersing ES cells into a single cell suspension of ES cell medium lacking LIF, followed by culture in hanging drops for 2 days. EB generation via the hanging drop method may employ DMEM with 10% FBS either in the presence or absence of ascorbic acid. The hanging drop method is preferred to the extent that it provides better control and uniformity in size and shape.

After 2 days of culture, the EBs are transferred into a culture vessel. As used herein, a culture vessel intends a flask, a plate, or a well (e.g., from a multi-well dish). Preferably, the culture vessel is coated with a substrate that promotes cell adhesion such as but not limited to gelatin, fibronectin, or laminin. In some embodiments, combinations of these substrates may be used. For example, in some instances it may be useful to coat the vessel with fibronectin followed by gelatin. The EBs are allowed to differentiate for 2, 3, 4, or more days with daily medium changes, followed by a change to a serum-free medium supplemented with ITS (see FIG. 1 legend) with or without 0.2 mM ascorbic acid. (See FIG. 11.) The cells may be cultured for an additional 5, 6, 7 or more days in these latter conditions. It is to be understood that the low $pO_2$ conditions of the instant invention can be imposed at the start of or during the EB formation step.

Differentiation of human ES cells can be achieved using the same hanging drop method procedure and the same medium as used for maintenance of undifferentiated ES cells except that bFGF is omitted.

In some embodiments, the EB-containing hanging drops are transferred into culture vessels having oxygen-permeable bottom membranes (e.g., oxygen-permeable silicone rubber membrane). These vessels may be constructed so as to replace their bottoms with these membranes. These membranes are preferably coated with substrates (e.g., proteins) that promote cell adhesion such as but not limited to gelatin, fibronectin or laminin. Combinations of these substrates may also be employed. For example, in some instances it may be useful to coat the vessel with a first substrate such as fibronectin followed by a second substrate such as gelatin, particularly if the second substrate does not adhere sufficiently to the bare membrane. The Examples demonstrate the use of culture vessels having silicone rubber bottom membranes coated with fibronectin. Importantly, the use of oxygen-permeable membranes such as those of the Examples eliminates the need for stirred or perfused culture systems, such as those used in the prior art. (Bauwens et al., Biotechnol Bioengin, 90(4):453-461, 2005).

It has been found according to some embodiments of the invention that increases in cardiomyocyte differentiation can be effected more rapidly using the hanging drop culture step and/or with prolonged exposure to serum.

Thus, in one aspect the invention contemplates that the low $pO_2$ is able to direct differentiation of ES cells into the cardiac lineage. This appears to occur even in the absence of exogenously added factors that are known to stimulate cardiac differentiation (i.e., cardiac lineage differentiation factors or agents). It is to be understood that the claimed methods however do not preclude the endogenous presence of such factors (e.g., if they are produced by the ES cells and/or their progeny during culture) or the exogenous addition of such factors. Factors (or agents) reported to stimulate cardiac differentiation include ascorbic acid, retinoic acid, nitric oxide, TGFβ-1, activin, FGF (e.g., FGF2), erythropoietin, BMP2, BMP-4, DMSO, noggin, and VEGF. The Examples demonstrate that cultures having ascorbic acid result in higher enrichment and yield of mesoderm cells (such as cardiomyocytes) and endoderm cells under certain conditions.

In some embodiments, the entire culture period is performed in the absence of serum (i.e., in a serum-free condition). In other embodiments, the ES cells are differentiated in the presence of serum for 1, 2, 3, 4, 5, 6, 7, 8 or more days followed by culture in the absence of serum (i.e., serum-free) for 1, 2, 3, 4, 5, 6, 7, 8 or more days. In some important embodiments, the switch occurs at day 6. In still other embodiments, the switch from serum to serum-free culture conditions coincides with the increase from low to higher oxygen partial pressures.

Progenitor and differentiated cells such as cardiac progenitors and cardiomyocytes can be enumerated from cultures using automated or manual counting techniques. Flow cytometry can be used to measure the number of progenitor and differentiated cells. The Examples describe such methods for cardiomyocytes or cardiac progenitors from an ES cell culture. The Examples also describe counting of cardiomyocytes by immunostaining and manual counting of tissue sections under a fluorescence microscope (Carl Zeiss, MicroImaging, HBO 100 W/2).

As used herein, cardiac progenitors are cells that have committed to the cardiac lineage but which still exhibit substantial proliferative and optionally differentiative capacity. One population of cardiac progenitors has an isl1+/Nkx2.5/flk-1+ phenotype. This population can be counted or extracted using flow cytometry and sorting. Another population of cardiac progenitors has a brachyury+/flk-1+ phenotype.

Flow cytometry can be used to detect and count cardiomyocytes and their progenitors using one or more cardiac lineage markers. The cardiac lineage marker preferably is specific to the cardiac lineage (i.e., expressed only in cells committed to the cardiac lineage). Non-specific markers may also be used in some instances. Typical cardiac lineage markers include but are not limited to brachyury, nkx2.5, cardiac troponin I, or α-myosin heavy chain (α-MHC), gata-4, atrial natriuretic protein (ANP), myosin light chain (MLC)-2v, β-myosin heavy chain (β-MHC), and connexin 43. The Examples and the following text demonstrate the use of MF-20, an anti-sarcomeric myosin heavy chain antibody (commercially available from DBHB, Iowa City, Iowa). It is to be understood that these methods can be readily applied to any other marker, provided a probe for such marker is available.

Cardiac progenitor or cardiomyocyte presence in the cultures of the invention may also be detected according to mRNA expression profiles. For example, the presence of these cells may be determined by the presence of brachyury, nkx2.5, cardiac troponin I, or α-myosin heavy chain (α-MHC), gata-4, atrial natriuretic protein (ANP), myosin light chain (MLC)-2v, β-myosin heavy chain (β-MHC), and connexin 43 mRNA transcripts within cultured cell populations. Methods for detecting mRNA transcripts from differentiated ES cell populations (including cultured populations) are known in the art.

Endoderm progenitors that contribute to pancreatic development may be characterized by their gene expression profiles also. Stage 1 (definitive endoderm (DE) progenitor cells) express SOX17, CER, FOXA2, and CXCR4 and cells transitioning from ES cells to DE cells express BRA, FDF4, WNT3 and NCAD. Stage 2 endoderm progenitors express HNF1B and HNF4A. Stage 3 endoderm progenitors express PDX1, HNF6 and HLXB9. Stage 4 endoderm progenitors express NKX6-1, NGN3, PAX4 and NKX2-2. And finally stage 5 endoderm progenitors express INS, CGC, GHRL, SST and PPY.

The differentiated cells produced according to the invention can be used in a variety of in vivo and in vitro methods and processes including but not limited to in vivo therapeutic and cosmetic applications, and in vitro screening methods.

Progenitor and/or differentiated cells produced according to the invention can be transplanted into subjects in a variety of regenerative medicine therapies. As an example, cardiomyocytes and/or their progenitors may be transplanted in the treatment of cardiovascular disease. The cells may be autologous (e.g., in the instance where induced pluripotent stem cells are differentiated) or MHC-matched to donor subjects. The differentiated cells can be administered to subjects alone or in combination with another active agent or in some embodiments an inactive agent. Examples include scaffolds that may function simply as a structural support for the cells to be administered.

Progenitor and/or differentiated cells produced according to the invention may also be studied for gene expression profiles and responses to various external stimuli in order to understand mesoderm and/or endoderm differentiation more fully.

The invention further provides methods for screening agents (or compounds, as the terms are used interchangeably herein) for toxicity and in some embodiments therapeutic efficacy. The readouts from such in vitro assays are correlative of the in vivo toxicity or efficacy such agents would exhibit in human subjects. Thus, the effect of the agent on the differentiated cells generated according to the invention in vitro is a form of surrogate marker or readout for how the agent will function in vivo in a human subject. The agents to be tested include those used clinically as well as experimental agents. In some more common embodiments, such testing will focus on the toxicity of agents including drugs in particular differentiated progeny. Accordingly, in these assays, the readout would be cell death (or conversely cell viability). These in vitro assays may employ suspensions of differentiated cells, adherent populations of differentiated cells, or three dimensional structures comprised of differentiated cells (e.g., in vitro organ tissues, matrices and architectures).

The differentiated cells may be formulated as pharmaceutical compositions that are sterile and appropriate for in vivo use. They may therefore be formulated in pharmaceutically acceptable carriers, with which the art is familiar. They may further be included in a kit that additionally comprises at a minimum instructions for use of the cells, and optionally comprises one or more other agents whether active or inactive.

The present invention is further illustrated by the following Examples, which in no way should be construed as further limiting.

EXAMPLES

Example 1

Introduction

Most ES cell research is performed in incubators with a humidified 95% air/5% $CO_2$ gas mixture, resulting in a gas-phase oxygen partial pressure ($pO_{2gas}$) of 142 mmHg. Embryonic cells in early development are exposed to $pO_{2cell}$ values of about 0-30 mmHg, and the effects of such conditions on differentiating ES cells are poorly understood. It is now shown that control of the $pO_{2cell}$ to levels experienced by developing embryos enhances differentiation of ES cells into cardiomyocytes. The fraction of cells that are cardiomyocytes is maximized by initial culture at $pO_{2cell}$ values less than 7 mmHg, whereas cardiomyocyte number is maximized by subsequent culture at high $pO_{2cell}$. Under the best conditions examined, the fraction and number of cardiomyocytes increases 3-fold compared to culture at high $pO_{2cell}$ throughout differentiation. These results demonstrate that $pO_{2cell}$ is an important factor for enhancing directed differentiation of ES cells into cardiomyocytes for therapeutic applications. It may also be useful for differentiation into other cell types, and it likely plays a more important role in embryonic development than heretofore appreciated.

Low $pO_{2cell}$ conditions are generally thought to affect cells cultured in vitro by decreasing the exposure to reactive species generated by cellular respiration and regulating the stability of the oxygen-responsive transcription'factor HIF-1α, but other mechanisms may also be involved. Some cells are known to preferentially grow at low $pO_{2gas}$ conditions rather than the standard 142 mmHg, including fibroblasts, muscle satellite, hematopoietic, mesenchymal, and neural stem cells. Previous studies with undifferentiated ES cells have shown some improvement in survival and cloning efficiency using reduced $pO_{2gas}$ conditions, but most of the observed effects have been relatively minor. ES cell differentiation studies that show strong effects of low $pO_{2gas}$ conditions have been limited to hematopoietic differentiation, but the complex changes that occur during differentiation suggest that many differentiation pathways are likely to be affected by $pO_{2cell}$ conditions.

Cardiomyocytes spontaneously appear with relatively low frequency when ES cells are differentiated in the form of aggregates. Various molecules direct this differentiation further, including retinoic acid, nitric oxide, TGFβ-1, FGF, erythropoietin, BMP-2, BMP-4, ascorbic acid, retinoic acid, DMSO, noggin, 5-azacytidine, and VEGF. Previous work in a stirred system showed that reduced oxygen had a small positive effect that was observed only after genetic selection for cardiomyocytes was performed.

Materials and Methods:

Undifferentiated ES cell culture. J1 and R1 ES cells were obtained from ATCC (SCRC 1010, SCRC 1036, Manassaas, Va.), expanded on Mitomycin-C treated MEF cells, and frozen into vials following ATCC protocols. Vials were thawed into undifferentiated ES cell maintenance medium (described in Table 1) containing supplemental leukaemia inhibitory factor (LIF) and plated at a density of about $5\times10^4$ cell/$cm^2$ on 25 $cm^2$ cell culture flasks (353109, Becton Dickinson, Franklin Lakes, N.J.) that were treated for 30 min with a sterile 0.1% (w/v) solution of gelatine (G-2500, Sigma-Aldrich, St. Louis, Mo.) in tissue culture water (WFI, 25-055-CM, Mediatech, Herndon, Va.). Medium (Table 1) was exchanged daily, and cells were detached with 0.25% trypsin (30-2101, ATCC) every two days. Split fractions were chosen so that cells were plated at approximately $1.2^4 \times 10$ cells/$cm^2$. Cells were used for differentiation experiments 4-6 days after thawing the cell vials.

EB formation. Cell suspensions obtained after trypsin detachment of undifferentiated ES cells were centrifuged at 300×g for 3 min, supernatant medium was removed, and cells were resuspended in ES cell differentiation medium (Table 1) that did not contain supplemental LIF. The concentration of cells with intact membranes was determined using trypan blue cell counts, and cells were diluted to a concentration of $2.5\times10^4$ membrane-intact cells/ml. 20-0 drops of this cell suspension were aliquoted onto the inside surface of the lids of 10×10 cm Petri dishes (351112, Becton Dickinson) using an 8-channel pipette. The lids were inverted and placed onto the bottoms of the dishes, which were filled with 15 ml of a pre-warmed (37° C.) solution containing 75% (v/v) Dulbecco's phosphate buffered saline (DPBS, 21-030-CM, Mediatech), 25% water, and 0.002% (w/v) gelatine.

EB transfer. After 2 days in hanging drops, the resulting EBs were manually pipetted off of the Petri dish lid using wide-orifice pipette tips (3532, Molecular BioProducts, San Diego, Calif.) and placed into the wells of custom-made 24-well culture dish, which had the plastic bottom replaced with fibronectin-coated silicone rubber membrane. 30 EBs were placed into each well, and the medium was mixed by pipetting to distribute the EBs uniformly across the plate bottom.

Culture of attached EBs. The EBs attached and spread within one day of transfer to the silicone rubber membrane-based dish. The medium was removed from all of the wells 2 days after EB transfer and was replaced with 1 ml of fresh ES cell differentiation medium. On the following day, the medium was removed and replaced with 1 ml serum-free differentiation medium (Table 2). Medium continued to be exchanged daily with the serum-free differentiation medium until the end of the experiment.

Cell collection for nuclei counting and flow cytometry. At the end of the experiments (8 or 9 days after transferring EBs), the medium was removed from the wells of the 24-well silicone rubber membrane-based culture dish, the cells were washed with DPBS, and 200 μl of trypsin solution was added to each well. After a 5-min incubation at 37° C., 800 μl of ES cell differentiation medium was added to each well. The contents of the well were vigorously pipetted using a 1 ml pipette to dislodge and disperse the cells and were then transferred to a 1 ml tube. The contents were allowed to settle for 2 min, then the bottom 50 μl that contained any large clumps of cells and extra-cellular matrix were removed and discarded (or saved for later analysis). The cell sample was then mixed briefly with a vortex mixer, and a 50 μl aliquot was removed, added to 450 μl of lysis solution containing 1% Triton X-100 (T9284, Sigma Aldrich) and 0.1 M citric acid (C1909, Sigma Aldrich) in DI water to liberate nuclei, and saved for later analysis. The remaining 900 μl of cell sample was centrifuged at 300×g for 3 min, and the supernatant medium was discarded. Cells were resuspended in 750 p. 1 DPBS, 250 ml of 4% (w/v) paraformaldehyde (Alfa Aesar, Ward Hill, Mass.) in DPBS was added to fix the cells, and each sample was incubated for 20 min at room temperature. The samples were then centrifuged at 300×g, the supernatant removed, and 1 ml of DPBS was added. Samples of nuclei and fixed cells were stored at 4° C. prior to analysis. The higher fraction of MF-20$^+$ cells measured with flow cytometry compared to immunohistochemical identification (FIG. 1C) suggests that the cell clumps that were discarded contained fewer cardiomyocytes than the cells that were retained.

Nuclei enumeration. Samples were stained using a Guava Viacount assay kit (Guava Technologies, Hayward, Calif.) and data were acquired with a Guava PCA flow cytometer.

Flow cytometry. Samples with $3 \times 10^5$ fixed cells were removed from the fixed cell sample tubes, added to an equal volume of 1% (w/v) saponin (S-4521, Sigma-Aldrich), and incubated for 10 min to allow for cell permeabilization. Subsequently, the cells were washed and resuspended in 50 µl of 2% (v/v) FBS in PBS. Samples were incubated in the 2% FBS solution for 30 min, and then 5 µl of diluted primary antibody was added. Primary antibodies were anti-sarcomeric myosin heavy chain (MF-20, MF-20 supernatant, Developmental Studies Hybridoma Bank, Iowa City, Iowa) without dilution and anti-cardiac troponin T (anti-cTnT, MS-295-P, Lab Vision Corp., Fremont, Calif.) diluted 1:10. Samples were incubated with the primary antibody for 1 hr, then 0.5 ml of 2% FBS solution was added to each tube, and the samples were centrifuged. The supernatant was discarded, and the cells were resuspended in 50 µl of goat anti-mouse phycoerythrin-conjugated secondary antibody (115-116-146, Jackson ImmunoResearch, West Grove, Pa.) diluted 1:250 in 2% FBS. The samples were incubated for 30 min in the dark, washed twice with 0.5 ml of PBS, and fluorescence intensity data were acquired using a flow cytometer (Guava Technologies) using the Express software module. All steps were performed at room temperature.

Cell processing for histology. At the end of the experiments (8 or 9 days after transferring EBs), the medium was removed from the wells of the 24-well silicone rubber membrane-based culture dish, and the cells were washed with DPBS and incubated for 30 min at room temperature with 4% (w/v) paraformaldehyde solution. The sheet of cells was then washed twice with 1 ml of DPBS, released from the dish bottom by stretching the silicone rubber membrane, and transferred into a 1.5 ml microtube. The tube was centrifuged at 300×g, and all but 100 µl of the DPBS was removed. A 900-0 aliquot of 1% (w/v) agarose (5510UA, Life Technologies, Gaithersburg, Md.) in DI water (at 95° C.) was added to the tubes, which were briefly mixed by vortexing. Samples were then centrifuged for 1 min at 20,000×g and cooled for 1 hr at 4° C. A 500-µl volume of 4% (w/v) paraformaldehyde solution was added to the tubes, which were stored overnight. The agarose was removed from the tube on the following day and trimmed with a razor blade so that only the pellet and a small additional amount of agarose remained. The pellets were then placed in histology cassettes and stored in DPBS prior to embedding. Histology specimens were embedded in paraffin and sectioned by the Joslin Diabetes Center histology core following standard protocols to yield 5-µm sections.

Immunocytochemistry of sectioned tissue. Slides containing the 5-µm sections were deparaffinized and rehydrated by 7-mM rinses with xylene (twice), 5-mM rinses with 100% ethanol (twice), a 3-min rinse with 95% ethanol, a 10-min rinse with 70% ethanol, and 5-min rinses with deionized (DI) water (twice). Antigen retrieval was performed by boiling the sections for 10 mM in a 10 mM sodium citrate (0754, Mallinckrodt, Paris, Ky.) solution adjusted to pH 6. The slides were cooled to room temperature, and endogenous peroxidase activity was quenched by incubating the slides for 10 mM in a solution containing 0.3% hydrogen peroxide (386790, Calbiochem, La Jolla, Calif.) in DI water. Slides were then incubated for 1 hr in a solution containing 1% FBS in PBS and subsequently incubated with diluted primary antibody overnight at 4° C. (1:10 dilution of MF-20 and 1:100 dilution of anti-cTnT). After washing 3 times with 1% FBS in PBS, goat anti-mouse IgG (115-035-062, Jackson ImmunoResearch) diluted 1:50 in 1% FBS was added, and the slides were incubated for 3 hr at room temperature. The slides were then washed 3 more times, a mouse peroxidase-anti-peroxidase complex (223-005-024, Jackson ImmunoResearch) diluted 1:500 in 1% FBS was added, and an additional 1-hr incubation at room temperature was performed. After washing twice in PBS, antibody binding was visualized by incubating 2 mM in a 2 mM solution of diaminobenzidine (D5637, Sigma Aldrich) containing 0.015% hydrogen peroxide. Slides were then counterstained by incubating for 15 sec in filtered haematoxylin (HHS16, Sigma Aldrich), followed by 3 subsequent washes in 30 mM sodium borate (B10267-34, EMD, Gibbstown, N.J.). Slides were then dehydrated following the reverse procedure for rehydration and were preserved using Permount (SP15, Fisher Chemical, Fair-Lawn, N.J.). Slides were photographed, and 1000 total cells in at least 20 different randomly selected 5500 µm$^2$ areas (coordinates of photograph selected with a random number generator in Excel) of the section were examined for immunostaining, and positive and negative cells were counted to determine the number fraction of cell positively immunostained with MF-20.

Silicone rubber membrane-based dishes. Most of the bottom surface of the 8 central wells of 24-well tissue culture plates (353047, Becton Dickinson) was removed using a ⅜×3 inch fixed handle nutdriver (12, Cooper Hand Tools, Apex, N.C.) heated in a Bunsen burner to melt a hole in the plastic. A sterile scalpel was used to thin the edges of the holes. A very thin layer of silicone adhesive (59530, Henkel Loctite Corp., Rocky Hill, Conn.) was spread around each of the holes. A rectangular 8.5×4.5 cm piece of silicone rubber membrane (non-reinforced vulcanized gloss/gloss 0.005 inch, Specialty Manufacturing, Saginaw, Mich.), previously sterilized by autoclaving, was placed over the holes and manually pressed and stretched so that the silicone sheet was flat (no wrinkles) and sealed onto the plate bottom. After allowing the adhesive to cure for 24 hr, the plates were completely filled with a 70% ethanol solution for 1 hr and dried overnight under a germicidal UV lamp in a biological safety cabinet. One day prior to plating the cells, 1 ml of 2-µg/ml fibronectin (F1141, Sigma-Aldrich) in DPBS was added to each well and incubated overnight at 37° C. Immediately before plating cells, the fibronectin solution was removed from all of the wells and replaced with 1 ml pre-warmed ES cell differentiation medium.

Gas phase $pO_2$ control. Cell culture vessels were placed inside sealed polystyrene chambers (MIC-101, Billups-Rothenburg, Del Mar, Calif.) that were housed inside a standard incubator (OWJ2720A, Queue Systems, Parkersburg, W. Va.) maintained at 37° C. The desired $pO_{2gas}$ was established and maintained using premixed gas containing 5% $CO_2$ and 20%, 5%, or 1% oxygen (certified medical gas from Airgas, Hingham, Mass.). The flow rate of gas to the chambers was 2 l/min for 15 min for an initial purge following closure of the chamber (after cell medium exchange) and 30 ml/min at all other times. Gas was bubbled through a sealed bottle of water (in the incubator), and an open dish of deionized water in each chamber provided additional humidification.

Model for oxygen reaction and diffusion. A theoretical model of oxygen consumption and diffusion in the culture system was developed in order to describe the oxygen concentration in the tissue. Oxygen transport within the medium, silicone rubber membrane, and tissue was modeled using the oxygen conservation equation $$D\alpha \nabla^2 (pO_2) = R_v \quad (1)$$

where D and $\alpha$ are the effective diffusivity and solubility, respectively, of oxygen in the medium, silicone rubber membrane, or the tissue, and $R_v$ is the volumetric oxygen consumption rate within the tissue and is equal to 0 in the medium and the silicone rubber. The boundary conditions for the model were $pO_2 = pO_{2gas}$ at the gas/liquid and gas/silicone rubber interfaces and $\nabla pO_2 = 0$ at the edge of the unit well used for simulation. Continuity of flux and $pO_2$ were assumed at the silicone rubber/medium, silicone rubber/tissue, and medium/tissue interfaces. The product of the diffusivity and solubility of oxygen in culture medium, silicone rubber, and tissue was taken to be 3.53, 26.3, and $1.34 \times 10^{-15}$ mol/cm mmHg sec, respectively.

Determination of volumetric oxygen consumption rate. The volumetric oxygen consumption rate, $R_v$ (amol/sec cm$^3$), in the tissue was assumed to follow Michaelis-Menten kinetics, $$R_V = V_{max} \left[ \frac{pO_2}{K_m + pO_2} \right] \left[ \frac{1}{V_{cell}} \right] \quad (2)$$

where $V_{max}$ is the maximal oxygen consumption rate (amol/cell sec), $K_m$ is the Michaelis constant, which was taken to be 0.44 mmHg, and $V_{cell}$ is the average volume of tissue associated with each cell, which includes the actual cell volume and associated interstitial volume.

$V_{max}$ was measured with undifferentiated ES cells, whole EBs cultured for 3 days, and for cells that had been differentiated for 10 days according to the cardiomyocyte differentiation protocol. To measure $V_{max}$, cells or tissue were put in fresh culture medium equilibrated to 37° C. and ambient oxygen and then placed into a Micro Oxygen Monitoring System (FO/SYS2-T250, Instech Labs, Plymouth Meeting, Pa.) as described previously. Undifferentiated cells were detached with trypsin and resuspended at a density of between 6 and $12 \times 10^6$ viable cells/ml and placed in the chamber. With day 3 EBs, 100 EBs were removed from hanging drop culture after 3 days and pipetted into the OCR measurement chamber, allowed to settle for 5 min, and excess medium was removed. After 10 days of differentiation, the cell sheets and clumps were released from the dish bottom by stretching the silicone rubber membrane, transferred into the OCR measurement chamber, allowed to settle 1 min, and excess medium was removed. The chamber was then sealed and the measurement was performed. The time-dependent $pO_2$ within the chamber was recorded with a fluorescence-based oxygen sensor, and the data at $pO_2$ values greater than 30 mmHg were fit to a straight line by linear regression analysis. The oxygen consumption rate (OCR) was evaluated from the slope of this line, and $V_{max}$ was determined by dividing the total OCR by the total number cells in the chamber, as determined by nuclei counting. Measured values of $V_{max}$ varied with $pO_2$ (FIG. 2). The data were fit to a function of the form $$V_{max} = \alpha + \beta \left[ \frac{pO_2}{\gamma + pO_2} \right] \quad (3)$$

yielding $\alpha$ and $\beta = 10$ and 20 amol/sec cell, respectively, and $\gamma = 16$ mmHg.

$V_{cell}$ was determined with day 2 EBs by measuring the diameter using light microscopy and a calibrated reticule, then dissociating the EBs to obtain total nuclei counts, $n_c$. $V_{cell}$ was calculated from the ratio $V_{EB}/n_c$, where $V_{EB}$ is total volume of EBs analyzed, to obtain $V_{cell} = 10.1 \pm 1.1$, $11.2 \pm 1.4$, and $12.7 \pm 1.5 \times 10^{-10}$ cm$^3$/cell after 2 days at $pO_{2gas}$ of 7, 36, and 142 mmHg, respectively. For cells after 11 days of differentiation, a field of view encompassing aggregated cells in a 5-t µm tissue section was identified using light microscopy. The number of cells per unit volume of tissue was assumed to be equal to the number of nuclei having their centre within this volume. It was assumed that the nuclei were spheres with a diameter, d, of 7 µm, and the number of nuclei counted in the section of thickness, t=5 µm, was multiplied by the ratio of t/(t+d) to obtain the number of nuclei, $n_e$, whose centre point was within the volume of tissue contained in the section. $V_{cell}$ was calculated from the ratio $V_{sec}/n_c$, where $V_{sec} = A_{FOV}t$, and $A_{FOV}$ is the area of the field of view. Data for cells after 11 days of differentiation from 15 fields of view were averaged, yielding $V_{cell} = 15 \pm 4$, $14 \pm 6$, and $14 \pm 7 \times 10^{-10}$ cm$^3$ after at $pO_{2gas}$ of 7, 36, and 142 mmHg, respectively. The volume of tissue associated with each cell varied significantly within different regions of the tissue and this heterogeneity was not considered in the analysis.

Geometric properties of cultured tissue. To accurately model the oxygen consumption and diffusion, the geometric properties of the tissue were measured with light microscopy. The 2-day EBs were nearly perfect spheres with average radii of $99 \pm 6$, $115 \pm 5$, and $114 \pm 8$ µm for $pO_{2gas}$ of 7, 36, and 142 mmHg, respectively. To characterize the tissue after 10 or 11 days in culture, 5-µm tissue sections taken from three Independent experiments were analyzed by stereological point counting using at least 300 points from each of the 5-µm tissue sections. The tissue was present in the form of thin sheets or larger clumps of cells, and the volume fraction of tissue in each morphology was determined. The fraction of tissue in clumps was $53 \pm 6$, $75 \pm 9$, and $90 \pm 7\%$ of the total tissue volume for cells cultured at $pO_{2gas}$ of 7, 36, and 142 mmHg, respectively. For each clump of cells examined, the distance from the basal to apical surface (tissue thickness) and the length of the clump was recorded (Table 3). Each clump was modelled as an oblate hemispheroid with major and minor axis that corresponded to the measured height and half width, respectively. The sheet-like tissue was modelled as an infinite thin slab with a thickness of 30, 30, and 15 µm at $pO_{2gas}$ of 142, 36, and 7 mmHg, respectively, based on measurements of representative cell sheets; the range of predicted $pO_{2cell}$ values in the cell sheets was small and insensitive to minor variations in sheet thickness in the range of 0-30 µm.

Finite element model. The tissue geometries described above were modelled as resting on the surface of a 127-µm thick silicone rubber membrane overlain with a 5 mm height of medium and placed in the centre of a cylindrical well with a 2 mm radius, a size at which edge effects due to the well walls were negligible. Eqn. (1) with the appropriate parameters and boundary conditions described above was solved for each individual clump geometry using a numerical finite element method (Comsol Multiphysics). Because each clump was assumed to be axisymmetric, the model was solved in two dimensions.

Tissue distribution of oxygen on day 11 tissue. The calculations described above yielded the distribution of $pO_2$ throughout each of the individual hemispheroidal and planar tissue geometries that was analyzed. For each geometry simulated, surfaces of constant $pO_2$ were determined, and numerical integration was performed to determine the volume of tissue between the surfaces of constant $pO_2$ within the axisymmetric clump. The volume fraction of tissue within specific limits of $pO_2$ in the entire dish, consisting of a sheet with a single average thickness and each of the individual clumps, was determined from $$\Phi_{ab} = [(\phi_{sheet})(\Phi_{ab,sheet})] + \phi_{clump} \frac{\sum_{j=1}^{n} V_{ab,j}}{\sum_{j=1}^{n} V_{clump,j}} \quad (4)$$

where $\Phi_{ab}$ is the total volume fraction with a $pO_2$ between a and b, $\Phi_{ab,sheet}$ is the comparable quantity for the tissue in the cell sheet, $\phi_{sheet}$ and $\phi_{clump}$ are the volume fractions of tissue in the total preparation in the sheet and clump geometry, respectively, $V_{ab,j}$ is the volume of tissue with a $pO_2$ between a and b in the $j^{th}$ clump of cells, and $V_{clump,j}$ is the total volume of all of the tissue in the $j^{th}$ clump.

Tissue distribution of oxygen within MF-20$^+$ region. Calculations similar to those described above were used to estimate the oxygenation of the cells positively immunostained with MF-20. For these simulations the aggregate dimensions were measured and MF-20$^+$ regions were identified in the 5-1 μm tissue sections. The finite element model for oxygen transport was used to predict the $pO_2$ profile within the entire clump, and the integration to determine the volume of tissue between surfaces of constant $pO_2$ was only performed for simulated MF-20$^+$ regions. The volume fraction of tissue in MF-20$^+$ regions within specific limits of $pO_2$ was determined using an equation analogous to Eqn (4)

$$\Phi_{ab,MF20} = \frac{\sum_{j=1}^{n} V_{ab,j,MF20}}{\sum_{j=1}^{n} V_{clump,j,MF20}} \quad (5)$$

where $V_{ab,j,MF20}$ is the volume of tissue with a $pO_2$ between a and b in the $j^{th}$ MF-20$^+$ region and $V_{clump,j,MF20}$ is the total volume of the $j^{th}$ MF-20 positive region. Because no MF-20$^+$ cells were observed in the sheet like morphology, $\phi_{sheet}$ was set to 0 and does not appear in Eqn 5.

Statistics. Statistical analysis was performed using paired two-tailed t-tests in Microsoft Excel.

Results and Discussion:

In a static, attached culture system reported here, reduced oxygen resulted in a significant increase in differentiation of mES cells into cardiomyocytes, which could be further enhanced with supplemental ascorbic acid. In the present studies, EBs were formed in hanging drops for 2 days and then manually transferred to custom-made culture dishes having fibronectin-coated silicone rubber membranes at the bottom, to which the cells attached and grew. The silicone rubber membranes had very high permeability to oxygen that allowed use of static culture while retaining control of $pO_{2cell}$ at the membrane-cell interface to values similar to $pO_{2gas}$. These dishes were used to quantitatively study the effect of oxygen on ES cell differentiation into cardiomyocytes by differentiating the cells for 10 or 11 days in the presence of ascorbic acid, immunostaining cells with monoclonal antibodies to sarcomeric myosin (MF-20) and cardiac troponin T (anti-cTnT), and counting immunostained cells with either a flow cytometer or manually using light microscopy to examine sectioned tissue.

Figure 1A:
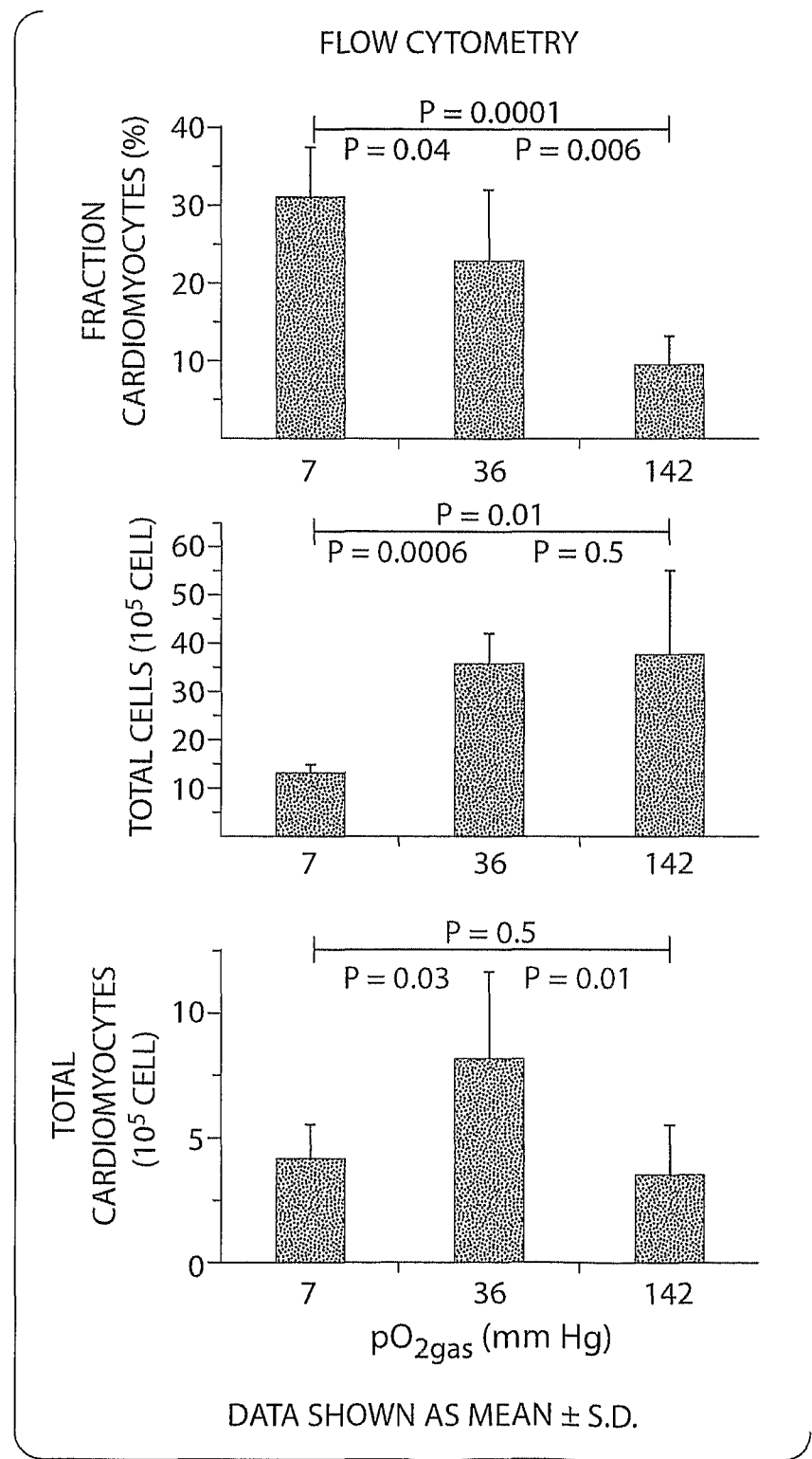
FIG. 1. $pO_2$ affects differentiation into cardiomyocytes. J1 mES cells were differentiated in hanging drops containing 500 cells using DMEM with 10% FBS. After 2 days the drops were transferred into a fibronectin-coated, silicone rubber membrane-bottomed, 24-well plate. Three days later, the medium was changed to a serum-free insulin-transferrin-sodium selenite (ITS) medium. Media were exchanged daily after plating of cells, and the $pO_{2gas}$ was controlled using premixed gas cylinders that supplied modular incubators. Details of reagents and protocols are provided in the Examples.

Differentiating mES cells at different, constant $pO_{2gas}$ conditions for 10 or 11 days resulted in a large increase in the fraction of cells that were cardiomyocytes with decreasing values of $pO_{2gas}$ (FIG. 1A). The highest number fraction of cardiomyocytes (MF-20$^+$ cells) was 31±6% (mean±s.d.) with a $pO_{2gas}$ of 7 mmHg, compared to 23±9% and 9±4% at 36 and 142 mmHg, respectively. Culture at 7 mmHg resulted in a substantial decrease in total cell number relative to that at 36 or 142 mmHg, both of which had comparable cell numbers after 11 days. As a result, the total number of cardiomyocytes was similar at 7 and 142 mmHg but significantly higher at 36 mmHg.

Figure 1B:
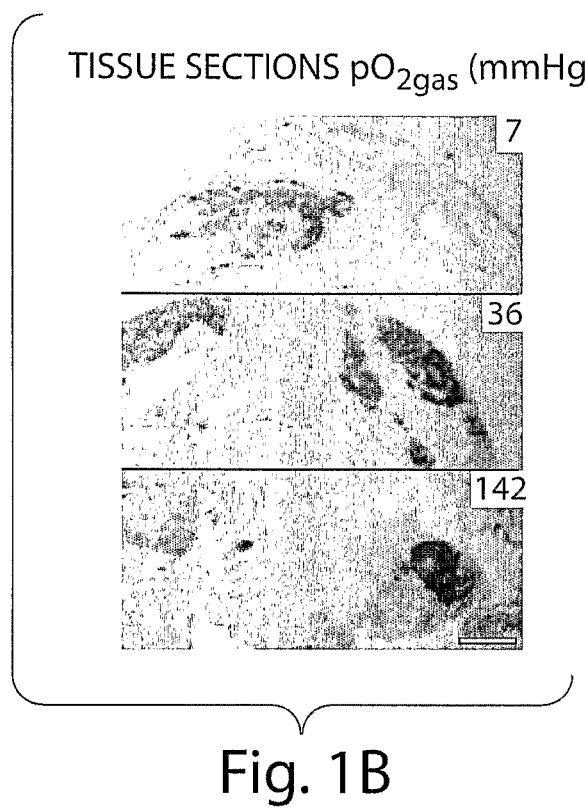
Figure 1C:
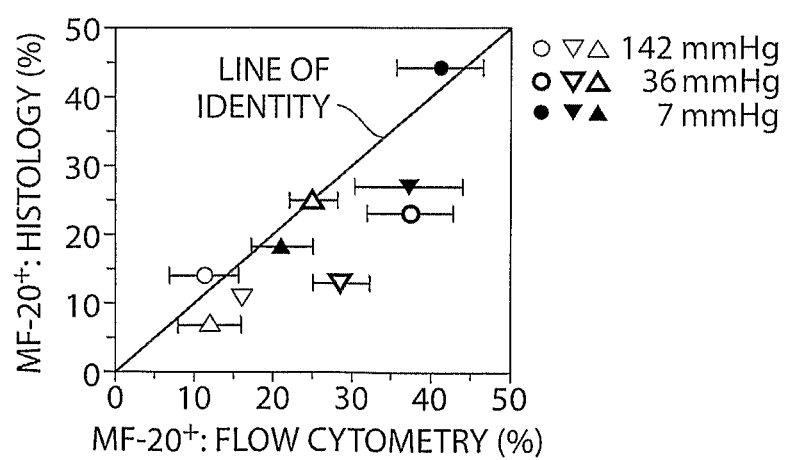

Histological examination of 5-μm tissue sections showed that cells cultured for 11 days at 7 mmHg preferentially formed thin cell sheets and smaller aggregates than were found at 36 or 142 mmHg (FIG. 1B). In all cases MF-20$^+$ cells were found together in aggregates. Flow cytometry produced slightly higher estimates for positive cell fraction than histological counting (FIG. 1C), but the increase in cardiomyocyte fraction with decreasing $pO_{2gas}$ was observed using both methods for quantification. Co-localization of MF-20 and anti-cTnT immunostaining was also observed (FIG. 3), and there was a strong correlation between the total number of MF-20$^+$ cells and the area covered by spontaneously contracting cells (FIG. 4).

The 10% cardiomyocyte purity observed at 142 mmHg without cell purification is comparable to results obtained by others using optimized differentiation protocols; the present protocol was one such variation that used supplemental ascorbic acid and serum removal after day 5 to enhance cardiomyogenesis. An increased fraction of cardiomyocytes was observed with decreased $pO_{2gas}$ using differentiation protocols without additional ascorbic acid and with removal of serum at different times. However, use of reduced $pO_{2gas}$ values with these sub-optimal protocols did not produce a high fraction of cardiomyocytes (Table 4).

The effect of culturing cells at high and low $pO_{2gas}$ for different time periods in different order with the total culture period held constant was also examined (FIG. 5). After 10 days in culture, the fraction of cells that were cardiomyocytes was greater when the cells were initially started at 7 mmHg, while the total cell number was greatest when cells were ended at 142 mmHg. As a consequence, in these experiments the total cardiomyocyte number was highest when cultures were grown for 6 days at 7 mmHg, then switched to 142 mmHg. Using these $pO_{2gas}$ conditions, 35% of cells were cardiomyocytes, and 60 cardiomyocytes were generated for each initial ES cell, both of which represented a 3-fold increase relative to constant culture at 142 mmHg.

In similar experiments in which ES cells were initially cultured in 36 mmHg $pO_2$ for 6 days and then moved to 142 mmHg $pO_2$ for another 15 days, 304 cardiomyocytes were generated for each initial ES cell. This represented a 5-fold increase in the proportion of cardiomyocytes and a 9-fold increase in the total number of cardiomyocytes relative to constant culture at 142 mmHg.

The first spontaneously-contracting and MF-20+ cells appeared at approximately the sixth day of culture in these experiments or as late as the seventh day at a $pO_{2gas}$ of 7 mmHg. Because oxygen exerted its strongest effects on differentiation during times preceding the appearance of cardiomyocytes, it can be inferred that oxygen affected differentiation into cardiomyocyte progenitor cells and/or induced an increase in proliferation of such progenitor cells relative to other cell types. The increase in total cardiomyocyte number suggests a direct positive effect of reduced oxygen on differentiation or proliferation along the cardiomyocyte lineage.

In addition to immunostaining samples with MF-20, serial tissue sections immunostained with anti-cTnT exhibited excellent co-localization of these two cardiac markers (FIG. 3). The total number of cardiomyocytes determined by counting MF-20 immunostained cells after trypsin dissociation was also correlated with the total area covered by spontaneously contracting cells, which was determined by visual estimation, with a correlation coefficient of 0.8 (FIG. 4). This correlation with a functional assay (spontaneous contraction) verified that the immunostaining procedure identified functional cardiomyocytes.

Experiments were performed with a less effective protocol that used 200 cells for EB formation (instead of 500), had the EBs cultured in hanging drops for 4 days before being transferred directly into serum-free ITS medium (instead of 2 days in hanging drops and change to ITS medium on day 5), and were done mostly without supplemental ascorbic acid (Table 4). There was an increase in the fraction of cardiomyocytes formed at a $pO_{2gas}$ of 36 relative to 142 mmHg that was highly significant both with (P=0.03) and without (P=0.005) supplemental ascorbic acid. Without ascorbic acid, there was a marginally significant increase in the fraction of cardiomyocytes at 36 relative to 7 mmHg (P=0.06), and at 7 relative to 142 mmHg (P=0.08). There was also a highly significant increase in the fraction of cardiomyocytes obtained when ascorbic acid was included in the culture medium for all of the oxygen conditions tested (P=0.0005). In these experiments there were fewer total cardiomyocytes.

The effect of maintaining the cells in high-glucose DMEM with 10% FBS for the duration of the experiments was also examined (FIG. 6). Culture in DMEM throughout the experiment did not affect the total cell number, but resulted in a reduced fraction of cells that were cardiomyocytes (and hence fewer total cardiomyocytes) in all $pO_{2gas}$ conditions relative to cultures that were transferred to serum free ITS medium on day 5. The highest fraction and total number of cardiomyocytes were obtained at $pO_{2gas}$ conditions of 7 and 36 mmHg, respectively, both with and without a change to ITS medium on day 5.

Silicone rubber membranes that are 127-μm thick and that have high oxygen permeability were used as the bottom of the culture dishes in order to control the $pO_{2cell}$ of cells attached to the bottom of the dish. Nonetheless, the presence of large cellular aggregates that formed due to cell growth after EBs attached to the fibronectin-coated silicone rubber (FIG. 1B) suggested that substantial gradients of $pO_{2cell}$ could exist. A theoretical model of oxygen consumption and diffusion was used to estimate the volumetric distribution of $pO_{2cell}$ within the aggregates (FIG. 7). In 2-day EBs, about 60% of the tissue was at a $pO_{2cell}$ less than 1 mmHg during culture at a $pO_{2gas}$ of 7 mmHg, whereas more than 80% of tissue cultured at 36 mmHg was at a $pO_{cell}$ greater than 7 mmHg, and all of the tissue at 142 mmHg was at a $pO_{2cell}$ greater than 94 mmHg. After 2 days, the EBs attached, spread, and further proliferated on the silicone rubber membrane; the idealized spherical geometry was lost, and approximations of aggregate shapes were used in the model. After 11 days there were areas of oxygen starvation under all conditions because of large aggregate sizes; at a $pO_{2gas}$ of 142 mmHg, about 25% of the tissue was at a $pO_{2cell}$ less than 7 mmHg and 50% was less than 36 mmHg. Culture at local $pO_{2cell}$ values ranging from less than 1 mmHg to several 10 s of mmHg at early times substantially enhanced cardiomyocyte development. Some cardiomyocyte differentiation may have occurred at higher $pO_{2cell}$ conditions as suggested by the position of the MF-20+ cells within the aggregates (FIGS. 3 and 8).

Representative oxygen profiles within the cell aggregates (FIG. 9) show that the lowest $pO_2$ occurs in the middle of the aggregate, slightly above the actual center. The volumetric distribution in FIG. 7 is derived from the information in FIG. 9. By combining knowledge of the partial pressure profiles and volumetric distributions such as those in FIG. 7 and FIG. 9, respectively, with data on the location of the cardiomyocytes from immunostaining (FIG. 1B), it was possible to predict the local $pO_{cell}$ of the cardiomyocytes. A comparison of the volumetric distribution of $pO_{2cell}$ of all of the aggregated tissue during culture and that of cardiomyocytes at 142 mmHg is shown in FIG. 8. The overall $pO_{2cell}$ distribution shows that cardiomyocytes are present at locations that cover the entire range of $pO_{2cell}$ values from 0.1 to 142 mmHg. Compared to the $pO_2$ distribution in the entire tissue volume, the cardiomyocytes appear to be preferentially located in regions of moderately low $pO_{2cell}$ in the range of 20-50 mmHg, and are present less frequently at regions of very low (less than 0.2 mmHg) or high (greater than 100 mmHg) $pO_2$.

In the experiments described herein, a higher fraction of cardiomyocytes was always observed in a $pO_{2gas}$ of 36 relative to 142 mmHg. This was true for a wide variety of different protocol variations with J1, R1, CCE, and D3 mES dell lines (data for CCE and D3 cells not shown). Cells cultured at a $pO_{2gas}$ of 7 mmHg were more sensitive to protocol changes, which may be due in part to nutrient limitations or excessive waste accumulation that can occur in this condition if medium is not replenished with sufficient frequency. Nonetheless, the positive effect that low $pO_2$ culture had on ES cell differentiation into cardiomyocytes using a variety of conditions suggests that the benefits of using reduced oxygen conditions are broadly applicable and not simply the result of using one or two specific differentiation protocols. A better understanding of the mechanism through which low oxygen exerts its effects might suggest medium additives or other protocol modifications that would simulate at high $pO_{2gas}$ the effects observed with low $pO_{2gas}$. Every experiment performed thus far has shown increased differentiation into cardiomyocytes at reduced $pO_{2gas}$ conditions.

The data from FIGS. 8 and 9 strongly suggest that some cardiomyocytes formed at high local $pO_{2cell}$ of 100 mmHg or greater. The day 2 EBs were well-oxygenated, and most of the tissue at day 10 and 11 was at a relatively high $pO_{2cell}$. Although there were regions of low $pO_{2cell}$ within the centre of the day 11 aggregates, they were almost certainly smaller or non-existent during the first 6 days of differentiation, when low oxygen exerts its most significant effects. Mature cardiomyocytes preferentially occupied regions of moderately low local $pO_2$ (FIG. 8); however, the $pO_{2cell}$ during the differentiation of these cells is unknown.

The mechanism by which oxygen exerted its effects in our experiments is not known. The oxygen-sensitive transcription factor HIF-1 is active in ES cells cultured at 142 mmHg, and its activity is further enhanced during low $pO_2$ culture. In a HIF-1α knockout ES cell line, no cardiomyocyte differentiation is observed in-vitro during culture at 142 mmHg, and HIF-1 activity is seen in hypoxic regions of the developing chick heart. HIF-1 therefore seems likely to be responsible for at least some of the effects observed in our experiments. HIF-1α target genes include all of the enzymes necessary for glycolysis as well as VEGF and other proteins. VEGF enhances cardiomyocyte differentiation of ES cells, but it alone does not appear to have a sufficient effect on differentiation to explain these results. Signaling through ROS has also been suggested to affect ES cell differentiation into cardiomyocytes, and some of these pathways appear to affect HIF-1α expression as well. As previously noted with the study of hematopoietic differentiation at low $pO_2$, the effects observed in the present study are likely the result of a combination of factors.

The present finding that the $pO_2$ to which ES cells are exposed during culture can profoundly influence differentiation into cardiomyocytes has disparate ramifications. The markedly increased yield of cardiomyocytes may enhance prospects for their therapeutic use in heart disease. Control of dissolved oxygen is inexpensive and easily accomplished in biotechnological processes, making our results applicable to commercial development of stem cell technologies. Reduced oxygen culture in combination with other proteins and small molecules may affect differentiation to other cell types. Because the cells in the early embryo are exposed to $pO_{2cell}$ conditions that lie within the range in which we observed large effects on differentiation, $pO_{2cell}$ may play a more important role in early embryonic development than heretofore appreciated.

Example 2

ES cells were differentiated on silicone rubber-bottom dishes, which are highly permeable to oxygen and allow for better control of $pO_2$ to the cells. When results were repeated on polystyrene dishes, no spontaneously beating cells were observed. Below are a list and explanation of relevant methods used in cell culture.

Materials and Methods:

Undifferentiated ES cell culture. J1 and R1ES cells were obtained from ATCC(SCRC 1010, SCRC 1036, Manassas, Va.), expanded on Mitomycin-C treated MEF cells, and frozen into vials following ATCC protocols. Vials were thawed into undifferentiated ES cell maintenance medium (described in Table 1) containing supplemental leukaemia inhibitory factor (LIF) and plated at a density of about $5\times10^4$ cell/cm² on 25 cm² cell culture flasks (353109, Becton Dickinson, Franklin Lakes, N.J.) that were treated for 30 min. with a sterile 0.1% (w/v) solution of gelatine (G-2500, Sigma-Aldrich, St. Louis, Mo.) in tissue culture water (WFI, 25-055-CM, Mediatech, Herndon, Va.). Medium (Table 1) was exchanged daily, and cells were detached with 0.25% trypsin (30-2101, ATCC) every two days. Split fractions were chosen so that cells were plated at approximately $1.2\times10^4$ cells/cm². Cells were used for differentiation experiments 4-6 days after thawing the cell vials.

Embryoid body formation. Cell suspensions obtained after trypsin detachment of undifferentiated ES cells were centrifuged at 300×g for 3 min, supernatant medium was removed, and cells were resuspended in ES cell differentiation medium (Table 1) that did not contain supplemental LIF. The concentration of cells with intact membranes was determined using trypan blue cell counts, and cells were diluted to a concentration of $2.5\times10^4$ membrane-intact cells/ml. 20-μl drops of this cell suspension were aliquoted onto the inside surface of the lids of 10×10 cm Petri dishes (351112, Becton Dickinson) using an 8-channel pipette. The lids were inverted and placed onto the bottoms of the dishes, which were filled with 15 ml of a pre-warmed (37° C.) solution containing 75% (v/v) Dulbecco's phosphate buffered saline (DPBS, 21-030-CM, Mediatech), 25% water, and 0.002% (w/v) gelatin.

Embryoid body transfer. After 2 days in hanging drops, the resulting embryoid bodies (EBs) were manually pipetted off of the Petri dish lid using wide-orifice pipette tips (3532, Molecular BioProducts, San Diego, Calif.) and placed into the wells of custom-made 24-well culture dish, which had the plastic bottom replaced with fibronectin-coated silicone rubber membrane. 30 EBs were placed into each well, and the medium was mixed by pipetting to distribute the EBs uniformly across the plate bottom.

Culture of attached embryoid bodies. The EBs attached and spread within one day of transfer to the silicone rubber membrane-based dish. The medium was removed from all of the wells 2 days after EB transfer and was replaced with 1 ml of fresh ES cell differentiation medium. On the following day, the medium was removed and replaced with 1 ml serum-free differentiation medium (Table 2). Medium continued to be exchanged daily with the serum-free differentiation medium until the end of the experiment.

Silicone rubber membrane-based dishes. Most of the bottom surface of the 8 central wells of 24-well tissue culture plates (353047, Becton Dickinson) was removed using a ⅜×3 inch fixed handle nutdriver (12, Cooper Hand Tools, Apex, N.C.) heated in a Bunsen burner to melt a hole in the plastic. A sterile scalpel was used to trim the edges of the holes. A very thin layer of silicone adhesive (59530, Henkel Loctite Corp., Rocky Hill, Conn.) was spread around each of the holes. A rectangular 8.5×4.5 cm piece of silicone rubber membrane (non-reinforced vulcanized gloss/gloss 0.005 inch, Specialty Manufacturing, Saginaw, Mich.), previously sterilized by autoclaving, was placed over the holes and manually pressed and stretched so that the silicone sheet was flat (no wrinkles) and sealed onto the plate bottom. After allowing the adhesive to cure for 24 hr, the plates were completely filled with a 70% ethanol solution for 1 hr and dried overnight under a germicidal UV lamp in a biological safety cabinet. One day prior to plating the cells, 1 ml of 2-14/ml fibronectin (F1141, Sigma-Aldrich) in DPBS was added to each well and incubated overnight at 37° C. Immediately before plating cells, the fibronectin solution was removed from all of the wells and replaced with 1 ml pre-warmed ES cell differentiation medium.

Gas phase $pO_2$ control. Cell culture vessels were placed inside sealed polystyrene chambers (MIC-101, Billups-Rothenburg, Del Mar, Calif.) that were housed inside a standard incubator (OWJ2720A, Queue Systems, Parkersburg, W. Va.) maintained at 37° C. The desired $pO_{2gas}$ was established and maintained using premixed gas containing 5% $CO_2$ and 20%, 5%, or 1% $O_2$ (certified medical gas from Airgas, Hingham, Mass.). The flow rate of gas to the chambers was 2 l/min for 15 min for an initial purge following closure of the chamber (after cell medium exchange) and 30 ml/min at all other times. Gas was bubbled through a sealed bottle of water (in the incubator), and an open dish of deionized water in each chamber provided additional humidification.

Example 3

Low Oxygen and Ascorbic Acid Act Synergistically to Promote Cardiomyocyte Generation. mES cells were differentiated for 10 days at 142, 36, and 7 mmHg $pO_2$ and with either 0 or 0.2 mM ascorbic acid. Cardiomyocyte generation was measured by counting fixed cells immunostained for sacromeric myosin heavy chain using the MF-20 with a flow cytometer. At all ascorbic acid conditions, low $pO_2$ increased cardiomyocyte generation. At all $pO_2$, ascorbic acid increased cardiomyocyte generation. However, when 0.2 mM ascorbic acid was combined with 36 mmHg $pO_2$, a larger increase in cardiomyocytes than with either method alone was observed. (FIGS. 10 and 11.). The presence of ascorbic acid and $pO_2$ gas together and separately also had a large effect on morphology (FIG. 12).

Example 4

This example provides a demonstration of the influence of low $pO_2$ culture on differentiation into mesoderm, endoderm, and ectoderm lineages. Cells were differentiated as specified in Example 1.

Real-Time Polymerase Chain Reaction (PCR). Total RNA was isolated using the RNeasy Kit (74104, Qiagen, Valencia, Calif.) and RNase-Free DNase Set (79254, Qiagen, Valencia, Calif.), cDNA was synthesized using High Capacity cDNA Reverse Transcription Kit (4368814, Applied Biosystems, Foster City, Calif.), and real-time PCR was performed on a Fast Real-Time PCR System (7900HT, Applied BioSystems), using Power SYBR Green PCR Master Mix (4367659, Applied BioSystems, Foster City, Calif.). 28S ribosomal RNA was used as an oxygen insensitive endogenous control (Zhong and Simons, 1999). Primer sequences used to assess gene expression are in Table 5. A standard calibration curve was constructed using undifferentiated mES cells.

Low Oxygen Influences Cardiac Gene Expression. mES cells were differentiated for 10 days at 142 and 7 mmHg $pO_2$ and relative gene expression of Tbx6, Nkx2.5, Mef2c, Gata4, and cardiac Troponin T (cTnT) measured with qPCR. Moderate levels of Tbx6 gene expression was observed between days 3 and 8 of differentiation at 142 mmHg $pO_2$. Tbx6 gene expression was not observed at 7 mmHg $pO_2$ until day 4-8, during which the overall magnitude of expression was many times greater than 142 mmHg. Gata4, Nkx2.5, and Mef2c gene expression was seen after 5 or 6 days of culture, during which expression was higher at 142 than 7 mmHg $pO_2$. However, at later time points, gene expression at 7 mmHg $pO_2$ was found to be much higher than 142 mmHg. Cardiac Troponin T (cTnT) gene expression was observed at day 5 for both 142 and 7 mmHg $pO_2$. Between days 5 and 10, cTnT expression was roughly constant at 142 mmHg but at 7 mmHg, increased to levels greater than 142 mmHg by day 10. (FIG. 13.) Brachyury T and cardiac Troponin T data can be seen on a semi log plot in FIG. 14. These data show low oxygen can be used to increase differentiation to cardiac cells and change the timing of cardiac gene expression. These data indicate that differentiation at 7 mmHg $pO_2$ results in temporally delayed expression of mesodermal and cardiac genes. By day 10, cardiac gene expression was higher at 7 mmHg than at 142 mmHg.

Low Oxygen Influences Definitive Endoderm Gene Expression. mES cells were differentiated for 6 days at 142, 36, and 7 mmHg $pO_2$ and relative gene expression of Sox17 and Foxa2 measured with qPCR. Sox17 expression peaked between days 4 and 5 for 142 and 36 mmHg, with more expression observed at 36 than 142 mmHg, and started decreasing at later times. After day 4, gene expression started increasing for Sox17 at 7 mmHg, never reaching a peak at the time period investigated. This data shows low oxygen can be used to increase differentiation to definitive endoderm and change the timing of definitive endoderm gene expression. (FIG. 15.)

Low Oxygen Influences Ectoderm Gene Expression. mES cells were differentiated for 10 days at 142, 36, and 7 mmHg $pO_2$ and relative gene expression of Nestin measured with qPCR. Nestin expression decreased with decreasing $pO_2$. (FIG. 16.) Microarray analysis also shows that differentiation at low oxygen partial pressure for 4 and 8 days results in the decreased expression of a large number of genes and increased expression of a smaller subset of genes. (Table 7.) These data show low oxygen can be used to limit differentiation of ES cells to ectoderm for as much as 10 days or more.

Example 5

Microarray Analysis of Genome-Wide Expression Displays Large Effects of Oxygen on Genes Involved in Development. A genome-wide microarray analysis was performed on mES cells differentiated at 142 or 7 mmHg $pO_2$ for 0, 4, and 8 days. Many genes known to be involved in development and differentiation displayed changes in expression at low $pO_2$ (Table 6). A total of 778 genes at day 4 and 1305 genes at day 8 were changed by a factor of 2 or more. Of these, 192 genes at day 4 and 351 at day 8 are associated with developmental processes.

Example 6

This Example outlines a typical culture for differentiation of ES cells into cardiomyocytes according to the invention.

Before differentiation, undifferentiated J1 mES cells were maintained with 1000 U/ml LIF in high glucose DMEM supplemented with 10% ES cell qualified fetal bovine serum (FBS). Using the hanging drop method, a cell suspension in DMEM with 10% FBS with 0.2 mM ascorbic acid was diluted to 25,000 cells/ml, and a 20-µl droplet of this suspension placed underneath the lid of a dish filled with PBS to maintain a high humidity and prevent droplet evaporation. EBs were formed using the hanging drop method rather than in suspension culture because hanging drops provide better control and uniformity in size and shape, which is important for achieving the most reproducible results. $pO_2$ gradients exist within these EBs, the centers are at a lower $pO_{2cell}$ than the outer edge, and uniform EBs enable consistent and reproducible $pO_{2cell}$ profiles. EBs were allowed 2 days to form and then transferred to a 24-well silicone rubber membrane-based plate. The culture surface was coated with 20 µg/ml fibronectin (Sigma) to promote adhesion. The cells were left to differentiate for another 3 days with the medium changed daily, followed by a change to a serum-free medium supplemented with insulin-transferrin-sodium selenite (ITS) with 0.2 mM ascorbic acid. The cells were then cultured for 16 more days.

The first 6 days of the differentiation was carried out at 36 mmHg $pO_{2gas}$. On day 6, the $pO_{2gas}$ was changed to 142 mmHg and maintained at that level for 15 additional days. Under these conditions, 57% of the resulting population was cardiomyocytes, and 304 cardiomyocytes were generated per each input ES cell as assessed by flow cytometry. These and other results are shown in FIG. 17.

Example 7

Brachyury T is a marker of the mesoderm, and its expression is increased at low oxygen. Transgenic ES with Brachyury T tagged with GFP have been developed. (See Fehling et al. Development 2003 130(17):4217-27.) Using the hanging drop method, a cell suspension of these cells in DMEM with 10% FBS with 0.2 mM ascorbic acid is diluted to 25,000 cells/ml, and a 20-μl droplet of this suspension is placed underneath the lid of a dish filled with PBS to maintain a high humidity and prevent droplet evaporation. EBs are formed using the hanging drop method rather than in suspension culture because hanging drops provide better control and uniformity in size and shape. $pO_2$ gradients exist within these EBs, the centers are at a lower $pO_{2cell}$ than the outer edge, and uniform EBs enable consistent and reproducible $pO_{2cell}$ profiles. For the entire experiment, cells are cultured at either standard or low $pO_{2gas}$. EBs are allowed 2 days to form and then transferred to a 24-well silicone rubber membrane-based plate. The culture surface is coated with 20 μg/ml fibronectin (Sigma) to promote adhesion. One, two, three, four, and five days after plating, cell samples are taken and fraction and number of Brachyury T+ cells counted using flow cytometry. Low oxygen produces a greater number and fraction of Brachyury T+ cells than standard $pO_{2gas}$ of 142 mmHg. Use of a FACS can separate these Brachyury T+, which can be replated and cultured to produce further differentiated progeny.

Example 8

Cells were cultured as in Example 1 at a $pO_{2gas}$ of 36 or 7 mmHg. FIG. 18 illustrates the generation of red blood cells, a mesoderm derivative, which occurred during differentiation of ES at 36 mmHg $pO_{2gas}$. Similar results were observed at a $pO_{2gas}$ of 7 mmHg. No red blood cells were observed when differentiation was carried out at a $pO_{2gas}$ of 142 mmHg. This result demonstrates the ability to generate cells of the hematopoietic lineage by use of culture under low oxygen conditions.

Example 9

Protocols have already been published for the differentiation of embryonic stem cells to insulin-producing beta-cells. (See for example Kroon et al. Nat Biotechnol 2008 26(4): 443-52.) These differentiation protocols can be performed at low oxygen (e.g., 36 mmHg) to increase the number of definitive endoderm cells produced. These cells are precursors to beta-cells. When pancreatic buds are forming (Fraker et al. Stem Cells 2007 25(12):3155-64), a switch from low (e.g., 36 mmHg) to high oxygen (e.g., 142 mmHg or greater) can be employed to further increase the yield of beta-cells.

Endoderm differentiation has been postulated to progress through 5 stages (definitive endoderm (stage 1), primitive gut tube (stage 2), posterior foregut (stage 3), pancreatic endoderm and endocrine precursor (stage 4), and hormone expressing endocrine cell (stage 5)). Stage 1 culture conditions are generally 1-2 days in the presence of activin and Wnt in the presence of RPMI and absence of serum followed by 1-2 days in the presence of activin, RPMI and 0.2% FBS. Stage 2 culture conditions are generally 2-4 days in the presence of FGF10 and CYC (KAAD-cyclopamine) in RPMI with 2% FBS. Stage 3 culture conditions are generally 2-4 days in the presence of all trans retinoic acid, CYC and FGF 10 in the presence of DMEM and 1% B27. Stage 4 culture conditions are generally exendin-4, DMEM and 1% B27 whether in the presence or absence of gamma-secretase inhibitor. Stage 5 culture conditions are generally 3 or more days in the presence of IGF1, HGF, CMRL with 1% B27 whether in the presence or absence of exendin-4. The invention contemplates low oxygen partial pressure at least at stage 1, and optionally a higher oxygen partial pressure at least at stage 5. Stages 1 and 2, stages 1, 2 and 3, or stages 1, 2, 3 and 4 may all be performed in low oxygen partial pressure with an increase in oxygen partial pressure at a stage thereafter.

Example 10

Low and high oxygen effects expression of genes associated with ES cell self-renewal and ES cell colony morphology. Real-time PCR analysis of ES cell markers Oct4, Sox2 and Nanog was performed on CCE cells cultured for 8 days with and without LIF in the culture medium. The results are shown in FIGS. 19 and 20. The data show that the relative gene expression of these transcription factors decreased as $pO_{2gas}$ decreased from 142 to 0 mmHg. The relative magnitude of the decline decreased in the order of Nanog>Oct4>Sox2. At all of the $pO_{2gas}$ conditions tested, the gene expression was lower in the absence than in the presence of LIF, and relative difference depended on $pO_{2gas}$. Subtle morphological changes in ES cell colonies were observed. (FIG. 21.) Even so, ES cells maintained the ability to express markers of all three germ layers. (FIG. 22.)

Example 11

This Example analyzes the use of silicone rubber as a membrane material for the precise control of the $pO_{2cell}$ for both cell monolayers and aggregates, using mES cells as the model system. The results show that a simple physical adsorption of fibronectin to silicone rubber is sufficient for robust cell adhesion and that these materials can be used to control $pO_2$ during the differentiation of mES cells into cardiomyocytes using an 11-day differentiation protocol, the last 9 days of which occur with the cells attached to silicone rubber membrane-based dishes.

Materials and Methods.
Silicone rubber membranes. Silicone rubber sheeting was purchased from Specialty Manufacturing (Saginaw, Mich.). The sheet was optically clear (gloss finish) and was 0.005 inch (127 mm) thick. Prior to use the membrane material was cut to the desired shape with scissors and sterilized by autoclaving for 30 min. at 121° C.
Silicone rubber membrane-based plate. The bottom surface of the 8 central wells of 24-well tissue culture plates (353047, Becton Dickinson) were removed using a ⅜×3 inch fixed handle nutdriver (12, Cooper Hand Tools, Apex, N.C.) heated in a Bunsen burner. A sterile scalpel was used to trim the edges of the holes so that they were flush with the rest of the plate bottom. A very thin layer of silicone adhesive (59530, Henkel Loctite Corp., Rocky Hill, Conn.) was spread on the base of the plate around each of the holes. A rectangular 8.5×4.5 cm piece of silicone rubber sheeting (non-reinforced vulcanized gloss/gloss 0.005 inch, Specialty Manufacturing, Saginaw, Mich.), previously sterilized by autoclaving, was placed over the holes, and manually pressed/stretched so that the silicone sheet was flat (no wrinkles) and sealed onto the plate bottom. After allowing the adhesive to set for 24 hr, the plates were completely filled with a 70% ethanol solution for 1 hr and dried overnight under a germicidal UV lamp in a biological safety cabinet).
Layer-by-layer film growth. Polyelectrolyte multilayers (PEMs) were prepared by adapting previously published methods (Ai et al. 2003). Solutions in Dulbecco's phosphate buffered saline (DPBS) (21-030-CM, Mediatech, Herndon, Va.) were prepared containing 3 mg/ml poly-sodium 4-styrene-sulfonate (PSS) (561967, Sigma-Aldrich, St. Louis, Mo.), 2 mg/ml poly-ethyleneimine (PEI) (P3143, Sigma-Aldrich), 0.5 mg/ml poly-D-lysine hydrobromide (PDL) (P1149, Sigma Aldrich), 1 mg/ml type A gelatin (G2500, Sigma-Aldrich), 1 mg/ml type B gelatin (G9391, Sigma-Aldrich), and 50 mg/ml fibronectin (F1141, Sigma-Aldrich). All coating steps were carried out at room temperature using 1 ml of solution per well of a 24 well silicone rubber membrane-based plate.

PSS solution (polyanion) was added to an untreated plate and incubated for 1 hr, followed by a 10 min wash with DPBS, a 1 hr incubation with PEI (polycation), and a 10 min wash with DPBS. Two additional incubations with both PSS and PEI (30 min each) with intervening washes (10 min) were done to build a (PSS-PEI)3 PEM. To this PEM an additional 3 layers each of type B gelatin (polyanion) and PDL (polycation) were formed, using 30 min incubations with the polyelectrolyte solution, and 10 min washes with DPBS. The final PEM structure was thus (PSS-PEI)3-(type B gelatin—PDL)$_3$. After assembly of the PEM an additional 20 hr incubation with type A gelatin, type B gelatin, or fibronectin was performed. The plates were then washed and incubated for 24 hr with DPBS prior to emptying the wells and adding cell culture medium and cells.

Physical adsorption of proteins. Untreated plates were incubated in either a 0.1% (w/v) solution of gelatin (G-2500, Sigma-Aldrich) in tissue culture water (25-055-CM, Mediatech, Herndon, Va.) or a 2 mg/ml solution of fibronectin (F1141, Sigma-Aldrich) in DPBS. Immediately before plating cells, the solution was removed and replaced with pre-warmed ES cell medium.

Nuclei enumeration. Supernatant medium from a well (1 ml) was mixed with an equal volume of a lysis solution containing 1% Triton X-100 (T9284, Sigma Aldrich) and 0.1 M citric acid (C1909, Sigma Aldrich) in DI water and stored at 4° C. for up to 1 day prior to analysis. Attached nuclei were counted by adding 0.5 ml of lysis solution to the well and incubating for 10 min. The solution was then removed, and 0.5 ml of DPBS was added to the well, pipetted up and down to remove any remaining cells, and saved for analysis.

Undifferentiated ES cell culture. Undifferentiated J1 ES cells were obtained from ATCC (SCRC 1010, Manassas, Va.) and cultured using the medium described in Table 1. Medium was exchanged daily, and cells were detached with 0.25% trypsin (30-2101, ATCC) every two days, and placed in a new dish at a density of $1.2\times10^4$ cell/cm2 in 4 ml of medium.

Cardiomyocyte differentiation. Cell suspensions obtained after trypsin-detachment of undifferentiated ES cells were centrifuged at 300×g for 3 min, supernatant medium was removed, and cells were resuspended in ES cell differentiation medium that did not contain supplemental LIF (Table 1). The membrane-intact cell concentration was determined using trypan blue cell counts, and cells were diluted to a concentration of 25,000 membrane intact cells/ml. 20-ml drops of this cell suspension were aliquotted onto the inside surface of the lids of 10×10 cm Petri dishes (351112, Becton Dickinson) using an 8-channel pipette. The lids were inverted and placed onto dish bottoms that were filled with 15 ml of a pre-warmed (37° C.) solution containing 75% DPBS (21-030-CM, Mediatech), 25% water, and 0.002% (w/v) gelatin.

After 2 days in hanging drops, the resulting embryoid bodies (EBs) were manually pipetted off of the Petri dish lid using wide-orifice pipette tips (3532, Molecular BioProducts, San Diego, Calif.) and placed into the wells of custom made fibronectin-coated silicone rubber membrane-based 24-well culture dishes. 30 EBs were placed into each well, and the medium was mixed by pipetting to distribute the EBs uniformly across the plate bottom.

The EBs attached and spread within one day of transfer to the silicone rubber membrane-based dish. The medium was removed from all of the wells 48 hours after EB transfer, and was replaced with 1 ml of fresh ES cell differentiation medium. The following day, the medium was removed and replaced with 1 ml serum-free differentiation medium described in Table 2. Medium continued to be exchanged daily with the serum-free differentiation medium until the end of the experiment.

Gas phase pO$_2$ control. Cell culture vessels were placed inside sealed polystyrene chambers (MIC-101, Billups-Rothenburg, Del Mar, Calif.) inside a standard incubator (OWJ2720A, Queue Systems, Parkersburg, W. Va.) maintained at 37° C. The desired pO$_{2gas}$ was established and maintained using premixed gas containing 5% CO$_2$ and 20%, 5%, 1%, or 0% O$_2$ (certified medical gas from Airgas, Hingham, Mass.). The flow rate of this gas to the chambers was set to 2 l/min for 15 minutes for an initial purge following closure of the chamber (after cell medium exchange), and was set at 30 ml/min all other times. Gas was bubbled through a sealed bottle of water (in the incubator) and an open dish of deionized water in each chamber provided additional humidification.

Cell isolation for nuclei counts and flow cytometry. The medium was removed at the end of the experiment from the wells of the 24-well silicone rubber membrane-based culture dish, the cells were washed with DPBS, and 200 ml of trypsin solution was added to each well. After a 5 min incubation at 37° C., 800 ml of ES cell differentiation medium was added to each well. The contents of the well were vigorously pipetted up and down using a 1 ml pipette to dislodge and disperse the cells, and were then transferred to a 1 ml tube. The contents were allowed to settle for 2 min, then the bottom 50 ml that contained any large clumps of cells and extra-cellular matrix were removed and discarded (or saved for later analysis). The cell sample was then mixed briefly with a vortex mixer and a 50 ml aliquot was removed, added to 450 ml of lysis solution containing 1% Triton X-100 (T9284, Sigma Aldrich) and 0.1 M citric acid (C 1909, Sigma Aldrich) in DI water, and saved for later analysis. The remaining 900 ml of cell sample was centrifuged at 300×g for 3 min and the supernatant medium was discarded. Cells were resuspended in 750 ml DPBS, 250 ml of 4% (w/v) paraformaldehyde (Alfa Aesar, Ward Hill, Mass.) in DPBS was added, and each sample was incubated for 20 min at room temperature. The samples were then centrifuged at 300×g, the supernatant removed, and 1 ml of DPBS was added. Nuclei and fixed cell samples were stored at 4° C. prior to analysis.

Flow cytometry. Samples with 3×10$^5$ fixed cells were removed the fixed cell sample tubes and added to an equal volume of 1% (w/v) saponin (S-4521, Sigma-Aldrich) and incubated for 10 min to allow for cell permeabilization. Subsequently, the cells were washed and resuspended in 50 µl of 2% (v/v) FBS in PBS. Samples were incubated in the 2% FBS solution for 30 min, and then 5 µl of anti-sarcomeric myosin heavy chain antibody (MF-20, MF-20 supernatant, Developmental Studies Hybridoma Bank, Iowa City, Iowa) was added. Samples were incubated for 1 hr, then 0.5 ml of 2% FBS solution was added to each tube and the samples were centrifuged. The supernatant was discarded and the cells were resuspended in 50 ml of goat anti-mouse PE-conjugated secondary antibody (115-116-146, Jackson ImmunoResearch, West Grove, Pa.) diluted 1:250 in 2% FBS. The samples were incubated 30 min in the dark, washed twice with 0.5 ml of PBS, and fluorescence intensity data were acquired using a flow cytometer (Guava Technologies) using the Express software module. All steps were performed at room temperature.

Results.

Cell attachment to silicone rubber. Undifferentiated mES cells did not attach to native silicone rubber or silicone rubber that was pretreated with gelatin prior to cell addition (FIG. 23). When mES cells were placed into such wells, they formed freely floating embryoid bodies (EBs) after 24 hr in culture. Exposure of the membrane to 2 mg/ml fibronectin in DPBS for a day prior to addition of the cells was sufficient for attachment of 99% of the cells. However, there was a small but significant decrease in the total cell number on the silicone rubber treated with fibronectin relative to the tissue culture plastic. The cause for this is not known. A 2 mg/ml fibronectin solution effectively coated the silicone rubber and promoted cell attachment if it was prepared in DPBS (as described above) or a serum-free ITS medium, but cells would not attach to the silicone rubber surface when the 2 mg/ml fibronectin solution was made in DMEM with 10% FBS (data not shown). This was presumably a result of competitive adsorption of serum proteins onto the silicone surface, which limited fibronectin adsorption.

Tissue culture polystyrene did not require pretreatment with any protein layer prior to cell addition. In all polystyrene conditions tested, greater than 99% of the cells were attached after a day in culture. Pretreatment of polystyrene with fibronectin or to a lesser extent gelatin, caused the cells to have a more widely spread morphology but did not affect cell proliferation (FIG. 23).

Deposition of a (PSS-PEI)4-(PDL-gelatin)3 PEM onto silicone rubber prior to cell addition could be used to promote cell adhesion. Comparison of Table 8 with FIG. 23 shows that cells adhered better to silicone rubber with a PEM than they did to unmodified silicone. However, attachment to these materials still was not as robust as it was to any of the tissue culture polystyrene surfaces tested. Also, the PEM-gelatin structures did not support attachment as well as the single layer of fibronectin adsorbed onto silicone rubber. Other modifications of the PEM method examining the use of fewer layers were also tested with results comparable to those shown in Table 8 (data not shown).

Comparison of silicone rubber and polystyrene surfaces. A comparison of the results of using polystyrene dishes and silicone rubber membrane-based dishes for differentiation of ES cells into cardiomyocytes is shown in FIG. 24. This shows the fraction of cells that were positively immunostained with MF-20, a marker of cardiomyocytes, total cell number, and total cardiomyocyte number after 11 days of differentiation for experiments carried out on silicone rubber membranes and polystyrene dishes. There were significantly fewer cells in the polystyrene relative to the silicone rubber membrane-based plates, consistent with the modeling that indicated extreme oxygen starvation under such conditions. Use of an oxygen sensitive dye on the bottom of polystyrene and silicone rubber membrane-based wells verified that significant oxygen depletion was present in the polystyrene dishes, but not in wells with a silicone rubber membrane bottom (data not shown).

A higher fraction of cells were cardiomyocytes on the polystyrene dish relative to the silicone rubber membrane at a $pO_{2gas}$ of 36 and 142 mmHg, while at a $pO_{2gas}$ of 7 mmHg there were a lower fraction of cardiomyocytes on polystyrene dishes relative to silicone rubber membranes. The cells also adopted a much more widely spread morphology on the polystyrene dishes compared to the silicone rubber membranes (not shown). No spontaneous contraction was observed in any $pO_{2gas}$ condition on the polystyrene dishes, whereas on silicone rubber membranes an excellent correlation was found between immunostaining for MF-20 and the area covered with spontaneously contracting cells (data not shown). Similar results on polystyrene were seen in a subsequent experiment, but there is no apparent explanation for the lack of spontaneously beating cells on these dishes.

Discussion.

These experiments were aimed at determining whether silicone rubber membrane based dishes were an improvement on existing polystyrene and FEP-teflon membrane based dishes for the precise control of the $pO_{2cell}$ during static culture with cell monolayers and aggregates. Surface modifications that could be used to promote cell attachment to the silicone rubber surface were also studied. These surface modified dishes were then used for the study of the effect that oxygen has on the differentiation into cardiomyocytes. Our theoretical simulations show that membrane based culture dishes improve the oxygenation of cells in static culture and are consistent with the available literature (Avgoustiniatos ES. 2002. Oxygen diffusion limitations in pancreatic islet culture and immunoisolation. Cambridge: MIT; Jensen et al. 1976 J Theor Biol 56(2):443-58.; Wolff et al. 1993 Am J Physiol 265(5 Pt 1):C1266-70.). Previously published data are not available to compare FEP-teflon membranes to silicone rubber, nor are there to our knowledge published experiments showing that membrane-based culture dishes can be used to reduce the time for equilibration of the $pO_{2cell}$ after a change in $pO_{2gas}$.

The differences between silicone rubber and FEP-teflon are of practical significance because the only widely commercially available membrane-based dish is constructed of FEP-teflon. Our results show that this dish is a significant improvement over polystyrene, but it is not nearly as effective as silicone rubber for the control of $pO_{2cell}$. According to our theoretical calculations, FEP-teflon membranes are expected to have a $DpO_2$ that is about 15 mmHg at high cell densities, which is adequate for culture of cells at a $pO_{2gas}$ of 142 mmHg. A $DpO_2$ of 15 mmHg is relatively large if it occurs during studies at physiological $pO_2$ conditions in the range of 0-40 mmHg. Such experiments require a silicone rubber membrane or convective mixing for precise $pO_{2cell}$ control.

Precise $pO_{2cell}$ control is not possible during culture of cell aggregates. Membrane-based dishes improve oxygenation of aggregates in culture relative to polystyrene dishes, however there are still oxygen gradients within the tissue that can be significant, as has been previously predicted (Avgoustiniatos ES. 2002. Oxygen diffusion limitations in pancreatic islet culture and immunoisolation. Cambridge: MIT). These gradients can result in tissue being oxygen starved, especially at reduced $pO_{2gas}$ conditions. Quantitative studies of $pO_2$ effects on cell aggregates must therefore consider aggregate sizes to estimate the range of $pO_{2cell}$ values that are present. The transfer of a cell culture protocol from polystyrene dishes to FEP-teflon or silicone rubber will introduce changes in the cell-substrate interactions in addition to changes in cell oxygenation. A method described previously using a PEM to functionalize the silicone rubber was used to promote cell attachment (Ai et al. 2003. Journal of Neuroscience Methods 128(1-2):1-8). Although the PEM improved cell attachment compared to native silicone rubber, the best attachment was found using simple physical adsorption of fibronectin onto the silicone rubber. The use of physical adsorption was also much easier to accomplish and required only an incubation of a single solution, whereas forming a full PEM required 14 different incubation steps (with a wash between each step). It is not clear why others found physical adsorption of fibronectin to silicone rubber to be inefficient (Cunningham et al. 2002. Biotechniques 32(4):876), but it may be partially due to the solutions that were used. We found that incubation of the silicone rubber with fibronectin solution in PBS promoted very good cell adhesion, whereas if the fibronectin solution contained 10% serum the subsequent cell adhesion was poor.

Fibronectin-coated silicone rubber membrane-based dishes could be used to study the effect that changing $pO_{2cell}$ has on the differentiation of ES cells into cardiomyocytes. These experiments were performed by forming cellular aggregates in hanging drops for 2 days, then transferring them to an adherent dish for 9 additional days. On silicone rubber membrane-based dishes, we observed the maximal cardiomyocyte fraction occurred at the lowest $pO_{2gas}$ condition (7 mmHg) with decreasing fractions at 36 and 142 mmHg, and the most total cardiomyocytes were obtained at a $pO_{2gas}$ of 36 mmHg. Use of a polystyrene dish resulted in significantly fewer cells presumably due to oxygen limitations, and showed that the maximum cardiomyocyte fraction was obtained at a $pO_{2gas}$ of 36 mmHg. There was also no increase in the total number of cardiomyocytes in $pO_{2gas}$ conditions less than 142 mmHg using a polystyrene dish. This experimental system appears to be one in which the use of a gas impermeable dish to study oxygen effects gives misleading results due to differences between the $pO_{2gas}$ and $pO_{2cell}$.

This work shows that silicone rubber membrane-based dishes offer substantial improvements in tissue oxygenation over polystyrene and FEP-teflon membrane-based culture vessels, and that physical adsorption of fibronectin to silicone rubber surfaces can be used to promote prolonged ES cell attachment. These findings strongly suggest that membrane-based dishes should be used whenever possible if oxygen is a variable of interest.

Example 12

This Example analyzes the use of silicone rubber as a membrane material for the precise control of the $pO_{2cell}$ for cell monolayers, using mES cells as the model system. The results show that use of polystyrene or PEF-teflon results in large drops between $pO_{2gas}$ and $pO_{2cell}$, and this drop is minimized when silicone rubber is used. Additionally, the time to reach steady state is a lot quicker with silicone rubber than the other culture surfaces. The differences between silicone rubber and FEP-teflon are of practical significance because the only widely commercially available membrane-based dish is constructed of FEP-teflon. Our results show that this dish is a significant improvement over polystyrene, but it is not nearly as effective as silicone rubber for the control of $pO_{2cell}$. FEP-teflon membranes have a $DpO_2$ that is about 15 mmHg at high cell densities, which is adequate for culture of cells at a $pO_{2gas}$ of 142 mmHg. A $DpO_2$ of 15 mmHg is relatively large if it occurs during studies at physiological $pO_2$ conditions in the range of 0-40 mmHg. Such experiments require a silicone rubber membrane or convective mixing for precise $pO_{2cell}$ control.

Methods

The $DpO_2$ was estimated by equating the rate of one-dimensional diffusion of oxygen through the stagnant medium and the culture dish bottom to the rate of oxygen consumption by cells according to the following equation $$\Delta_p O_2 = \rho V_{max} \left[ \frac{D_m \alpha_m}{L_m} + \frac{D_b \alpha_b}{L_b} \right]^{-1} \quad (1)$$

where Vmax is the experimentally measured OCR/cell, r is the cell surface density, D and a are the diffusivity and solubility of oxygen, respectively, L is the depth, and subscripts m and b refer to the medium and dish bottom, respectively. For our calculations we used 2.97, 2.21, 0.028, and 0.011×10-5 cm2/sec as the values for the diffusivity of oxygen in culture medium, silicone rubber, FEP-teflon, and polystyrene, respectively, and 1.19, 11.9, 5.06, and 8.6×10-9 mol/cm³ mmHg as values for the solubility of oxygen in culture medium, silicone rubber, FEP-teflon, and polystyrene, respectively.

The transient $pO_2$ at the culture dish-medium interface was estimated numerically using the finite element package Comsol Multiphysics. Simulations were done in the absence of cells and results are reported as fractional approach to the final steady-state $pO_2$ versus the time after a step change in $pO_{2gas}$.

Results

Figure 25A:
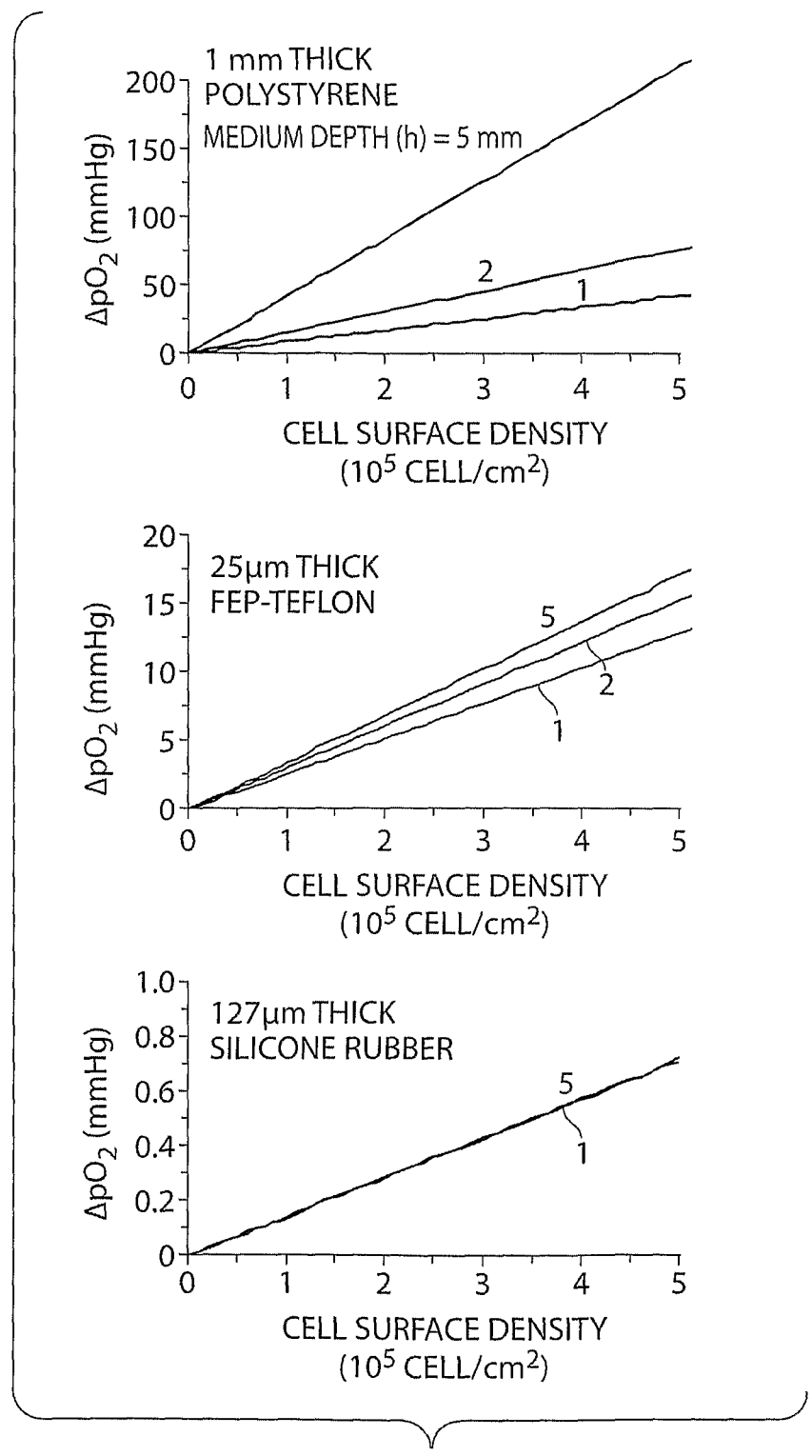

The difference between $pO_{2gas}$ and $pO_{2cell}$ ($DpO_2$) determined for monolayers of cells cultured on polystyrene, FEP-teflon, and silicone rubber using steady state simulations is shown in FIG. 25A. The $DpO_2$ is highly dependent on the cell surface density (OCR density) and the medium height during culture on a polystyrene dish. For high cell densities and medium depths the magnitude of $DpO_2$ can become quite large and can exceed 142 mmHg, which is the usual $pO_{2gas}$ used for culture, causing cells to become oxygen starved. The overall magnitude of the $DpO_2$ and its dependence on the medium height and cell surface density is significantly reduced using an FEP-teflon membrane, and reduced to almost 0 using a silicone rubber membrane-based culture dish. For conditions commonly encountered for undifferentiated ES cell culture, 1-2×105 cell/cm2 and a medium height of 2 mm, the absolute $DpO_2$ is 15-35, 3-6, and 0.1-0.3 mmHg on polystyrene, FEP-teflon, and silicone rubber, respectively. Higher cell densities can be encountered during differentiation, and the $DpO_2$ will be greater in such circumstances.

Figure 25B:
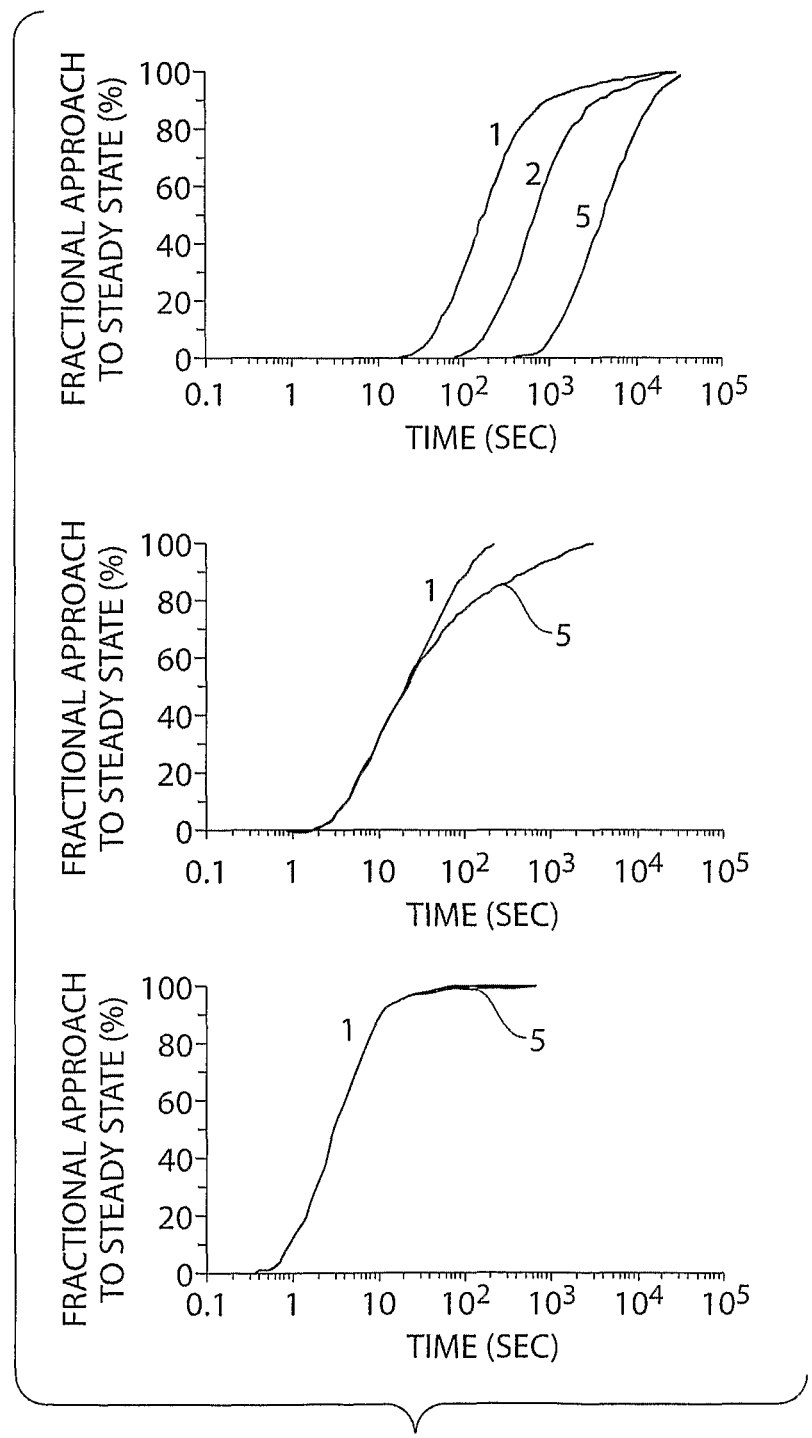

The time for the $pO_{2cell}$ to equilibrate after a step change in $pO_{2gas}$ was determined for polystyrene, FEP-teflon, and silicone rubber dishes using finite element simulations. (FIG. 25B.). The equilibration time was quite long on a polystyrene dish and was highly dependent on the medium volume. Approximately 1000, 4000, and 20000 sec were required to reach 90% of the steady state $pO_{2cell}$ at medium depths of 1, 2, and 5 mm, respectively, in a polystyrene dish. The time to reach 90% of the equilibrium $pO_{2cell}$ was about 100 and 500 sec at depths of 1 and 5 mm, respectively, on an FEP-teflon membrane, and 10 seconds in a silicone rubber dish with any medium height.

Example 13

Cardiomyocytes can be derived from human ES (hES) cells. Cardiomyocyte generation can be done in monolayer culture by a 24-hour induction with 100 ng/mL activin A followed by 10 ng/mL BMP4 for 4 days. Spontaneously beating cardiomyocytes can be observed 12 days after activin A induction. (Gold, J. et al. Efficient serum-free generation of cardiomyocytes from human embryonic stem cells in the absence of embryoid bodies (abstract). Circulation 112 (17, Suppl.S), U62-U62 (2005)). Constant low $pO_{2gas}$ (36 or 7 mmHg) in combination with this protocol can be used to further increase the yield of cardiomyocytes. Low $pO_{2gas}$ (36 or 7 mmHg) for the first 1 to 12 days of differentiation with a switch to normal (142 mmHg) $pO_{2gas}$ can be used to even further increase the yield of cardiomyocytes when combined with this protocol.

Example 14

Low $pO_{2gas}$ (e.g., 36 or 7 mmHg) culture can be combined with multiple factors to increase cardiomyocyte generation from mouse ES cells. ES cells can be differentiated as outlined in Example 1 with 0.2 mM ascorbic acid and 100 ng/mL activin A. Combining these multiple factors with low oxygen culture results in even more cardiomyocytes than with the factors at normal oxygen.

Example 15

Low $pO_{2gas}$ (e.g., 36 or 7 mmHg) culture can be combined with multiple factors to increase cardiomyocyte generation from mouse ES cells. ES cells can be differentiated as outlined in Example 1 with 0.2 mM ascorbic acid and 0.1 µM 5-azacytidine. (Yoon, et al. Differentiation, 2006. 74(4): p. 149-59.) Combining these multiple factors with low oxygen culture results in even more cardiomyocytes than with the factors at normal oxygen.

Example 16

The change in fraction of cardiomyocytes, total cell number, and total cardiomyocyte number as a function of oxygen are shown versus time during differentiation. (FIG. 26.) Cardiomyocytes first appeared at day 6 in these experiments, and the time of appearance was slightly delayed by culture at 7 mmHg. A similar delay at very low oxygen was reproducibly observed in other experiments. The cell number increased between 0 and 4 days during EB culture, remained flat or decreased for the following 4 days after transfer of the EBs to serum free ITS medium, then subsequently increased further. The total cardiomyocyte number increased between days 4 and 14, with a significantly increased number of cardiomyocytes present at 7 relative to 142 mmHg. Other experiments showed comparable trends, with the maximal cardiomyocyte fraction occurring at day 8-14, then remaining steady or decreasing slightly (data not shown). Likewise, the maximum cardiomyocyte number occurred at about the same time that the maximal cardiomyocyte fraction was observed. Later experiments therefore were focused primarily on the first 12 days of differentiation.

Differentiation Method. EBs were made with 7×105 cells placed into 60 mm hydrophobic FEP-teflon membrane-based dish (96077305, Greiner Bio-One, Monroe, N.C.) containing 2 ml of medium. A partial medium exchange was performed after 2 and 3 days by aspirating 2 ml of medium from the top of the dish and replacing it with fresh differentiation medium. After 4 days in culture, the cells and cell aggregates were removed from the dish, and any adherent EBs were removed by pipetting the medium up and down. The EBs were placed a tube, allowed to settle, all but 1 ml was removed, and 3 ml fresh differentiation medium was added. The EBS were then aliquotted equally to 4 wells of a 12-well silicone rubber membrane-based plate, that had been preincubated overnight with an ITS medium containing 5 µg/ml fibronectin (F 1141, Sigma-Aldrich). Medium was exchanged with fresh ITS medium with fibronectin the day after plating the cells, and every two days thereafter.

Example 17

A systematic variation in the number of cells used for the formation of EBs and the time in which the EBs were cultured in hanging drops before being transferred to adherent dishes was performed using the same methods as Example 1 except as noted in the Figures. The time of transfer from serum containing medium to serum-free ITS medium was varied in some of the experiments (panel A), and kept constant in others (panel B). For all of the protocol variations that were studied, there was always a higher surface coverage of beating cells at $pO_{2gas}$ of 7 or 36 relative to 142 mmHg.

For all $pO_{2gas}$, the highest coverage of beating cells was present when 500 cells were used for EB formation, EBs were transferred to adherent dishes on day 2, and serum was removed on day 5. The high surface coverage of spontaneously contracting cells was not due to an increase in total cell number, but was instead due to an increase in the fraction of cardiomyocytes (data not shown). Further increases in cell number in the initial EBs, or shortening the time in EBs to 1 day showed no further increase in the surface coverage of beating cells (data not shown), relative to the conditions in FIG. 27.

The transfer to a serum-free medium was required for the maximal differentiation of mES cells into cardiomyocytes. Culture in DMEM with 10% serum throughout the experiment did not affect the total cell number, but resulted in a reduced fraction of cells that were cardiomyocytes (and hence fewer total cardiomyocytes) in all $pO_{2gas}$ conditions relative to cultures that were transferred to serum free ITS medium on day 5. The change to ITS medium did not affect the fraction or total number of cardiomyocytes of the respective $pO_{2gas}$ conditions relative to one another. In both cases, the highest fraction and total number of cardiomyocytes were obtained at $pO_{2gas}$ conditions of 7 and 36 mmHg, respectively. Forming of EBs in simple suspension culture is much easier than using hanging drops, and is therefore generally preferred. However, premature (early) attachment of EBs clearly affects ES cells differentiation into cardiomyocytes. The degree of attachment and time at which it occurred was affected by $pO_{2gas}$ during suspension culture, so this secondary oxygen effect could certainly be present if EB attachment is not well controlled.

TABLE 1

Formulation for undifferentiated ES cell maintenance medium and ES cell differentiation medium.

| Component | Manufacturer and Catalogue # | Volume per Liter (ml) | Notes |
|---|---|---|---|
| Dulbecco's modified Eagles medium (DMEM) | ATCC SCRR 2010 | 868 | ES cell qualified |
| Foetal bovine serum (FBS) | ATCC SCRR 30-2020 | 100 | ES cell qualified |
| L-alanyl-L-glutamine | ATCC SCRR 30-2115 | 10 | 200 mM stock solution |
| MEM non-essential amino acid solution | ATCC 30-2116 | 10 | |
| 2-mercapto-ethanol stock solution | Sigma Aldrich M7522 | 10 | 10 mM stock solution prepared by adding 28 µl of M7522 to 40 ml DMEM and sterile filtering |

TABLE 1-continued

Formulation for undifferentiated ES cell maintenance medium and ES cell differentiation medium.

| Component | Manufacturer and Catalogue # | Volume per Liter (ml) | Notes |
|---|---|---|---|
| Leukaemia inhibitory[1] factor (LIF) | Chemicon ESG 1106 | 1 | $10^6$ unit/ml stock solution (final concentration = 1000 U/ml) |
| L-ascorbic acid[2] stock solution | Sigma Aldrich A4034 | 1 | 200 mM stock solution prepared by dissolving 396 mg of A4034 in 10 ml DPBS and sterile filtering |

[1] Leukaemia inhibitory factor was added only to the undifferentiated ES cell maintenance medium

[2] Ascorbic acid was added only to the ES cell differentiation medium. Some experiments described in the supplemental material were also done in medium without ascorbic acid.

TABLE 2

Formulation for serum-free ITS medium.

| Component | Manufacturer and Catalogue # | Volume per Liter (ml) | Notes |
|---|---|---|---|
| Dulbecco's modified Eagles medium (DMEM) | Mediatech 90-113-PB | 485 | 4.08 g of 90-113-PB were dissolved in 485 ml WFI (Mediatech 25-055-CM) and sterile filtered |
| sodium bicarbonate | Mediatech 25-035-CI | 10 | 7.5% (w/v) solution |
| F12 nutrient mixture | Invitrogen 31765-035 | 496 | |
| 25M glucose solution | Sigma Aldrich G8769 | 1.6 | Final glucose concentration of medium is 9 mM |
| human insulin solution | Sigma Aldrich I9278 | 0.5 | 10 mg/ml solution |
| holo transferrin solution | Sigma Aldrich T1283 | 5 | 10 mg/ml stock solution prepared by dissolving 100 mg in 10 ml DPBS and sterile filtering |
| sodium selenite solution | Sigma Aldrich S9133 | 0.26 | 0.12 mM solution prepared by adding 50 ml DPBS to S9133 |
| L-ascorbic acid stock solution | Sigma Aldrich A4034 | 1 | 200 mM stock solution prepared by dissolving 396 mg of A4034 in 10 ml DPBS and sterile filtering |

TABLE 3

Properties of clumps from 5-μm sections of day 10 and 11 tissue.

| | $pO_{2gas}$ (mmHg) | | |
|---|---|---|---|
| | 7 | 36 | 142 |
| Fraction of tissue in clumps (%) | 53 ± 6 | 75 ± 9 | 90 ± 7 |
| Number of Clumps Analyzed | 21 | 19 | 12 |
| Clump height (μm) mean ± s.d. | 120 ± 60 | 190 ± 100 | 280 ± 150 |
| range | 45-230 | 80-430 | 80-500 |
| Clump width (μm) mean ± s.d. | 450 ± 290 | 610 ± 320 | 590 ± 370 |
| range | 80-1000 | 150-1100 | 100-1300 |

TABLE 4

Fraction of MF-20 positive cells with alternate differentiation protocol.

| | Without Ascorbic Acid | | | With 0.2 mM Ascorbic Acid | | |
|---|---|---|---|---|---|---|
| Cell Line | 142 | 36 | 7 | 142 | 36 | 7 |
| J1 | 0.5 ± 0.2 | — | 5 ± 2 | — | — | — |
| R1 | 0.8 ± 0.2 | 4 ± 2 | 3.3 ± 0.9 | — | — | — |
| J1 | 0.4 ± 0.2 | 3.5 ± 1.9 | 6 ± 3 | 0 | — | 19 |
| J1 | 1.0 ± 1.0 | — | 6.1 ± 0.5 | — | — | — |
| J1 | 0.5 | 7 | 2 | 0.5 | 18 | 9 |
| R1 | — | 12 | 2 | — | 22 | 4 |
| J1 | 4.6 | 12 | 2 | 13 | 25 | 8 |
| J1 | 1 | 9 | 1 | 4 | 16 | 3 |
| J1 | — | — | — | 13 | 16 | 24 |

Cells were differentiated in hanging drop EBs in DMEM with 10% FBS for 4 days, then transferred to fibronectin-coated silicone rubber membrane based dishes with serum free ITS medium for the remaining 7 days. Results shown are for independent experiments started with different batches of cells on different days. Data reported as mean (±s.d.) for triplicate samples from the same experiment.

TABLE 5

Primer sequences used for real-time PCR.

| Target Gene | Direction | Sequence |
|---|---|---|
| 28S rRNA | Forward | GAATCCGCTAAGGAGTGTGTAACA (SEQ ID NO: 1) |
| | Reverse | CTCCAGCGCCATCCATTT (SEQ ID NO: 2) |
| Oct4 | Forward | CACGAGTGGAAAGCAACTCAGA (SEQ ID NO: 3) |
| | Reverse | TCTCCAACTTCACGGCATTG (SEQ ID NO: 4) |
| Nanog | Forward | CCTGATTCTTCTACCAGTCCCA (SEQ ID NO: 5) |
| | Reverse | GGCCTGAGAGAACACAGTCC (SEQ ID NO: 6) |
| Sox2 | Forward | GACAGCTACGCGCACATGA (SEQ ID NO: 7) |
| | Reverse | GGTGCATCGGTTGCATCTG (SEQ ID NO: 8) |
| Nkx2.5 | Forward | CAGTGGAGCTGGACAAAGCC (SEQ ID NO: 9) |
| | Reverse | TAGCGACGGTTCTGGAACCA (SEQ ID NO: 10) |
| Sox17 | Forward | GCTGGCGGGTCTGAAGTG (SEQ ID NO: 11) |
| | Reverse | TAACTTCTGCTGACCATTCTCTTGA (SEQ ID NO: 12) |
| Nestin | Forward | GCTGGAACAGAGATTGGAAGG (SEQ ID NO: 13) |
| | Reverse | CCAGGATCTGAGCGATCTGAC (SEQ ID NO: 14) |

Sequences reported 5' to 3'.

TABLE 6

Genes affected by low oxygen.

| General Gene Categories | | Day 4 | | Day 8 |
|---|---|---|---|---|
| All Genes Effected | ↑ | 376 (9) | ↑ | 769 (134) |
|  | ↓ | 402 (14) | ↓ | 536 (34) |
| All Developmental Genes | ↑ | 46 (3) | ↑ | 152 (29) |
|  | ↓ | 146 (5) | ↓ | 199 (24) |
| All Organs | ↑ | 43 | ↑ | 85 (18) |
|  | ↓ | 99 (3) | ↓ | 112 (17) |
| Specific Developmental Genes | | | | |
| Lung | ↑ | 1 | ↑ | 3 |
|  | ↓ | 3 (1) | ↓ | 16 (5) |
| Kidney | ↑ | — | ↑ | 3 |
|  | ↓ | 11 | ↓ | 13 (4) |
| Immune System | ↑ | 17 (15) | ↑ | 39 (15) |
|  | ↓ | 2 (2) | ↓ | 9 (2) |
| Heart | ↑ | 3 | ↑ | 15 |
|  | ↓ | 25 | ↓ | 24 (4) |
| Nervous System | ↑ | 27 | ↑ | 25 (1) |
|  | ↓ | 44 (1) | ↓ | 76 (11) |
| Blood Vessel | ↑ | 6 | ↑ | 23 (1) |
|  | ↓ | 27 | ↓ | 16 (2) |

Numbers indicate number of genes affected by low pO$_2$ by a factor of ≥2 (factor of 5 in parenthesis).

TABLE 7

Ectoderm genes affected by low oxygen.

| | Gene Symbol | Gene Name |
|---|---|---|
| Day 4↓ | Nab2 | Ngfi-A binding protein 2 |
| | Foxq1 | forkhead box Q1 |
| | Tgfb2 | transforming growth factor, beta 2 |
| | Sox9 | SRY-box containing gene 9 |
| | Ntf3 | neurotrophin 3 |
| | Grhl3 | grainyhead-like 3 (*Drosophila*) |
| | Sprr2a | small proline-rich protein 2A |
| | Runx3 | runt related transcription factor 3 |
| | Sprr1a | small proline-rich protein 1A |
| Day 4↑ | Fst | follistatin |
| | Krtdap | keratinocyte differentiation associated protein |
| Day 8↓ | Hes1 | hairy and enhancer of split 1 (*Drosophila*) |
| | Trp63 | transformation related protein 63 |
| | Sox9 | SRY-box containing gene 9 |
| | Shh | sonic hedgehog |
| | Foxq1 | forkhead box Q1 |
| | Sprr2a | small proline-rich protein 2A |
| | Ntf3 | neurotrophin 3 |
| | Ppl | periplakin |
| Day 8↑ | Nf2 | neurofibromatosis 2 |

TABLE 8

Cell attachment to polystyrene and silicone rubber functionalized with a PEM.

| | Cell Number (×10$^4$ cell) | | | |
|---|---|---|---|---|
| Surface | Total | Attached | Suspension | % Attached |
| TC Polystyrene unmodified | 59 ± 4 | 58 ± 4 | 1.0 ± 0.3 | 98 |
| TC Polystyrene Gelatin A | 56 ± 3 | 56 ± 3 | 0.52 ± 0.04 | 99 |
| TC Polystyrene Gelatin B | 58 ± 1 | 57 ± 1 | 0.69 ± 0.07 | 99 |
| Silicone Rubber PEM - Gelatin A | 52 ± 8 | 50 ± 8 | 1.9 ± 0.2 | 96 |
| Silicone Rubber PEM - Gelatin B | 47 ± 3 | 45 ± 3 | 2.0 ± 0.1 | 96 |
| Silicone Rubber PEM - Fibronectin | 38 ± 3 | 36 ± 3 | 1.2 ± 0.3 | 97 |

26×10$^4$ viable cells were placed into each well of a 24-well plate and cultured for 18 hr prior to assessing cell attachment. Results are from a single experiment and are reported as the mean±SD for triplicate wells for each condition.

Equivalents

It should be understood that the preceding is merely a detailed description of certain embodiments. It therefore should be apparent to those of ordinary skill in the art that various modifications and equivalents can be made without departing from the spirit and scope of the invention, and with no more than routine experimentation.

All references, patents and patent applications that are recited in this application are incorporated by reference herein in their entirety.

What is claimed is:

1. A method for enhancing mesoderm differentiation from pluripotent stem cells comprising
culturing pluripotent stem cells at a cell surface oxygen partial pressure that is less than 142 mmHg throughout a time period sufficient to induce mesoderm specific gene expression, wherein the cell surface oxygen partial pressure is about gas phase oxygen partial pressure,
wherein the pluripotent stem cells are mouse or human pluripotent stem cells,
wherein the pluripotent stem cells are cultured on a silicone rubber membrane.

2. The method of claim 1, wherein the pluripotent stem cells are embryonic stem (ES) cells.

3. The method of claim 1, wherein the pluripotent stem cells are cultured for at least 3 days.

4. The method of claim 1, wherein the pluripotent stem cells are cultured for at least 6 days.

5. The method of claim 1, wherein the pluripotent stem cells are cultured for 3-6 days.

6. The method of claim 1, wherein the pluripotent stem cells are cultured for 5-15 days.

7. The method of claim 1, wherein the cell surface oxygen partial pressure is less than 50 mmHg.

8. The method of claim 1, wherein the cell surface oxygen partial pressure is less than 40 mmHg.

9. The method of claim 1, wherein the cell surface oxygen partial pressure is less than 10 mmHg.

10. The method of claim 1, further comprising a second culture step at a second cell surface oxygen partial pressure that is greater than the first cell surface oxygen partial pressure.

11. The method of claim 10, wherein the second culture step is performed at a second cell surface oxygen partial pressure of 142 mmHg.

12. The method of claim 10, wherein the second culture step is performed for at least 10 days.

13. A method for producing or enriching cardiomyocytes comprising
performing a first culture step comprising culturing ES cells at a first cell surface oxygen partial pressure that is about 36 mmHg for a first time period of 6 days,
performing a second culture step comprising culturing the ES cells at a second cell surface oxygen partial pressure that is 142 mmHg for a second time period that is about 15 days,
wherein cell surface oxygen partial pressure is about gas phase partial pressure in the first and second culture steps,
wherein the ES cells are mouse or human ES cells.

14. The method of claim 13, wherein the ES cells are cultured on an oxygen permeable membrane.

* * * * *

UNITED STATES PATENT AND TRADEMARK OFFICE
CERTIFICATE OF CORRECTION

PATENT NO. : 9,029,147 B2
APPLICATION NO. : 12/664763
DATED : May 12, 2015
INVENTOR(S) : Colton et al.

Page 1 of 1

It is certified that error appears in the above-identified patent and that said Letters Patent is hereby corrected as shown below:

In the Specification

In Column 1, Lines 14-18, delete:
"This invention was made in part with government support under grant number RO1-DK063108-01A1, DK063108-03, and NCRR ICR U4Z 16606 from the National Institutes of Health (NIH). The government has certain rights in this invention."

And insert:
-- This invention was made with government support under DE020761 and R01 DK063108 awarded by the National Institutes of Health. The government has certain rights in the invention. --

Signed and Sealed this
Eleventh Day of November, 2025

John A. Squires
*Director of the United States Patent and Trademark Office*

SEQUENCE LISTING

```
<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
gaatccgcta aggagtgtgt aaca                                            24

<210> SEQ ID NO 2
<211> LENGTH: 18
<212> TYPE: DNA
<213> ORGANISM: Artificial Sequence
<220> FEATURE:
<223> OTHER INFORMATION: Synthetic
```

<400> SEQUENCE: 2
ctccagcgcc atccattt                                          18

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
cacgagtgga aagcaactca ga                                     22

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
tctccaactt cacggcattg                                        20

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
cctgattctt ctaccagtcc ca                                     22

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
ggcctgagag aacacagtcc                                        20

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
gacagctacg cgcacatga                                         19

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
ggtgcatcgg ttgcatctg                                         19

<210> SEQ ID NO 9

```
<211> LENGTH: 20
<212> TYPE: DNA
<213> ORGANISM: Artificial Sequence
<220> FEATURE:
<223> OTHER INFORMATION: Synthetic

<400> SEQUENCE: 9
cagtggagct ggacaaagcc                                           20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
tagcgacggt tctggaacca                                           20

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
gctggcgggt ctgaagtg                                             18

<210> SEQ ID NO 12
<211> LENGTH: 25
<212> TYPE: DNA
<213> ORGANISM: Artificial Sequence
<220> FEATURE:
<223> OTHER INFORMATION: Synthetic

<400> SEQUENCE: 12
taacttctgc tgaccattct cttga                                     25

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
gctggaacag agattggaag g                                         21

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
ccaggatctg agcgatctga c                                         21
```